United States Patent
Smith

(10) Patent No.: US 12,397,072 B2
(45) Date of Patent: Aug. 26, 2025

(54) SYSTEM, METHOD, AND DEVICE FOR FACILITATING EFFECTIVE DECONTAMINATION AS PART OF A DECONTAMINATION EVENT

(71) Applicant: Rememdia LC, Salt Lake City, UT (US)

(72) Inventor: Fraser M. Smith, Salt Lake City, UT (US)

(73) Assignee: Rememdia LC, Salt Lake City, UT (US)

( * ) Notice: Subject to any disclaimer, the term of this patent is extended or adjusted under 35 U.S.C. 154(b) by 938 days.

(21) Appl. No.: 17/371,046

(22) Filed: Jul. 8, 2021

(65) Prior Publication Data

US 2022/0011243 A1 Jan. 13, 2022

Related U.S. Application Data

(60) Provisional application No. 63/049,610, filed on Jul. 8, 2020.

(51) Int. Cl.
*A61L 2/00* (2006.01)
*A61L 2/24* (2006.01)
(Continued)

(52) U.S. Cl.
CPC ........... *A61L 2/0088* (2013.01); *A61L 2/0029* (2013.01); *A61L 2/24* (2013.01); *G01N 21/6408* (2013.01);
(Continued)

(58) Field of Classification Search
CPC ........ A61L 2/0029; A61L 2/0088; A61L 2/24; A61L 2/28; A61L 2202/17;
(Continued)

(56) References Cited

U.S. PATENT DOCUMENTS 5,900,067 A * 5/1999 Jones ................. G01N 21/6447
252/301.16
6,426,701 B1 7/2002 Levy et al.
(Continued)

FOREIGN PATENT DOCUMENTS

CN 205475491 U 8/2016
CN 210915412 U 7/2020
(Continued)

OTHER PUBLICATIONS

Machine Translation of DE 20-2017-107187 U1, cited in IDS filed Jul. 8, 2021 (Year: 2017).*
(Continued)

*Primary Examiner* — Jennifer Wecker
*Assistant Examiner* — Brady C Pilsbury
(74) *Attorney, Agent, or Firm* — Christopher L. Johnson

(57) ABSTRACT

Systems and methods for assessing the effectiveness of a decontamination event to decontaminate a portion of at least one of skin or a covering of the skin of an individual. A composition dispenser housing a power source and configured to dispense a composition with a fluorescent agent. A light module remote from the composition dispenser with a light source powered by the power source of the composition dispenser. The light source to emit light in accordance with a predetermined field of view, and to emit the light at a sufficient intensity and wavelength to cause a fluorescent agent dispensed by the agent dispensing system to fluoresce. The field of view defines an inspection space in which the portion of the individual can be positioned to detect at least one of a presence or an absence of the fluorescent agent during the decontamination event.

42 Claims, 35 Drawing Sheets

(51) Int. Cl.
| | |
|---|---|
| *G01N 21/64* | (2006.01) |
| *G01N 21/94* | (2006.01) |
| *G06K 19/06* | (2006.01) |
| *G06K 19/07* | (2006.01) |
| *G06V 10/60* | (2022.01) |
| *G06V 40/12* | (2022.01) |
| *G06V 40/20* | (2022.01) |
| *G08B 7/06* | (2006.01) |
| *G08B 21/24* | (2006.01) |

(52) U.S. Cl.
CPC ......... *G01N 21/6486* (2013.01); *G01N 21/94* (2013.01); *G06K 19/06009* (2013.01); *G06K 19/0723* (2013.01); *G06V 10/60* (2022.01); *G06V 40/1365* (2022.01); *G06V 40/28* (2022.01); *G08B 7/06* (2013.01); *G08B 21/245* (2013.01); *A61L 2202/14* (2013.01); *A61L 2202/17* (2013.01)

(58) Field of Classification Search
CPC ............... G01N 21/6486; G01N 21/94; G01N 2021/6439; G06K 19/06009; G08B 21/245
See application file for complete search history.

(56) References Cited

U.S. PATENT DOCUMENTS

| | | | |
|---|---|---|---|
| 6,727,818 B1 | 4/2004 | Wildman et al. | |
| 6,814,816 B2 | 11/2004 | Achar et al. | |
| 6,970,574 B1 | 11/2005 | Johnson | |
| 7,049,615 B1 | 5/2006 | Browne | |
| 7,443,305 B2 | 10/2008 | Verdiramo | |
| 7,755,494 B2 | 7/2010 | Melker et al. | |
| 7,770,782 B2 | 8/2010 | Sahud | |
| 8,040,245 B2 | 10/2011 | Koblasz | |
| 8,090,155 B2 | 1/2012 | Lacey et al. | |
| 8,146,613 B2 * | 4/2012 | Barnhill | G08B 21/245 134/119 |
| 8,377,229 B2 | 2/2013 | Barnhill et al. | |
| 9,478,118 B2 | 10/2016 | Keown et al. | |
| 9,526,380 B2 | 12/2016 | Hamilton et al. | |
| 9,613,518 B2 | 4/2017 | Dunn et al. | |
| 9,724,443 B2 | 8/2017 | Smith | |
| 9,940,819 B2 | 4/2018 | Ferniany | |
| 10,008,098 B2 * | 6/2018 | Ophardt | H04L 63/10 |
| 10,235,865 B2 | 3/2019 | Roff | |
| 10,332,382 B2 | 6/2019 | Thyroff | |
| 10,370,695 B2 | 8/2019 | Kanhye | |
| 10,410,507 B2 | 9/2019 | Pi | |
| 10,613,030 B2 | 4/2020 | Llamido | |
| 2002/0050006 A1 | 5/2002 | Saraya | |
| 2003/0197122 A1 | 10/2003 | Faiola et al. | |
| 2005/0253102 A1 | 11/2005 | Boilen | |
| 2008/0031838 A1 | 2/2008 | Bolling | |
| 2009/0087028 A1 | 4/2009 | Lacey et al. | |
| 2009/0237651 A1 * | 9/2009 | Arndt | A61K 49/0063 356/229 |
| 2010/0134296 A1 * | 6/2010 | Hwang | G08B 21/245 340/573.1 |
| 2014/0366264 A1 | 12/2014 | Ciavarella et al. | |
| 2015/0102061 A1 | 4/2015 | Larson et al. | |
| 2015/0144575 A1 * | 5/2015 | Hawkins | C02F 1/325 210/748.11 |
| 2016/0296077 A1 | 10/2016 | Smith | |
| 2016/0301844 A1 | 10/2016 | Smith | |
| 2018/0355592 A1 * | 12/2018 | Mandel | E03C 1/055 |
| 2019/0046679 A1 | 2/2019 | Stoloff et al. | |
| 2023/0270904 A1 * | 8/2023 | Simonovsky | A61L 2/24 4/668 |

FOREIGN PATENT DOCUMENTS

| | | | | |
|---|---|---|---|---|
| DE | 202017107187 U1 | | 2/2018 | |
| EP | 1201172 A2 | | 5/2002 | |
| EP | 3336817 A1 | | 6/2018 | |
| EP | 2622590 B1 | | 10/2019 | |
| EP | 3336817 B1 | | 10/2019 | |
| EP | 2163263 B1 | | 4/2020 | |
| GB | 2476908 B | | 12/2012 | |
| KR | 2013-0007072 A | | 1/2013 | |
| WO | WO-0061713 A1 * | | 10/2000 | ............. C11D 17/04 |
| WO | WO 2008/118143 A3 | | 10/2008 | |
| WO | WO 2018/208256 A2 | | 11/2018 | |

OTHER PUBLICATIONS

International Search Report for International Application No. PCT/US2021/040957 dated Dec. 10, 2021, 21 pages.
International Search Report for International Application No. PCT/US2021/040958 dated Dec. 8, 2021, 16 pages.
International Search Report for International Application No. PCT/US2021/040961 dated Dec. 9, 2021, 18 pages.
International Search Report for International Application No. PCT/US2021/040962 dated Dec. 10, 2021, 19 pages.
Davidhazy, The Wratten 18A A problematic filter for reflected ultraviolet photography, h https://people.rit.edu/andpph/text-ultraviolet-wratten-18A.html, retrieved on Jan. 22, 2015, 5 pages, retrieved from https://people.rit.edu/andpph/text-ultraviolet-wratten-18A.html.
British Columbia, Health Impacts of Exposure to Ultraviolet (UV) Radiation, http://www2.gov.bc.ca/gov/content/health/keeping-be-healthy-safe/radiation/ultraviolet-uv-radiation/health-impact-of-exposure-to-ultraviolet-uv-radiation, Jun. 28, 2016, 3 pages.

* cited by examiner

1000

| 1002 | Activating a composition dispenser to dispense a composition onto the portion of the skin or the covering of the skin of the individual to be decontaminated, the composition comprising a skin cleansing agent and a fluorescent agent capable of fluorescing when exposed to light |

↓

1004 — Activating a light source, in response to the composition dispenser being activated, the light source being supported in a light module located remote to the composition dispenser to emit light onto the portion of the skin or the covering of the skin of the individual in connection with the decontamination event, wherein the light causes any traces of the fluorescent agent to fluoresce at a wavelength in the visible spectrum, wherein the light is emitted in an inspection space located between an outlet of a water dispenser and a wash basin

↓

1006 — Applying the composition to the portion of the skin or the covering of the skin of the individual to be decontaminated

↓

1008 — With the portion of the skin or the covering of the skin of the individual exposed to the light, visually inspecting the portion of the skin or the covering of the skin of the individual to ensure the fluorescent agent has covered the portion of the skin of the covering of the skin of the individual

↓

1010 — Carrying out a decontamination procedure

↓

1012 — Applying water to the portion of the skin or covering of the skin of the individual to remove the composition

FIG. 10

SYSTEM, METHOD, AND DEVICE FOR FACILITATING EFFECTIVE DECONTAMINATION AS PART OF A DECONTAMINATION EVENT

RELATED APPLICATIONS

This application claims the benefit of U.S. Provisional Application Ser. No. 63/049,610, filed Jul. 8, 2020, and entitled, "System, Method, and Device for Facilitating Effective Decontamination as Part of a Decontamination Event", which is incorporated by reference in its entirety herein.

FIELD OF THE TECHNOLOGY

The present technology relates to methods and systems of cleaning or decontaminating skin, including hands and other parts of the body, as well as coverings over the skin such as gloves, and more particularly to methods and systems of decontaminating to eliminate or reduce contaminants and other potential hazards adhering to the skin or the covering of the skin an individual.

BACKGROUND OF THE TECHNOLOGY AND RELATED ART

At present, there is an ongoing and ever increasing concern over the spread of infectious diseases and other biological or chemical hazards and for infection control and/or the control of cross-contamination. As part of more extreme measures, persons suspected of being contaminated with chemical and/or biological agents are led into a decontamination tent, trailer, or pod, where they shed their potentially contaminated clothes in a strip-down room. They then enter a wash-down room and are showered. Finally, they enter a drying and re-robing room to be issued clean clothing, or a jumpsuit or the like. However, such decontamination procedures are difficult to employ and impractical for routine washing or decontamination, such as in residential or commercial settings (e.g., private or public restrooms) and health care settings, such as hospitals and other health care settings.

A washing or decontamination procedure in a hospital setting often employs soap and/or an antiseptic agent together with a specific scrubbing protocol. Chemical preparations (other than soap) for hand hygiene can be used, for example, chlorhexidine gluconate (clear/pink solution); iodine based preparations (brown); and aqueous alcoholic solutions (clear), though iodine based preparations have been known to cause skin irritation. For surgical procedures, hand-washing begins at the fingernails, where a nail file and brush from a sterile pack can be used. Scrubbing then occurs in three washing cycles: (a) hands and arms extending to two inches above the elbow; (b) hands and half way up the forearms; and (c) hands only. This follows the principle of washing from a clean area (the hand) in the direction of the less clean area (the arm). Hands should always be held above the level of the elbows at all times in order to prevent dirty water from dripping from the upper arm onto lower sterile areas.

Hospital-acquired infections are a major cause of illness and death, and impose serious economic costs on patients and hospitals. Indeed, health care-associated infections result in an estimated 90,000 deaths each year in the United States. Cross transmission is estimated to cause 40% of certain infections. Pathogens are readily transmitted on the hands of a healthcare worker, and effective hand hygiene substantially reduces this transmission. For decades, hand-washing has been universally accepted as one of the most important measures for preventing transmission of pathogens in health-care facilities and other community settings. However, compliance with established hand-washing guidelines remains poor. When it comes to public and private settings where hand washing is required, expected or at least encouraged, the public is often uneducated or unfamiliar with proper hand washing techniques to effectively decontaminate their hands and other skin covered areas. It is therefore necessary to improve the methods and systems of decontamination during a washing event, such as before a surgery or any other event where the spread of a chemical or biological contaminant is possible.

SUMMARY OF THE INVENTION

In light of the problems and deficiencies inherent in the prior art, the present invention seeks to overcome these by providing a system for facilitating effective decontamination of the skin or covering of the skin of an individual during a decontamination event, including assessing or facilitating assessing the effectiveness of the decontamination (i.e., a washing) event. In accordance with one aspect of the technology, a water dispenser is provided that is operable or configured to facilitate assessing the effectiveness of a decontamination event to decontaminate a portion of at least one of skin or a covering of the skin of an individual. The water dispenser comprises a housing, wherein the water dispenser is adapted to communicate water from a water source to at least one of the skin or the covering of the skin of the individual. The water dispenser further comprises an actuator configured to open a valve to cause the water dispenser to release water. The water dispenser further comprises a light source supported in the housing so as to emit light in accordance with a predetermined field of view, wherein the light source is configured to emit the light at a sufficient intensity and wavelength so as to cause a fluorescent agent disposed about the skin or the covering of the skin of the individual to fluoresce at a wavelength in the visible spectrum, the field of view defines, at least in part, an inspection space in which the portion of the skin of the individual can be positioned to detect at least one of a presence or an absence of fluorescing fluorescent agent during the decontamination event. The water dispenser further comprises a timer supported in the housing, the timer having a timer program configured to activate the actuator to dispense water for a first predetermined period of time, and configured to activate the light source for a second predetermined period of time.

In accordance with an additional aspect of the technology, a system is provided for facilitating effective decontamination of a portion of at least one of skin or a covering of the skin of an individual as part of a decontamination event. The system comprises a water dispenser adapted to communicate water from a water source to at least one of the skin or the covering of the skin of the individual. The water dispenser comprising a housing. The water dispenser further comprises an actuator configured to open a valve to cause the water dispenser to release water. The water dispenser further comprises a light source supported in the housing so as to emit light in accordance with a predetermined field of view, wherein the light source is configured to emit the light at a sufficient intensity and wavelength so as to cause a fluorescent agent disposed about the skin or the covering of the skin of the individual to fluoresce at a wavelength in the visible spectrum, the field of view defines, at least in part, an inspection space in which the portion of the skin or the covering of the skin of the individual can be positioned to detect at least one of the presence or absence of fluorescing fluorescent agent during the decontamination event. The water dispenser further comprises a timer supported in the housing, the timer having a timer program configured to activate the actuator to dispense water for a first predetermined period of time and configured to activate the light source for a second predetermined period of time. The system further comprises a wash basin configured to capture the water and drain the water away. The system further comprises a composition dispenser configured to dispense a composition comprising a skin cleansing agent and the fluorescent agent, the fluorescent agent being capable of fluorescing when exposed to light, the composition dispenser comprising a chamber for holding the composition, and an actuator configured to activate a pump to facilitate dispensing of the composition.

In accordance with another aspect of the technology, a method for facilitating effective decontamination of a portion of at least one of skin or a covering of the skin of an individual as part of a decontamination event comprising activating, via a first touchless sensor, a water dispenser for a first period of time as controlled by a timer, the water dispenser being operable to dispense water onto a portion of the skin or the covering of the skin of the individual. The method further comprises applying a composition to the portion of the skin or the covering of the skin of the individual, wherein the composition comprises a skin cleansing agent and a fluorescent agent capable of fluorescing when exposed to light. The method further comprises activating, via a second touchless sensor, a light source for a second period of time as controlled by the timer, the light source being operable to emit light onto the portion of the skin or the covering of the skin of the individual and the composition as applied thereon. The method further comprises initiating a decontamination procedure as part of the decontamination event to effectuate the decontamination of the portion of the skin or the covering of the skin of the individual. The method further comprises activating the water dispenser for a third period of time as controlled by the timer to rinse the composition from the portion of the skin or the covering of the skin of the individual, wherein the water is dispensed during the third period of time concurrent with the emission of the light during at least a portion of the second period of time.

In accordance with another aspect of the technology, a method facilitating effective decontamination of a portion of at least one of skin or a covering of the skin of an individual as part of a decontamination event comprising activating, by way of a first movement of the individual detected by a touchless sensor of a water dispenser, a timer program controlled by a timer. Activating the first timer program comprises the step of activating an actuator to communicate water from the water dispenser to the portion of the skin or the covering of the skin of the individual for a first period of time. Activating the first timer program further comprises causing a light source of the water dispenser to emit light from a light source onto the portion of the skin or the covering of the skin of the individual of an individual at a sufficient intensity and wavelength so as to cause a fluorescent agent within a composition disposed about the skin or the covering of the skin of the individual to fluoresce at a wavelength in the visible spectrum for a second period of time, wherein the composition comprises a skin cleansing agent and the fluorescing agent. Activating the first timer program further comprises activating the actuator for a third period of time to communicate water from the water dispenser to the portion of the skin or the covering of the skin of the individual concurrent with the emission of the light during at least a portion of the second period of time.

In accordance with an additional aspect of the technology, a water dispenser is provided for facilitating effective decontamination of a portion of at least one of skin or a covering of the skin of an individual as part of a decontamination event. The water dispenser comprises a housing, wherein the water dispenser is adapted to communicate water from a water source to the skin or a covering of the skin of the individual. The water dispenser further comprises an agent dispensing system supported in the housing and configured to dispense a composition from a chamber via a conduit that passes through the housing, the composition comprising a skin cleansing agent and a fluorescent agent capable of fluorescing when exposed to light. The water dispenser further comprises a light source supported in the housing so as to emit light in accordance with a predetermined field of view, wherein the light source is configured to emit the light at a sufficient intensity and wavelength so as to cause the fluorescent agent disposed about the skin or a covering of the skin of the individual to fluoresce at a wavelength in the visible spectrum, the field of view defines, at least in part, an inspection space in which the portion of the skin or the covering of the skin of the individual can be positioned to detect the at least one of a presence or an absence of fluorescing fluorescent agent during the decontamination event.

In accordance with an additional aspect of the technology, a system is provided for facilitating effective decontamination of a portion of at least one of skin or a covering of the skin of an individual as part of a decontamination event. The system comprises a wash basin configured to capture water and drain the water away. The system further comprises a chamber for holding a composition comprising a skin cleansing agent and a fluorescent agent capable of fluorescing when exposed to light. The system further comprises a water dispenser adapted to communicate the water from a water source to the skin or a covering of the skin of the individual. The water dispenser comprises a housing. The water dispenser further comprises an agent dispensing system supported in the housing configured to dispense the composition from the chamber via a conduit that passes through the housing. The water dispenser further comprises a light source supported in the housing so as to emit light in accordance with a predetermined field of view, wherein the light source is configured to emit the light at a sufficient intensity and wavelength so as to cause the fluorescent agent disposed about the skin or a covering of the skin of the individual to fluoresce at a wavelength in the visible spectrum, and wherein the field of view defines, at least in part, an inspection space in which the portion of the skin or the covering of the skin of the individual can be positioned to detect the presence or absence of fluorescing fluorescent agent during the decontamination event.

In accordance with another aspect of the technology, a method for facilitating effective decontamination of a portion of at least one of skin or a covering of the skin of an individual as part of a decontamination event. The method further comprises activating the water dispenser to dispense water onto the portion of the skin or the covering of the skin of the individual to be decontaminated. The method further comprises activating an agent dispensing system supported in the water dispenser to dispense a composition, the composition comprises a skin cleansing agent and a fluorescent agent capable of fluorescing when exposed to light. The method further comprises applying the composition to the portion of the skin or the covering of the skin of the individual to be decontaminated. The method further comprises initiating a decontamination procedure as part of the decontamination event to effectuate the decontamination of the portion of the skin or the covering of the skin of the individual and to remove the composition. The method further comprises activating a light source supported in the water dispenser to emit light onto the portion of the skin or the covering of the skin of the individual in connection with the decontamination event, wherein the light causes any traces of the fluorescent agent to fluoresce at a wavelength in the visible spectrum. With the portion of the skin or the covering of the skin of the individual exposed to the light, the method further comprises visually inspecting the portion of the skin or the covering of the skin of the individual to ensure the fluorescent agent has covered the portion of the skin or the covering of the skin of the individual. The method further comprises applying water to the portion of the skin or the covering of the skin of the individual to remove the composition.

In accordance with an additional aspect of the technology, dispensing apparatus attachable to a water dispenser for facilitating effective decontamination of a portion of at least one of skin or a covering of the skin of an individual as part of a decontamination event. The dispensing apparatus comprises a housing. The dispensing apparatus further comprises a water dispenser interface supported by the housing and configured to couple the housing to the water dispenser, wherein the water dispenser is adapted to communicate water from a water source to the skin or covering of the skin of the individual. The dispensing apparatus further comprises a water dispensing system comprising a water conduit, the water dispensing system configured to pass the water from the water dispenser through the housing to dispense the water. The dispensing apparatus further comprises an agent dispensing system supported in the housing configured to dispense a composition from a chamber via a composition conduit that passes through the housing, the composition comprising a skin cleansing agent and a fluorescent agent capable of fluorescing when exposed to light. The dispensing apparatus further comprises a light source supported in the housing so as to emit light in accordance with a predetermined field of view, wherein the light source is configured to emit the light at a sufficient intensity and wavelength so as to cause the fluorescent agent disposed about the skin or a covering of the skin of the individual to fluoresce at a wavelength in the visible spectrum, and wherein the field of view defines, at least in part, an inspection space in which the portion of the skin or the covering of the skin of the individual can be positioned to detect the presence or absence of fluorescing fluorescent agent during the decontamination event.

In accordance with an additional aspect of the technology, a system is provided for facilitating effective decontamination of a portion of at least one of skin or a covering of the skin of an individual as part of a decontamination event. The system comprises a water dispenser adapted to communicate water from a water source to the skin or covering of the skin of the individual. The system further comprises a wash basin configured to capture the water and drain the water away. The system further comprises a chamber for holding a composition comprising a skin cleansing agent and a fluorescent agent capable of fluorescing when exposed to light. The system further comprises a dispensing apparatus with a housing. The dispensing apparatus comprises a water dispenser interface configured to couple the housing to the water dispenser. The dispensing apparatus further comprises a water dispensing system comprising a water conduit, the water dispensing system configured to pass the water from the water dispenser through the housing to dispense the water. The dispensing apparatus further comprises an agent dispensing system positioned in the housing configured to dispense a composition from the chamber via a composition conduit that passes through the housing, the composition comprising a skin cleansing agent and a fluorescent agent capable of fluorescing when exposed to light. The dispensing apparatus further comprises a light source positioned in the housing so as to emit light in accordance with a predetermined field of view, wherein the light source is configured to emit the light at a sufficient intensity and wavelength so as to cause the fluorescent agent disposed about the skin or a covering of the skin of the individual to fluoresce at a wavelength in the visible spectrum, and wherein the field of view defines, at least in part, an inspection space in which the portion of the skin or the covering of the skin of the individual can be positioned to detect the presence or absence of fluorescing fluorescent agent during the decontamination event.

In accordance with another aspect of the technology, a method for facilitating effective decontamination of a portion of at least one of skin or a covering of the skin of an individual as part of a decontamination event comprising accessing a dispensing apparatus coupled to a water dispenser operable to direct water to the dispensing apparatus, wherein the dispensing apparatus is configured to control the dispensing of the water. The method further comprises activating a water dispensing system of the dispensing apparatus to dispense the water onto the portion of the skin or the covering of the skin of the individual to be decontaminated. The method further comprises activating an agent dispensing system of the dispensing apparatus to dispense a composition, wherein the composition comprises a skin cleansing agent and an fluorescent agent capable of fluorescing when exposed to light. The method further comprises applying the composition to the portion of the skin or the covering of the skin of the individual to be decontaminated. The method further comprises initiating a decontamination procedure as part of the decontamination event to effectuate the decontamination of the portion of the skin or the covering of the skin of the individual and to remove the composition. The method further comprises activating a light source supported in the dispensing apparatus to emit light onto the portion of the skin or the covering of the skin of the individual in connection with the decontamination event, wherein the light causes any traces of the fluorescent agent to fluoresce at a wavelength in the visible spectrum. The method further comprises with the portion of the skin or the covering of the skin of the individual exposed to the light, visually inspecting the portion of the skin or the covering of the skin of the individual to ensure the fluorescent agent has covered the portion of the skin of the covering of the skin of the individual. The method further comprises applying water to the portion of the skin or covering of the skin of the individual to remove the composition.

In accordance with an additional aspect of the technology, a system is provided for facilitating effective decontamination of a portion of at least one of skin or a covering of the skin of an individual as part of a decontamination event. The system comprises a composition dispenser having a dispenser housing, the composition dispenser configured to dispense a composition from a chamber supported in the dispenser housing, the composition comprising a skin cleansing agent and a fluorescent agent capable of fluorescing when exposed to light, the composition dispenser further comprising a power source supported by the dispenser housing. The system further comprises a light module having a module housing, and located remote to the composition dispenser, the light module further comprising a light source supported by the module housing and powered by the power source so as to emit light in accordance with a predetermined field of view. The system further comprises a cable connecting the composition dispenser and the light module. The light source is configured to emit the light at a sufficient intensity and wavelength so as to cause the fluorescent agent disposed about the skin or the covering of the skin of the individual to fluoresce at a wavelength in the visible spectrum. The field of view defines, at least in part, an inspection space located between a wash basin and an outlet of a water dispenser in which the portion of the skin or the covering of the skin of the individual can be positioned to detect the presence or absence of fluorescing fluorescent agent during the decontamination event.

In accordance with an additional aspect of the technology, a system is provided for facilitating effective decontamination of a portion of at least one of skin or a covering of the skin of an individual as part of a decontamination event. The system comprises a composition dispenser with a dispenser housing, the composition dispenser configured to dispense a composition from a chamber supported in the dispenser housing, the composition comprising a skin cleansing agent and a fluorescent agent capable of fluorescing when exposed to light, the composition dispenser further comprising a power source supported by the dispenser housing. The system further comprises a light module having a module housing and a light module interface supported by the module housing, wherein the light module interface is configured to couple the light module to an outlet of a water dispenser adapted to communicate water from a water source to the skin or covering of the skin of the individual. The system further comprises a cable connecting the composition dispenser to the light module. The system further comprises a water conduit configured to pass the water from the water dispenser through the module housing to dispense the water. The system further comprises a light source supported by the module housing and powered by the power source via the power cable so as to emit light in accordance with a predetermined field of view, wherein the light source is configured to emit the light at a sufficient intensity and wavelength so as to cause the fluorescent agent disposed about the skin or the covering of the skin of the individual to fluoresce at a wavelength in the visible spectrum. The field of view defines, at least in part, an inspection space located between a wash basin and the outlet of the water dispenser in which the portion of the skin or the covering of the skin of the individual can be positioned to detect the presence or absence of fluorescing fluorescent agent during the decontamination event.

In accordance with an additional aspect of the technology, a system is provided for facilitating effective decontamination of a portion of at least one of skin or a covering of the skin of an individual as part of a decontamination event. The system comprises a composition dispenser having a dispenser housing, the composition dispenser configured to dispense a composition from a chamber supported in the dispenser housing, the composition comprising a skin cleansing agent and a fluorescent agent capable of fluorescing when exposed to light, the composition dispenser further comprising a power source supported by the dispenser housing. The system further comprises a water dispenser having a water dispenser housing, and being adapted to communicate water from a water source to the skin or covering of the skin of the individual through an outlet, the water dispenser further comprising a light source supported by the water dispenser housing and powered by the power source of the composition dispenser so as to emit light in accordance with a predetermined field of view. The system further comprises a cable connecting the water dispenser to the composition dispenser. The light source is configured to emit the light at a sufficient intensity and wavelength so as to cause the fluorescent agent disposed about the skin or the covering of the skin of the individual to fluoresce at a wavelength in the visible spectrum. The field of view defines, at least in part, an inspection space located between a wash basin and the outlet of the water dispenser in which the portion of the skin or the covering of the skin of the individual can be positioned to detect the presence or absence of fluorescing fluorescent agent during the decontamination event.

In accordance with another aspect of the technology, a method for facilitating effective decontamination of a portion of at least one of skin or a covering of the skin of an individual as part of a decontamination event. The method comprises activating a composition dispenser to dispense a composition onto the portion of the skin or the covering of the skin of the individual to be decontaminated, the composition comprising a skin cleansing agent and a fluorescent agent capable of fluorescing when exposed to light. The method further comprises activating a light source, in response to the composition dispenser being activated, the light source being supported in a light module located remote to the composition dispenser to emit light onto the portion of the skin or the covering of the skin of the individual in connection with the decontamination event, wherein the light causes any traces of the fluorescent agent to fluoresce at a wavelength in the visible spectrum, wherein the light is emitted in an inspection space located between an outlet of a water dispenser and a wash basin. The method further comprises applying the composition to the portion of the skin or the covering of the skin of the individual to be decontaminated. With the portion of the skin or the covering of the skin of the individual exposed to the light, the method further comprises visually inspecting the portion of the skin or the covering of the skin of the individual to ensure the fluorescent agent has covered the portion of the skin of the covering of the skin of the individual. The method further comprises carrying out a decontamination procedure. The method further comprises applying water to the portion of the skin or covering of the skin of the individual to remove the composition.

BRIEF DESCRIPTION OF THE DRAWINGS

The present technology will become more fully apparent from the following description and appended claims, taken in conjunction with the accompanying drawings. Understanding that these drawings merely depict exemplary aspects of the present technology they are, therefore, not to be considered limiting of its scope. It will be readily appreciated that the components of the present technology, as generally described and illustrated in the figures herein, could be arranged and designed in a wide variety of different configurations. Nonetheless, the technology will be described and explained with additional specificity and detail through the use of the accompanying drawings in which:

FIG. 10 is a flow chart illustrating certain aspects of the technology.

DETAILED DESCRIPTION OF EXEMPLARY ASPECTS OF THE TECHNOLOGY

Figure 1A:
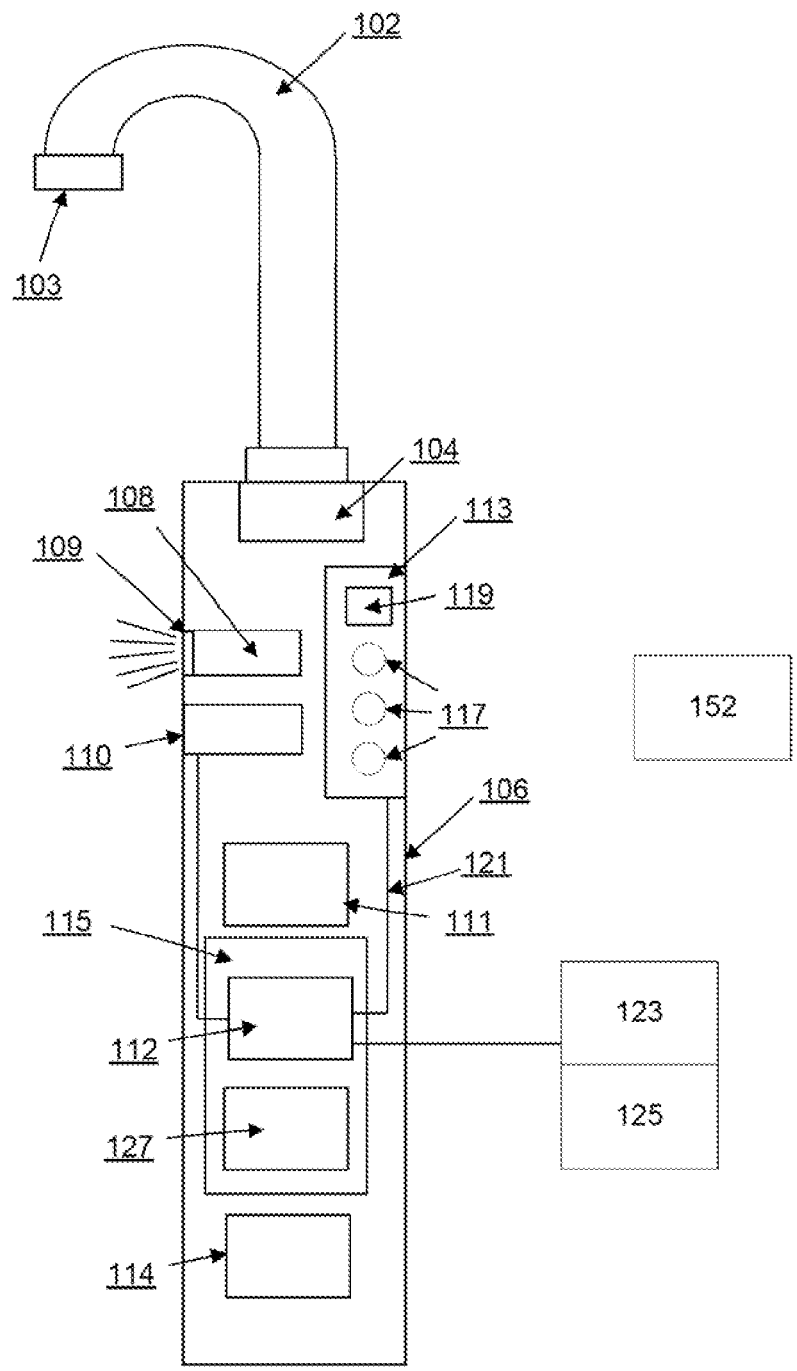
FIGS. 1A-G are block diagrams of water dispensers and systems with a timer program for facilitating assessing the effectiveness of a decontamination event to decontaminate a portion of at least one of skin or a covering of the skin of an individual in accordance with aspects of the technology.
Figure 1B:
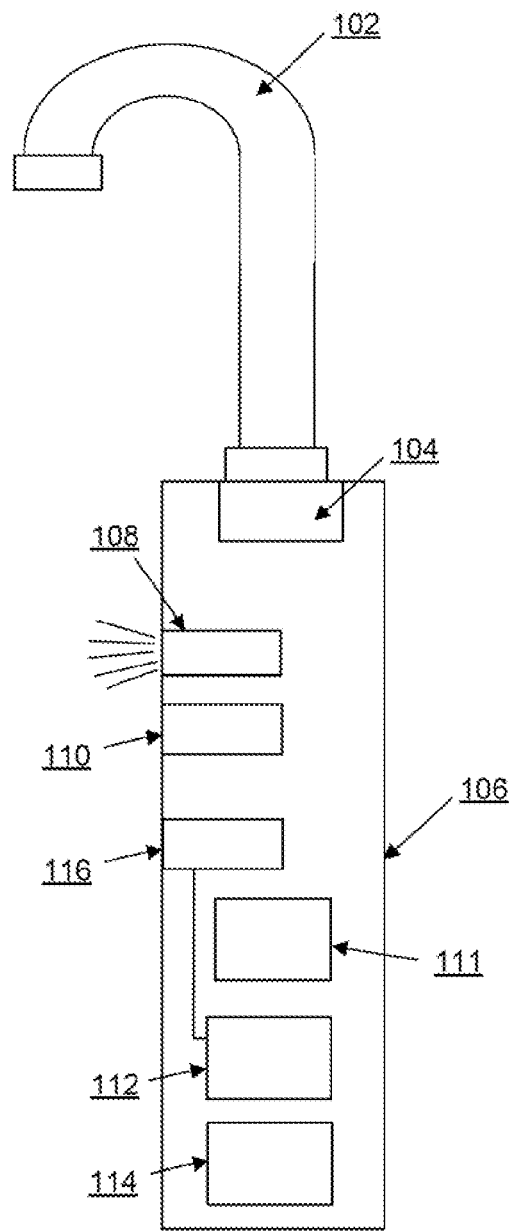
Figure 1C:
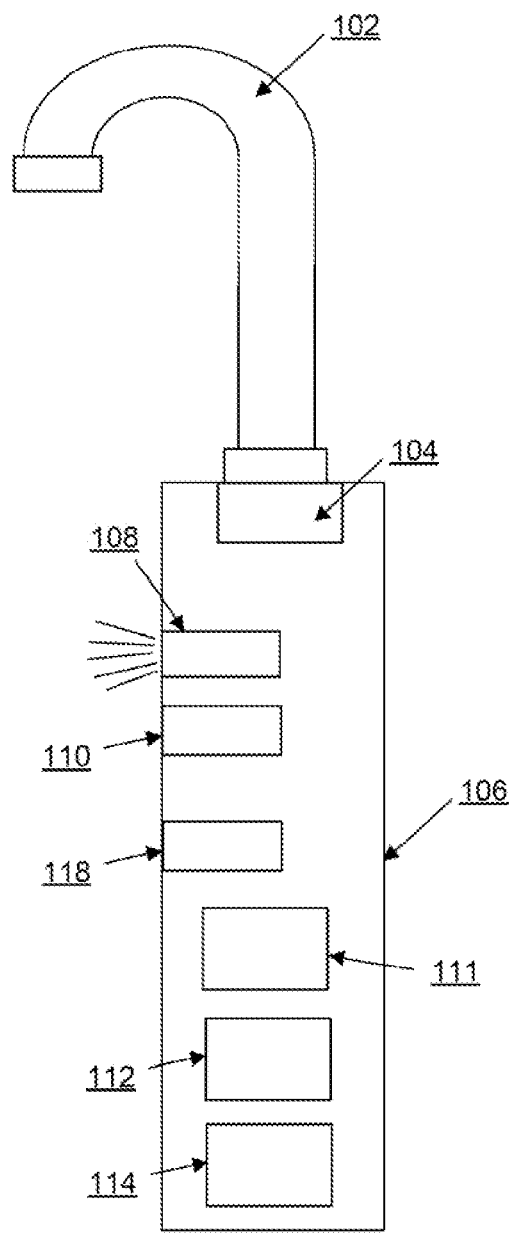
Figure 1D:
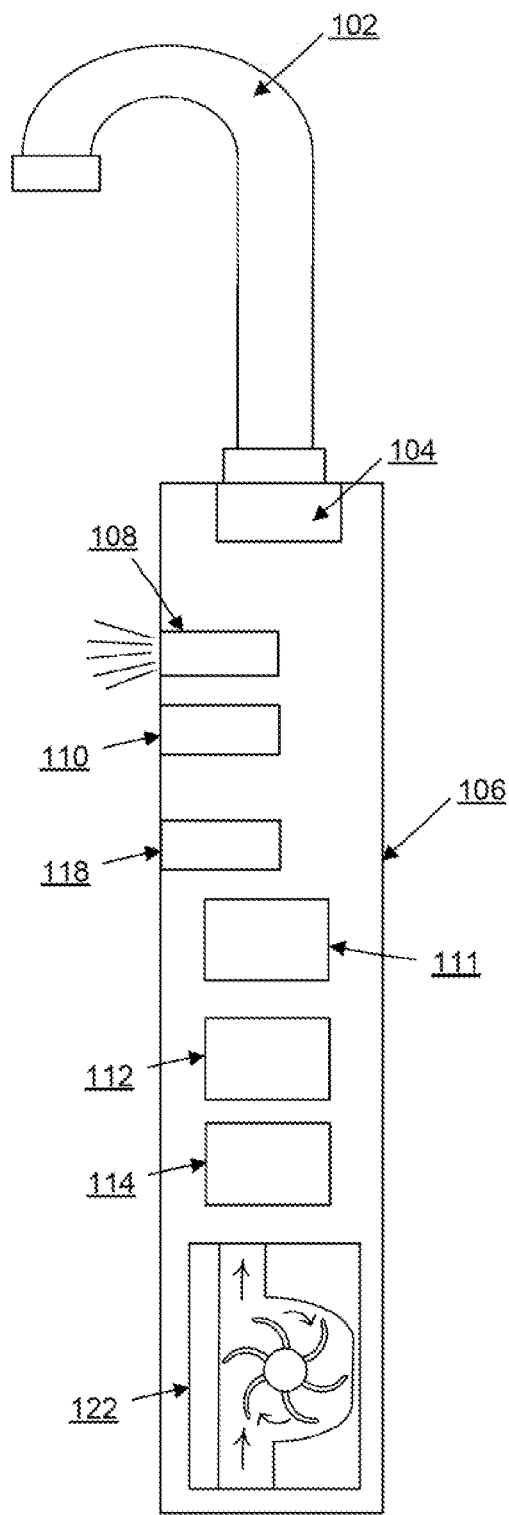
Figure 1E:
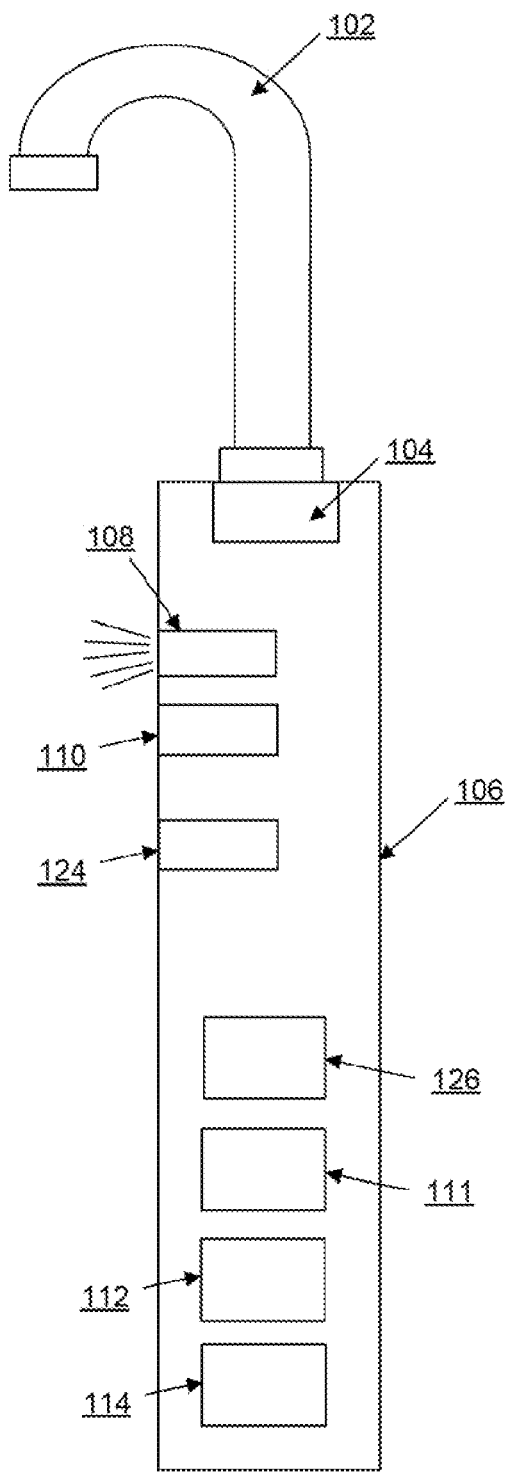
Figure 1F:
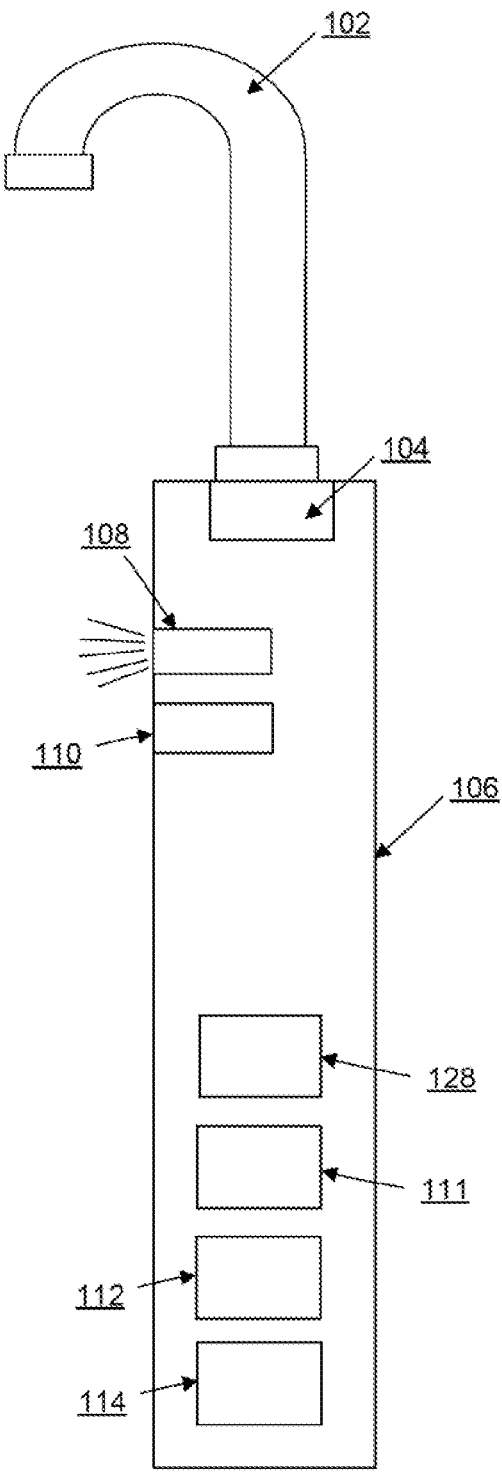

The following detailed description of exemplary aspects of the technology makes reference to the accompanying drawings, which form a part hereof and in which are shown, by way of illustration, exemplary aspects in which the technology may be practiced. While these exemplary aspects are described in sufficient detail to enable those skilled in the art to practice the technology, it should be understood that other aspects may be realized and that various changes to the technology may be made without departing from the spirit and scope of the present technology. Thus, the following more detailed description of the aspects of the present technology is not intended to limit the scope of the technology, as claimed, but is presented for purposes of illustration only and not limitation to describe the features and characteristics of the present technology, to set forth the best mode of operation of the technology, and to sufficiently enable one skilled in the art to practice the technology. Accordingly, the scope of the present technology is to be defined solely by the appended claims. The following detailed description and exemplary aspects of the technology will be best understood by reference to the accompanying drawings, wherein the elements and features of the technology are designated by numerals throughout.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context. In addition, adjacent can refer to two like elements that are near or close to one another, with some other type of device or object disposed between them.

As used herein, the term "decontamination event" refers to all steps or procedures associated with decontaminating a portion of the skin or a covering of the skin of an individual, to all steps or procedures associated with assessing or facilitating the assessment of the effectiveness of a decontamination procedure, and to all steps or procedures associated with repeated decontamination procedures and subsequent assessment of the effectiveness of such repeated procedures as often as necessary.

As used herein, the term "decontamination procedure" refers to an actual washing procedure or protocol, such as the steps or procedures associated with applying and scrubbing a composition to a portion of the skin or a covering of the skin of an individual as well as rinsing the portion of the skin or the covering of the skin of the individual with water to remove the composition.

As used herein, "skin" or "portion of skin" refers to a portion of skin of an individual that is to be subjected to a decontamination event/procedure, such as or including the hands of the individual.

As used herein, "covering" or "covering of skin" refers to a covering over a portion of skin of an individual such as a glove. Decontamination events and procedures referred to herein can apply to either the skin or the covering of the skin of an individual.

An initial overview of the inventive concepts are provided below and then specific. examples are described in further detail later. This initial summary is intended to aid readers in understanding the examples more quickly, but is not intended to identify key features or essential features of the examples, nor is it intended to limit the scope of the claimed subject matter.

The present technology describes systems, devices, and methods for improved decontamination. Previous decontamination practices, including those related to hand washing, fall short of the acceptable removal of biological or chemical hazards. Several publications have described the use of soap or other disinfectant solutions that can change color or physical property as a function of time after it has been dispensed onto the hands. See, for example, U.S. Pat. No. 7,053,029, U.S. Patent Publication Nos. 2006/0264346, 2005/0233919, 2005/0233918, 2005/0090414. Other publications (U.S. Pat. Nos. 5,900,067 and 6,524,390 and U.S. Patent Publication No. 2012/0214879) introduce a fluorescent agent into the soap solution and examine the hands after rinsing to see whether any fluorescence is left behind to assure the hands no longer have soap left over. These methods, however, suffer from a soap-application bias and inefficiencies in the washing process. When the person that applies the soap to the hands and proceeds to wash his or her hands, the person may not evenly distribute soap across the hands or to all areas of the hands that may have a biological or chemical hazard present. Indeed, the places where biological or chemical hazards may persist on the hands of a person may be the hardest places to deliver the soap. In other words, the same method that a person uses to remove the soap is likely used to apply the soap, both of which result in inadequate coverage about the hands of the person. A method that begins with hands that are open with the fingers and thumb spread apart and covered with a liquid having a marking agent (e.g., a fluorescing compound) minimizes the soap-application bias.

In addition, the action of washing a portion of skin or a covering of the skin and then placing the skin or covering under a remote light source intended to cause residual luminescent compounds on the hands to luminesce becomes cumbersome and time consuming which can result in users skipping important washing procedures or failing to observe the presence of residual luminescence. Light sources with a field of view that is directed at the area used for washing, however, create an environment where the user can observe the presence of residual luminescence in real-time during a decontamination event or procedure. It is believed that this feature saves time and helps produce an increased level of decontamination on the part of the user, as well as serving to educate persons on the steps and actions needed to effectuate proper and effective decontamination during a decontamination event. Moreover, with the light source associated directly with the location of the washing event, methods and timing constructs can be employed to train individuals to continue the washing event until all (or an acceptable level) of the luminescence is removed from the hands without having to stop the washing event, move to a light source, and begin a new washing event if residual luminescence is not removed to an acceptable level.

It is intended that the present technology be operable with different types of water dispensers including functional attachments or components and compositions with the end result of improved systems, apparatuses, devices, and methods for decontamination. Bearing that in mind, aspects of the technology can be broadly described as systems and methods for decontaminating a portion of the skin or a covering of the skin of an individual.

Water Dispenser with a Timer Program

In one example, during a decontamination event an individual may wash their hands using a composition that has a cleansing agent, such as soap, and a fluorescent agent. The fluorescent agent is designed to fluoresce under light that has a sufficient intensity and that is emitted at a specific wavelength or within a range of wavelengths. Using a composition with a fluorescent agent assists the individual in knowing where the composition with the cleansing agent has been applied to the skin of the individual. This provides the individual with visual feedback that all of the desired areas of skin have been covered with the cleansing agent. Then after a rinsing procedure has been accomplished, the fluorescent agent assists the individual with visual feedback to determine whether all of the composition has been rinsed off the skin of the individual. The water dispenser can include a housing that supports components of the present technology. The housing can support the light source and timer. The timer can include timer programs to control activation of the dispensing of water from the water dispenser and to control the emission of light from the light source. The timer programs can have a sequence of predetermined periods of time to dispense the water and emit the light simultaneously or separately. The water dispenser can have one or more touchless sensors to trigger a given timer program. Different timer programs can be triggered via different touchless sensors or the same touchless sensor can be used to trigger different timer programs using different movements from the individual. An image capturing system can also be supported by the water dispenser and can be used to identify the individual as well as record the decontamination event.

Water Dispenser with a Light Source and an Agent Dispensing System

In one example, during a decontamination event an individual may wash their hands using a composition that has a cleansing agent, such as soap, and a fluorescent agent. The fluorescent agent is designed to fluoresce under light that has a sufficient intensity and that is emitted at a specific wavelength or within a wavelength range. Using a composition with a fluorescent agent assists the individual in knowing where the composition with the cleansing agent has been applied to the skin of the individual. This provides the individual with visual feedback that all of the desired areas of skin have been covered with the cleansing agent. Then after a rinsing procedure has been accomplished, the fluorescent agent assists the individual with visual feedback to determine whether all of the composition has been rinsed off the skin of the individual. The water dispenser can include a housing that supports components of the present technology. The housing can support the light source and an agent dispensing system. The agent dispensing system can dispense the composition from a remote composition chamber. A conduit in fluid connection or communication with the remote composition chamber can be formed through the water dispenser to facilitate delivery of the composition to the water dispenser to be dispensed through a water outlet in the water dispenser. The water dispenser can have one or more touchless sensors to trigger the dispensing of the water, the dispensing of the composition, and/or the emission of the light. An image capturing system can also be supported by the water dispenser and can be used to identify the individual as well as record the decontamination event.

Water Dispenser Retro Fitted with a Dispensing Apparatus

In one example, during a decontamination event an individual may wash their hands using a composition that has a cleansing agent, such as soap, and a fluorescent agent. The fluorescent agent is designed to fluoresce under light that has a sufficient intensity and that is emitted at a specific wavelength or within a wavelength range. Using a composition with a fluorescent agent assists the individual in knowing where the composition with the cleansing agent has been applied to the skin of the individual. This provides the individual with visual feedback that all of the desired areas of skin have been covered with the cleansing agent. Then after a rinsing procedure has been accomplished, the fluorescent agent assists the individual with visual feedback to determine whether all of the composition has been rinsed off the skin of the individual. An existing water dispenser can be retrofitted with a dispensing apparatus that supports components of the present technology. Water from the water dispenser can pass through a conduit in the dispensing apparatus and through a water outlet in the dispensing apparatus. The dispensing apparatus can support the light source and an agent dispensing system. The agent dispensing system can dispense the composition from a remote composition chamber. A conduit in fluid connection or communication with the remote composition chamber can be formed through the dispensing apparatus to facilitate delivery of the composition to the dispensing system to be dispensed through a water outlet in the dispensing apparatus. The dispensing apparatus can have one or more touchless sensors to trigger the dispensing of the water, the dispensing of the composition, and/or the emission of the light. An image capturing system can also be supported by the dispensing apparatus and can be used to identify the individual as well as record the decontamination event.

Composition Dispenser with a Remote Light Module

In one example, during a decontamination event an individual may wash their hands using a composition that has a cleansing agent, such as soap, and a fluorescent agent. The fluorescent agent is designed to fluoresce under light that has a sufficient intensity and that is emitted at a specific wavelength or within a wavelength range. Using a composition with a fluorescent agent assists the individual in knowing where the composition with the cleansing agent has been applied to the skin of the individual. This provides the individual with visual feedback that all of the desired areas of skin have been covered with the cleansing agent. Then after a rinsing procedure has been accomplished, the fluorescent agent assists the individual with visual feedback to determine whether all of the composition has been rinsed off the skin of the individual. A composition dispenser can be employed to dispense the composition. The composition dispenser may have a power source to power components of the composition dispenser as well as components of a light module. The light module may be located remote to the composition dispenser and connected to the composition dispenser via a cable. The cable may be comprised of a plurality of cables or wires that can be employed to provide electrical power and data connection for the components of the light module. The light module may have a housing that supports the components of the light module including a light source. The light source may emit light with a field of view that defines an inspection area that is between an outlet of a water dispenser and a wash basin. The light module may be retrofitted onto an existing water dispenser. For example, the light module may be fitted onto the base or the outlet of the water dispenser or any other structure of the water dispenser. The light module may also be mounted to another structure such as a wash basin, a backsplash, a counter top, a wall, etc. The light module may also be free standing and not mounted or attached to another structure. Alternatively, the light module may be purpose built into a water dispenser.

With reference now to the drawings, and with specific reference to FIGS. 1A-G, in accordance with one example, the present disclosure sets forth a water dispenser 102 operable to facilitate effective decontamination of a portion of at least one of skin or a covering of the skin of an individual during a decontamination event, including assessing or facilitating assessing the effectiveness of a decontamination procedure as part of the decontamination event. Indeed, the water dispenser 102 can be constructed or manufactured for purposes of assessing the effectiveness of a decontamination event to decontaminate a portion of at least one of skin or a covering of the skin of an individual. The water dispenser 102 can be adapted to communicate water from a water source 1 to at least one of the skin or the covering of the skin of the individual. For example, the water dispenser 102 can be referred to as a faucet. The water source 1 can comprise a water supply line 3 in communication with a pressurized water main (not shown) from a water utility company or a well or other type of water source.

The water dispenser 102 can comprise a housing 106 and a water outlet 103. The housing 106 can be composed of a material that is suitable for dispensing water such metal, a metal alloy, a composite material, a plastic, etc., and for supporting the various components of the water dispenser 102. The housing 106 can be formed and shaped and configured to include and support components of the present technology. The housing 106 may be described as comprising the structure (e.g., inner and outer shells, base, or other structures) of the water dispenser 102. In addition, the housing 106 of the water dispenser 102 can support the various tubes or conduits that are part of the water dispenser 102, and that are in place to facilitate the dispensing of water. The housing 106 can further support any handles or other components. The water dispenser 102 may comprise a mounting component (mounting structure, fasteners, etc.) configured to facilitate the mounting of the water dispenser 102 to another structure. For example, the water dispenser 102 may be mounted to a horizontal surface such as a counter top, a wall, or it may be mounted to a wash basin using the mounting components. In one aspect, the housing 106 can comprise first and second shell portions that fit together and that are separable, at least partially (e.g., via a hinge), from one another to facilitate access to an interior of the housing 106 and the various components, objects, devices, systems, etc. supported therein.

The water dispenser 102 can include a valve supported by the housing 106 that is designed to operate to open and close the water. For example, when the valve is open the water from the water source 1 can exit an opening of the water outlet 103 in the water dispenser 102 due to pressure from the water source 1. In one example, the valve can be manually opened by a lever, handle, foot peddle, etc. The valve can be fit into the water dispenser 102 such that the valve is integrated into the water dispenser 102, namely supported by the housing 106. The valve can be attached or coupled to the housing 106 using fasteners or other fittings. The water dispenser 102 can be connected to two water sources such as a hot water source and cold water source. The water dispenser 102 can include a valve for each water source. A manifold in the water dispenser 102 can mix hot and cold water to be dispensed simultaneously through the water outlet 103 in the water dispenser 102.

In one example, the housing 106 can include an actuator 104 supported by the housing 106. The valve can be operated by the actuator 104 such that the actuator 104 can open and close the valve. The water dispenser 102 may include one actuator for each valve in the water dispenser 102 such as one actuator for hot water and one actuator for cold water. The actuator 104 can be a solenoid or other type of actuator or actuating mechanism. The actuator 104 can be controlled by electrical signals and may draw power from a power source 114 supported by the housing 106 where the actuator 104 is electrically connected to the power source 114. The electrical signals can be sent to the actuator 104 by a timer 112 supported by the housing 112. The timer 112 can control the period of time that the actuator 104 opens the valve to release water.

The timer 112 can include electrical components such as a memory 123 and processor 125, or in another example the water dispenser 102 can further comprise a memory 123 and processor 125 in communication with the timer 112. The memory 123 and processor 125 can be used to store and process or execute one or more software or firmware programs related to or to facilitate a decontamination event. With the example of the timer 112 comprising the processor 125 and a non-transitory computer readable storage medium to store data, such as one or more software program, the timer 112 can store and execute one or more timer programs. The timer 112 can be enclosed in a water proof or water resistant enclosure 115 supported within the housing 106 of the water dispenser 102. In addition, electrical connections entering and exiting the timer 112 (such as those electrically connecting with the various sensors (touch or touchless), the manually actuated inputs, the light source(s), the agent dispensing system, and any other electronic components in the water dispenser 102 described herein) may be insulated wires where the entry and exit points of the enclosure for the housing may prevent water from entering the enclosure through use of materials such as rubber gaskets, plastics, glue, silicon, etc.

In one example, the water dispenser 102 can include one or more light sources, such as light source 108, that are supported by the housing 106, and that can be powered and electrically coupled to the power source 114. Using the light source 108 as an example, the light source 108 may be mounted to structures or structural components built or molded into the housing 106. In one aspect, the housing 106 may have a transparent region such as a window 109 built into the housing 106 such that the light source 108 can emit light through the transparent region. In another aspect, the housing 106 may have an opening for the light source 108 to emit light through. In still another aspect, the light source 108 may be removable or replaceable from the housing 106 or may be permanently coupled or mounted to the housing 106. The light source 108 may be positioned such that light emitted from the light source 108 source is emitted in accordance with a predetermined field of view, meaning that the light is emitted within a predetermined spatial distribution space or area. The field of view may define an inspection space in which the portion of the skin or covering of the skin of the individual can be positioned such that the light emitted from the light source 108 is incident upon or impinges upon the surface of the skin or covering of the skin of the individual. For example, the field of view may define a space between the water outlet 103 and a wash basin associated with the water dispenser 102. The field of view may also overlap an area of space in which water is dispensed from the water outlet 103 of the water dispenser 102.

In another example, the light source 108 can be mounted near the water outlet 103 of the water dispenser 102 and oriented such that water dispensed from the water outlet 103 is dispensed adjacent to or within the field of view of the light from the light source 108, which light can be emitted in accordance with a generally downward and outward distribution. This may be described as directing light emissions downward in the direction of the water discharge. However, it is contemplated that the light source 108 can be supported and positioned about or on the housing 106 of the water dispenser 102 or about or on any other structure in close proximity to the water dispenser 102 so as to emit light in any direction and in accordance with any field of view that is proximate the water dispenser 102 and that can be activated by an individual during a decontamination event.

The light source 108 can be any type of light emitting device such as an incandescent light bulb, a light emitting diode (LED), or other light source. The light source 108 may employ the use of fiber optic technology. A fiber optic cable may be placed internally within the housing 106 and/or the water dispenser 102 and directed to an originating light source either in the housing 106 or some other location as suits a particular purpose. The light source 108 may include more than one light source or more than one type of light source 108.

The light source 108 may emit light with a wavelength and intensity that causes a fluorescent agent to fluoresce or illuminate. In one example the light source 108 can be caused to emit light with a wavelength and intensity that causes a fluorescent agent to fluoresce or illuminate in a spectrum visible to the human eye. Depending upon the type of fluorescent agent, the light source 108 can be configured to emit light in one or more of several wavelengths or ranges of wavelengths to cause the fluorescent agent to fluoresce or illuminate. The fluorescent agent may also have properties that are cleansing to the skin or covering of the skin of an individual. Thus the fluorescent agent may be described as skin cleansing fluorescent agent. In one example, the light source 108 may be configured to emit an ultra violet (UV) light. The UV light may have a wavelength of about 150-400 nanometers (nms). The UV light may be ultraviolet A (UVA), ultraviolet B (UVB), ultraviolet C (UVC), or a combination thereof. UVA may be light that has a wavelength of about 400-315 nms. UVB may be light that has a wavelength of about 312-280 nms. UVC may be light that has a wavelength of about 280-100 nms. In another example, the light source 108 can be configured to emit light that has a wavelength in the visible spectrum of about 400-700 nms. In still another example, the light source 108 can be configured to emit light that has a wavelength in the infrared spectrum of about 700 nm to 1 millimeter. In one example, the light source 108 can be configured to emit light that provides a germicidal effect when incident upon the skin or a covering of the skin of the individual. The light source 108 may emit light in more than one of the described spectrums of light.

The fluorescent agent may be described as a fluorescent dye that illuminates when illuminated by light from a specific spectrum or light from a range of wavelengths. For example, the fluorescent agent can be compounds containing fluorophores, fluorescein, xanthene dyes, rhodamine dyes, stilbene dyes, functionalized polycyclic aromatic hydrocarbon dyes including lissamine flavine FF, pyranine, and/or amino G acid, triarylmethane dyes, methyl violet dyes, fuchsine dyes, phenol dyes, malachite green dyes, victoria blue dyes, diarylmethane dyes, and fluorescent fruit extracts including extracts from Viburnum trilobum, Ribes, and Ribes alpine. The fluorescent agent can be a combinations of the described compounds.

The fluorescent agent may be mixed or combined with a cleansing agent to form a composition. The composition may be dispensed via a composition dispenser or an agent dispenser. The composition dispenser may be a separate apparatus or device from the water dispenser 102. The composition dispenser may be located physically proximate to the water dispenser 102 and intended to be used by the individual in conjunction with the water dispenser 102 during a decontamination event. In one aspect, the composition of the fluorescent agent and the cleansing agent may be premixed and added to a chamber of the composition dispenser. In another aspect, the fluorescent agent may be housed or contained in a first chamber of the composition dispenser separate from a second chamber housing or containing the cleansing agent, wherein the fluorescent agent and the cleansing agent may be brought together and mixed (such as active mixing via a mixing mechanism or system within a mixing chamber or via passive mixing as both agents are dispensed). The composition can then be applied to the skin or covering of the skin of the individual as part of a decontamination procedure, such as to wash the individual's hands. When the composition, with its mixture of the fluorescent agent and the cleansing agent, is applied to the skin or the covering of the skin of the individual, the fluorescent agent can then be indicative of the spread or presence or location of the cleansing agent as applied to and about the skin or covering of the skin of the individual upon illuminating the fluorescent agent with the light from the light source 108 to cause the fluorescent agent to fluoresce. For example, if the fluorescent agent and the composition are properly mixed into the composition, then if the fluorescent agent is detected upon the skin of the individual the individual can be assured that the cleansing agent is also located on the same portions of the skin, and the individual can continue with the washing procedure, which includes at least some of the steps of wetting the skin or covering of the skin, applying the composition, washing or scrubbing, and rinsing to remove the composition.

The cleansing agent can be liquid soap, powdered soap, antibacterial soap, and antimicrobial soap. The cleansing agent can also be chlorhexidine gluconate (clear/pink solution); iodine based preparations (brown); and aqueous alcoholic solutions (clear). The cleansing agent can also be a combination of the compounds described herein. In one example, the cleansing agent is a waterless sanitizing compound such as an alcohol based compound.

In one aspect of the technology, the height of the water outlet 103 can be placed so as to minimize inadvertent exposure of light to the eyes of the person. In this manner, visual inspection of the skin is optimized. The individual performing the decontamination event views the skin from a position above the light source 108 to optimize decontamination and removal of any residual fluorescent agent. While reference is made herein to removal of the fluorescent agent from the skin of the individual, it is important to note that the fluorescent agent present in the composition is intended to act as a surrogate measure of removal of other contaminants that may be present on the skin of the individual by removal of the cleansing agent of the composition.

In one example, the light source 108 can be controlled by the timer 112. For example, the timer 112 may be electrically connected to the light source 108 such that timer 112 can activate the light source 108 to emit light in the field of view. The timer 112 may be capable controlling the light source 108 to emit light from different wavelengths at different times. For example, the light source 108 may comprise two different types of light emitting devices that emit light in different ranges of wavelengths of light and the timer 112 can selectively turn on one or both of the light emitting devices for any duration of time. In one example, a different amount of power applied to the light source 108 may change the wavelength and/or intensity of light that is emitted by the light source and the amount of power applied to the light source 108 may be controlled by the timer 112.

The timer 112 may be capable of activating the actuator 104 and activating the light source 108 according to one or more timer programs. The timer program may be a sequence of time periods in which the actuator 104 is activated to dispense water and the light source 108 is activate to emit light, and where the timer program operates to coordinate these throughout and to define the sequences and parameters of the decontamination event. The light may be emitted simultaneous to the water being dispensed, either for at least some overlapping duration of time or for the complete duration of time, or the light may be emitted and the water may be dispensed during different time periods. The timer program can coordinate the activation of the water and the light, meaning that the water and the light are turned on during a decontamination event at select and specific times, either in isolation (i.e., separate from one another) or simultaneous with one another for at least some duration of time, to facilitate the decontamination event, including facilitating the assessment of the effectiveness of the decontamination event. For example, a first timer program may actuate water for a first predetermined period of time. This first predetermined period of time allows an individual to wet or rinse the portion of the skin or the covering of the skin of the individual to be decontaminated, such as the hands of the individual, as part of the decontamination procedure, after which the composition can be dispensed and applied to the portion of the skin or the covering of the skin of the individual to be decontaminated, also as part of the decontamination procedure. After the first predetermined period of time the light may be activated to emit the light onto the portion of the skin or covering of skin of the individual to be decontaminated for a second predetermined period of time. This second predetermined period of time allows the individual to lather the composition, scrub and work the composition about the portion of the skin or the covering of the skin of the individual to be decontaminated, also as part of the decontamination procedure. The light will cause the fluorescent agent in the composition to fluoresce, thus visually demonstrating to the individual the areas of the skin that have been covered with the composition including the cleansing agent. Particularly, the individual may use the second predetermined period of time to ensure that the composition has completely covered the portion of the skin or covering of the skin to be decontaminated. The first timer program may then activate both the water and the light simultaneously for a third predetermined period of time. This third predetermined period of time may be used by the individual to remove, or in other words to wash or rinse off, the composition from the portion of the skin or covering of the skin of the individual to be decontaminated, again, also as part of the decontamination event. Alternatively, the first timer program may then activate the water only for a portion of the third period of time, and the light subsequent to that for a portion of the third period of time. If any residual fluorescent agent remains (by being detected due to its fluorescence), then the light and water can be again activated for a fourth and fifth period of time, respectively.

Each of the first, second or third predetermined periods of time may be for any length of time. For example, the second predetermined period of time may be 30 seconds thus allowing the individual to scrub their hands for 30 seconds with the composition that includes the cleansing agent. In addition, the third period of time may be for 30 seconds to encourage the individual to adequately rinse and remove the composition from the skin or covering of the skin. Such time periods can be beneficial or advantageous for a variety of reasons, including the training of different individuals on proper washing or decontamination techniques known to optimize the effectiveness of a decontamination procedure.

A sensor associated with the water dispenser 102 may be employed to detect if any residual fluorescent agent is still on the skin or covering of the skin of the individual following the rinsing and removal of the composition during the third predetermined period of time as will be described in greater detail below.

Other timer programs different from the one described above can be made available via the water dispenser 102, and as such, the first timer program described above is not intended to be limited in any way. Indeed, the timer 112 may be capable of executing more than one timer program, each configured to coordinate the activation of the water and the light in accordance with predetermined time periods (as well as to strategically deactivate these for a duration of time if desired) that are different from other timer programs. For example, a second timer program may be configured to activate the actuator 104 to dispense the water without simultaneously activating the light source 108. A third timer program may be configured to activate the light source 108 without simultaneously activating the actuator 104 to dispense water. Many other timer programs may be employed to alternatingly or simultaneously activate the light and the water for any predetermined periods of time and for any number of time periods, as well as to deactivate either of these for a period of time during a decontamination event (e.g., to preserve water while the individual is scrubbing).

The timer 112 with the timer programs may be user adjustable. For example, a user may access the timer 112 via a data connection 111 supported in the housing 106. The data connection 111 may be a universal serial bus (USB) port, a serial port, or other type of wired connection. The data connection 111 may be a wireless connection that employs transmitting and receiving hardware for radio communications as wells as protocols such as WiFi, Bluetooth, Near-Field Communications, Zigbee, etc used for computer networking. In one example, the data connection 111 can comprise a card reader slot such as Secure Digital (SD), micro SD or other type of memory card slot. The data connection 111 may have a combination of the connections and ports described herein and may be both wired and wireless. Physical openings of the data connection 111 in the housing 106 may be protected from water intruding into the data connection 111. For example, a USB port may be covered with a material such as rubber than provides a tight seal thus preventing water from the water dispenser 102 from intruding into the data connection 111. A user may access the data connection 111 to adjust, create, modify, delete, add, or otherwise operate upon the timer programs of the timer 112. For example, the length of time of the predetermined periods of time for the timer programs can be lengthened or shortened. Predetermined periods of time for a timer program can be added to activate the light, the water, or both. How timer programs are activated can also be user adjustable via the data connection 111. The data connection 111 may also be used to change an intensity of light or a wavelength of light emitted by the light source 108, or to activate/deactivate different light sources, if available. In essence, the data connection 111 can be accessed to alter, customize, or otherwise configure the electronic systems of the water dispenser 102, including, but not limited to, the timer 112 and the timer programs to meet a particular application, the light source(s), the water and composition dispensing systems, and others to facilitate a particular decontamination procedure. For example, the timer and timer program(s) used in a residential setting for private use or in a commercial setting for public use will be different than the timer program(s) used in a hospital setting to facilitate a specific and strict decontamination procedure in preparation for a surgical or other procedure, and the data connection 111 can be accessed to facilitate this. The data connection 111 can further be accessed to transmit, receive, download or otherwise transfer data from the water dispenser to a computer or a computer network. Customization of a timer program may be performed by an individual user or by an organization associated with the timer program. For example, a hospital may own products that employ the technology described herein that use timer programs. The hospital as an organization may customize the timer programs and may not provide access to the personnel using the timer programs. Thus, the personnel using the timer programs may not be able to alter the timer programs and the hospital may thus ensure that the personnel are using the timer programs customized or selected by the hospital in accordance with established procedures or protocols.

In one example, the timer programs can be activated via a first sensor 110. The first sensor 110 can be supported by, housed by or otherwise coupled to the housing 106. The first sensor 110 may be powered by the power source 114. The first sensor 110 may be electrically connected to and in communication with the timer 112. The first sensor 110 may be referred to as a touchless sensor and can detect the presence or absence of a portion of the individual. The first sensor 110 or the second sensor 116 can be an optical sensor, an infrared sensor, a motion sensor, a temperature sensor, a light intensity sensor, an ultrasonic proximity sensor, a LIDAR sensor, an inductive proximity sensor, an eddy current proximity sensor, a magnetic proximity sensor, or any other type of sensor than can detect a portion of a person. Alternatively, the first sensor 110 or the second sensor 116 can be an electric eye which is made up of a light source and an intensity detector. A hand or other body part of the user can interrupts the light beam associated with the electric eye thereby creating detection of a user and initiating a timer program. An opening in the housing 106 can allow the first sensor 110 to detect motion or the presence or absence of the individual. The first sensor 110 can be a replaceable component of the water dispenser 102. The first sensor 110 may be attached or coupled to the housing 106 using fasteners or other mounting systems.

In one example, the first sensor 110 is a multipurpose sensor that is capable of detecting different movements of the individual and responding differently to the different movements in conjunction with the timer 112, namely to activate different timer programs. For example, a first movement detected by the first sensor 110 may activate the first timer program, a second and different type of movement detected may activate the second timer program, a third and still different type of movement detected may activate the third timer program, and so forth for as many timer programs needed or desired. The movements of the individual that can be detected by the first sensor 110 may be varied and may be user adjustable via the data connection 111. For example, movements can be added, modified, or deleted. To select and activate one of a plurality of timer programs, example movements can include a swipe of a body part past the first sensor 110, such as a hand of the individual moving through the field of view of the first sensor 110 a set number of times or within a range of speeds. The number of swipes in a given time period may trigger different timer programs. The number of swipes that are performed in a given time period may be described as a swipe frequency. For example, one swipe in a 2 second period may trigger a first timer program where two swipes in a 2 second period may trigger a second timer program. A movement over the sensor may be described as a swipe or a wave. As an alternative to a swipe or wave, a hand or body part may be placed over the sensor for a given period of time that is longer than a swipe or wave. By covering the sensor for a period of time longer than a swipe or wave, a user may activate a different timer program than a swipe or a wave. The period of time longer than a swipe or a wave may be 1 or 2 seconds. A display, such as display 119, may output information regarding which timer program has been selected based on a swipe frequency, a duration of covering the sensor, or other gesture as described below. By combining a swipe frequency, a duration of covering the sensor, or other gesture with the output on the display 119, a user may toggle through timer program options to select and initiate a timer program.

Alternatively, different hand gestures/movements or gestures/movements of other body parts may trigger different timer programs. A gesture may include moving a body part such as a hand in a predetermined pattern such as a circle, swiping horizontal, swiping vertically, and others. In one embodiment, gestures or movements are recorded by a camera or imaging system such as an image capturing system 118. A gesture may be a user holding up a specific number of fingers. For example, the user may hold up one finger and the image capturing system 118 captures an image of the hand holding up one finger, the image is analyzed, and a timer program corresponding to the image of a hand holding up one finger is initiated. A hand holding up two fingers or one finger and a thumb may correspond to a different timer program. Any number of hand gestures or finger signaling may be employed to correspond to unique timer programs as will be recognized by those skilled in the art, and thus those specifically described herein are not intended to be limiting in any way.

As alternative, or in addition to the first sensor 110 and the second sensor 116, a device 152 associated with a user may be used to identify a user or person and trigger a timer program. For example, the device 152 may be a bracelet or other object employed by a user that interacts with the first sensor 110 to trigger the timer program. The bracelet may include a ferromagnetic material that interacts with the first sensor 110 when in proximity to the first sensor 110. The device 152 or other object may also include external information or indicia, such as a picture of the user, the name of the user, an employee identification number, etc. Other devices may also be employed to interact with the first sensor 110 and trigger the timer program. The device 152 may be a radio frequency identification (RFID) tag. The device 152 may be a mobile device, such as a smart phone (or smart watch or any other smart mobile device), that may also be employed to identify a person and may trigger a timer program. The device 152 an be used for identification purposed to identify the user associated with the device and can then be paired with any information gathered during the decontamination procedure where the information is stored associated with the user's identity. The smart phone or other smart mobile device may communicate using WiFi, Bluetooth, near field communication, RFID, cellular networks, or other wireless protocols. A timer program triggered by a device that is unique to a user may trigger a timer program that is customized or unique to the user.

In still other examples, the water dispenser 102 can comprise a number of manually activated timer programs, where an individual is able to select a timer program by manually interfacing with one of a plurality of electronic inputs 117 on an input panel 113 of the water dispenser 102, wherein each of the electronic inputs 117 is associated with the timer 112 and a respective timer program. Indeed, the manually actuated electronic inputs 117 can be in electrical communication 121 with the timer 112 to facilitate activation of the associated timer programs. For example, the water dispenser 102 can comprise a plurality of user selectable electronic inputs 117 (e.g., buttons 1-3) that are each associated with one of a plurality of different timer programs. The manually actuated electronic inputs 117 can comprise any type of input device or system, such as depressible buttons, selections on a touch screen, and any others as will be recognized by those skilled in the art. The input panel can include a display 119 capable of outputting information regarding the timer programs. For example, display 119 may be a screen that displays numbers or text indicating which timer program has been selected. The display 119 may be one or more lights that indicate which timer program has been selected. The lights may have text, numbers or symbols printed next to the lights. The lights may be different colors where each color indicates a different timer program. The display 119 may also be used to interface with the individual to adjust or modify the timer programs.

In one example, the housing 106 may support a second sensor 116. The second sensor 116 may have all of the same features and capabilities as those described for the first sensor 110. The second sensor 116 may be placed in the housing 106 in addition to the first sensor 110. The first sensor 110 may have a field of view that is in a different orientation than a field of view of the second sensor 116. For example, the field of view of the first sensor 110 may point in an opposite direction of the field of view of the second sensor 116. In one example, both the first sensor 110 and the second sensor 116 can each be employed by the timer 112 and the individual to activate a different timer program. For example, the individual may perform a movement such as a swipe in the field of view of the first sensor 110 to activate a first timer program and then perform a second movement in the field of view of the second sensor 116 to activate a second timer program. Thus each sensor can correspond to a different timer program. It should be appreciated that the housing 106 can support any number of sensors to be associated with or correspond to any number of timers and associated timer programs. Signs or other directions can be mounted on or near the water dispenser 102 with indicia, such as written instructions or figure depictions, or some combination of these, which instruct or teach or direct the user to know which movements and which sensors will activate which timer programs. Alternatively, the first sensor 110 can be configured to operate the water dispenser 102 in a normal, untimed manner, with the second sensor 116 operating to activate the timer and one or more associated timer programs.

The power source 114 can be any number or type of power sources used to power the various electronic components of the water dispenser 102, such as the light source 108, the actuator 104, the timer 112, any sensors, such as first and second sensors 110 and 116. The power source 114 can be a replaceable battery, a rechargeable battery, an inductively transferred power source, an alternating current power source, or others, or a combination of these. The power source 114 can be self-contained in the housing such as a battery or could be connected to an exterior power source such as a wall outlet to access alternating current. A battery can be charged using a wired connection or can be charged wirelessly using inductive technology. The power source 114 can have a notification system that notifies a user of a low battery. For example, a red light supported in the housing may activate to notify a user that the batter is low and should be recharged. The notification system may be part of an alert system 126. Alternatively, the power source 114 may notify the user of a low battery wirelessly via the data connection 111 such that the notification may be received by an electronic device remote to the water dispenser 102.

In one example, the power source 114 can comprise a power generator 122 and a battery associated with the power generator 122, wherein the power generator 122 can be configured to be capable of generating power and storing the power in the battery. The power generator 122 may comprise an impeller that when turned or rotated will generate electricity, such as to charge the battery. For example, the impeller may be part of a turbine with blades that are turned by a fluid such as water. In one example, the power generator 122 can be supported in the housing 106. Alternatively, the power generator 122 may be exterior or remote to the housing 106 of the water dispenser 102. In each of these scenarios, the impeller of the power generator 122 may be supported or situated in line with and turned by the flow of the water from the water supply line 3 to the water dispenser 102. For example, the water supply line 3 may be connected to the power generator 122 and water to be dispensed through the water outlet 103 can first be caused to pass through the power generator 122 to act upon and turn the impeller. Thus whenever water is dispensed by the water dispenser 102, the impeller of the power generator 122 is turned or rotated and electricity generated, which in one example, can be caused to be stored in the one or more batteries to power the various electrical components of the water dispenser 102.

The water dispenser 102 can further include an image capturing system 118 supported by the housing 106. The image capturing system 118 may include a camera or other imaging device such as a charge-coupled device (CCD), a complementary metal-oxide-semiconductor (CMOS), or digital camera. The image capturing system 118 may have other electronic components such as a processor, memory, storage device, wired or wireless components that enable network access, etc. The image capturing system 118 may share components for operations with the timer 112 and the data connection 111. The image capturing system 118 may have removable storage that stores images captured by the image capturing system 118. The image capturing system 118 may be removable or replaceable in the housing 106. The housing 106 may have an opening or a transparent window for the image capturing system 118 to facilitate a field of view of the image capturing system 118. The image capturing system 118 may, in some instances, comprise and utilize a lens. The image capturing system 118 can be configured to capture images in the field of view of the image capturing system 118. The images may be still pictures or video. The images may be of a portion of the individual during a decontamination event. For example, the image capturing system 118 can record the hands of an individual while the hands are being decontaminated. The image capturing system 118 may be controlled by the timer 112 such that the image capturing system 118 may record images during a timer program. The image capturing system 118 may be electrically connected to and in communication with the timer 112 and the data connection 111. The image capturing system 118 may be powered by the power source 114. The image capturing system 118 can store the captured images in a memory associated with the image capturing system 118, the data connection 111, or the timer 112, or a network database. The image from the image capturing system 118 can be accessed via the data connection 111. For example, an electronic device such as a computing system that is networked to the data connection 111 can access the images. In one example, images captured by the image capturing system 118 are sent via the data connection 111 over a network to a database such as database 410 of FIG. 4.

The water dispenser 102 can further include an identification system 127 supported housing 106 and associated with the memory 123 and processor 125 to identify the individual initiating the decontamination event. In one example, the image capturing system 118 is employed by the identification system 127 and is capable of identifying an individual during or prior to a decontamination event that employs the water dispenser 102. For example, the image capturing system 118 can capture an image of an identification tag worn or otherwise carried by the individual, such as the device 152, where the identification tag possesses or facilitates access to personal identification indicia that is associated with the individual. The personal identification indicia can be encoded in or made accessible via at least one of a barcode, a quick response (QR) code, or text that is recognized via optical character recognition. A radio frequency identification (RFID) tag can also be employed to identify the individual. This RFID tag can be identified using components of the image capturing system 118 or the data connection 111. The device 152, such as a smart phone, can also be used to identify the individual in conjunction with the identification system 127. For example, the device 152 can be a smart phone in communication with the data connection 111 using wireless protocols. The device 152 may have an RFID tag. The image capturing system 118 may be in communication with or operable with a computer system to identify the individual. For example, the personal identification indicia captured by the image capturing system 118 can be sent to the computer system via the data connection 111. The computer system can the perform steps to look up the personal identification information associated with the personal identification indicia in a database to identify or recognize the individual. The database may include profile information for a plurality of individuals that are associated with unique identifiers (e.g. the identification tag). The identification can then be sent back the image capturing system 118 such that any images captured of the individual during a current decontamination event can be stored with metadata associating the images with the individual's identity. Thus, the present technology can be employed by the individual or by others to demonstrate that the individual properly executed a decontamination procedure. For example, a surgeon prior to surgery may employ the present technology to decontaminate the hands of the surgeon. During the decontamination or scrubbing, images or video are captured of the surgeon's hands. Subsequent to the surgery if there are complications, such as infections, the surgeon can use the images to prove that the surgeon properly decontaminated or scrubbed the hands of the surgeon prior to the surgery. Additionally, the identification of the individual and the images of the decontamination event can be used to ensure that individuals comply with decontamination policies of an institution. The image capturing system 118 can further be configured to capture and store, as part of an individual's personal profile, a plurality of decontamination events as captured over time. The historical data that is collected from each decontamination event can be used for a variety of purposes. For example, such historical data can be used to customize a decontamination procedure that is optimized specifically for that individual. In another example, the historical data obtained from a plurality of decontamination events for one individual can be compared to the historical data obtained from a plurality of decontamination events of one or more other individuals.

The water dispenser 102 can further comprise, and the housing 106 can further support, a fingerprint scanner 128. The fingerprint scanner 128 can receive fingerprint data from an individual when a finger or digit of the individual is pressed against a sensor of the fingerprint scanner 128. Fingerprint data for individuals can be stored in a database, such as database 410 of FIG. 4 or another database, and used to identify the individual during or prior to a decontamination event. The database may be stored locally in the components of the water dispenser 102 or remotely. The identification made using the fingerprint data captured by the fingerprint scanner 128 can be used to store images captured by the image capturing system 118 and associate these with the identification of the individual.

In one example, the image capturing system 118 is capable of capturing an image and analyzing the image to detect the presence of the fluorescent agent on the skin or covering of the skin of the individual. For example, image recognition technology may be employed to detect colors or wavelengths of light that are emitted by the fluorescent agent while the light source 108 is emitting light to illuminate the fluorescent agent to cause it to fluoresce. The images may be analyzed by components of the image capturing system 118 or the images may be sent to a remote computer system to detect the fluorescent agent with results being sent back to the image capturing system 118 or another component of the water dispenser 102. Thus the image capturing system 118 may be a sensor that is capable of detecting the fluorescent agent. The detection of the presence of the fluorescent agent may be communicated to the individual during the decontamination procedure. This may be accomplished using the alert system 126. The presence of the fluorescent agent on the portion of the skin or covering of the skin of the individual may be indicative that a portion of the composition, and thus a portion of the cleansing agent, remains on the skin of the individual, which can indicate that an adequate and complete decontamination of the skin or covering of the skin has not taken place, depending upon the amount of trace fluorescent agent remaining and the predetermined acceptable threshold level required to effectuate a successful decontamination event. The individual may use this information to repeat rinsing of the skin until no traces of the fluorescent agent are detected, or at least until an acceptable amount of trace fluorescent agent remains. Indeed, it may not be necessary to remove 100 percent of the fluorescent agent (and thus the cleansing agent) to achieve a satisfactory decontamination event. In one example, images from the image capturing system 118 may be analyzed to detect any amount and/or intensity of the fluorescent agent that remains upon the skin or covering of the skin of the individual. If the intensity or amount of the fluorescent agent detected is above a predetermined level, then the user may be notified.

For example, an emissions frequency of the cleansing agent may be known and used to detect any fluorescent agent. In one example, an overall image intensity could be measured, since regardless of the emission frequency, the intensity of the light being received by the image capturing system 118 would increase substantially as more area being decontaminated is covered with the fluorescent agent. In one example, the full color spectrum of the image can be processed, and one or more specific frequencies, or one or more frequency ranges, can be used to create a relative measurement, i.e., before, middle, and after. This latter method would be more precise, since it would be selective to the emission frequency of the cleansing agent. Another method would be to impose a digital notch filter that inherently makes the image capturing system 118 selectively sensitive to the one or more specific frequencies, or one or more frequency ranges.

Other optical sensors besides the image capturing system 118 may be supported by the housing and employed to detect the fluorescent agent on the skin or covering of the skin of the individual, such as. For example, a light intensity sensor may be employed. The light intensity sensor may sense more or fewer photons in the light emission range, or ranges, of interest that correspond to the cleansing agent and/or the fluorescent agent. The light intensity sensor could be sensitive to the whole visual spectrum. The light intensity sensor may be described as a fluorescent emission intensity sensor. Other optical sensors or light intensity sensors may be described as a broad class of devices are called photodetectors including photodiodes and photo transistors. A sensor belonging to the class of photo detectors may use the photoelectric effect to convert photon input into electrical signal output data. Digital cameras (include CCDs, CMOSs, etc.) and solar panels are two examples where the number of photons received is in some way proportional to the strength of the signal generated. These devices demonstrate a light intensity measurement device.

In one example, the image capturing system 118 may be employed to generate a score based on results of the decontamination event. For example, images of the decontamination event may be analyzed by the image capturing system 118 or a remote computer system to make determinations regarding the decontamination event. The analysis may determine a percentage of coverage of the cleansing agent and the fluorescent agent over the portion of the skin of the individual. The analysis may determine if any fluorescent agent remains detected on the skin of the individual after the decontamination event is complete and the intensity level or amount of the remaining fluorescent agent. As such, one aspect of a timer program can be an assessment period where the individual places the just decontaminated portion of the skin or covering of the skin within the field of view of an optical sensor of the image capturing system 118 that activates for a predetermined duration of time to capture one or more images that can then be analyzed to determine the score in accordance with predetermined parameters pertaining to the scoring of decontamination events. Different results of the analysis may be used as weighted factors in generating a score such as a numerical score to grade the effectiveness of the decontamination event. The results or the score may be stored in a database on or remote to the water dispenser 102, such as database 410 of FIG. 4 or another database. The results or the score may or may not be communicated to the user.

In one example, the image capturing system 118 can be used as the first sensor 110 or the second sensor 116. The image capturing system 118 can comprise an optical sensor that is capable of recognizing a current movement of the individual to trigger an associated timer program and the coordinated activation of the light and water for facilitating the decontamination event. Alternatively, such movements can be used to activate the light source, the dispensing of the water or the dispensing of the composition not in accordance with a timer program. Upon the optical sensor sensing a current movement of the individual, the image capturing system 118 further operates to compare this with a plurality of stored predetermined acceptable movements. The image capturing system 118 can utilize a matching program or algorithm to match the current movement with a stored movement. Upon determining a match, the image capturing system 118, which can be in communication with the timer 112, can initiate a timer program (or the activation of the light source, the water dispenser, or an agent dispensing system as discussed below) associated with and based on the sensed and matched movement. As described above, various swipes, durations of time covering the sensor, and gestures may be employed to initiate or trigger a specific timer program.

As mentioned, the water dispenser 102 can further comprise an alert system 126. The alert system 126 may further comprise a notification device 124. The alert system 126 and the notification device 124 may be supported by the housing 106. The alert system 126 and the notification device 124 may be powered by the power source 114. The alert system 126 may be in communication and coordinated with the timer 112 to time one or more aspects of the decontamination event or portions of the decontamination event, such as the various time periods of one or more timer programs, the decontamination procedure, or the decontamination event in general, as well as to notify the individual of certain things, such as low batteries, errors or malfunctions, and other things. For instance, the notification device 124 may provide feedback to a user regarding an initiation of a timed aspect, an amount of time that has elapsed for a timed aspect, and/or a termination of a timed aspect of the decontamination event. The feedback may be visual, auditory, and/or haptic feedback. In one aspect, the notification device 124 may have a plurality of notification lights configured to progressively change status from an initiation of a timed aspect (e.g., a timed decontamination procedure) to the end of the timed aspect, as coordinated with the timer program. The lights may progressively light up during the timed aspect of the decontamination event, or they may initially start emitting light and then progressively turn off. Alternatively, the notification device 124 can comprises a display that numerically counts time intervals until the expiration of the duration of time of the timed aspect. The alert system 126 can be configured to count up or count down. For example, during a timer program, the notification device 124 and the alert system 126 may provide feedback to the individual for each of the predetermined periods of time. In another example, the alert system 126 can comprise a timer independent of the timer 112.

Figure 1G:
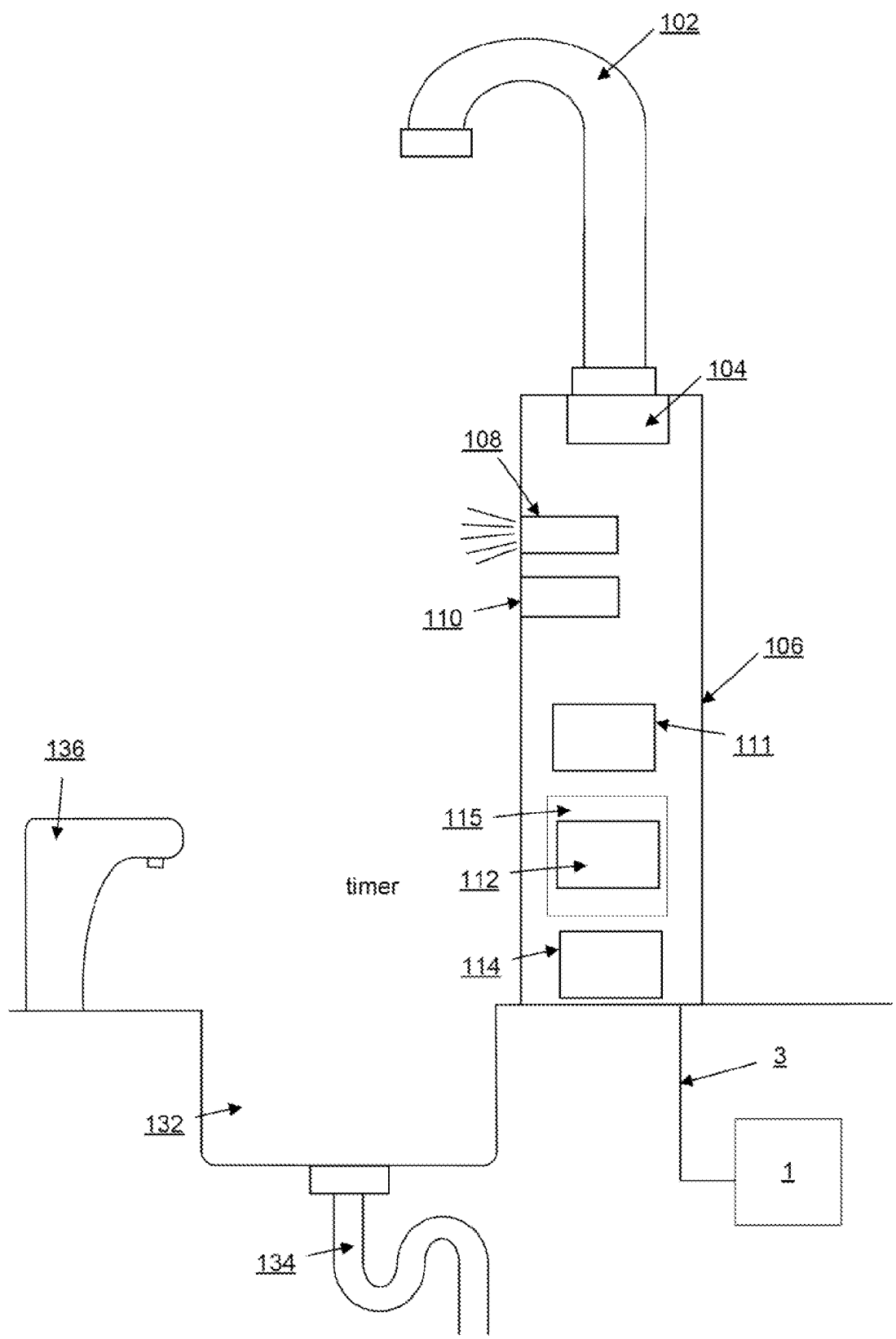

FIG. 1G depicts a system for facilitating effective decontamination of a portion of at least one of skin or a covering of the skin of an individual as part of a decontamination event, including assessing the effectiveness of the decontamination event. The system can include a wash basin 132. The wash basin 132 may also be referred to as a sink. The wash basin 132 may be configured and utilized to capture water that is dispensed by the water dispenser 102 and any composition used during the decontamination event, and then to drain the water and the composition through the drain 134 to a managed utilities system. The system can further comprise the water dispenser 102, which may be mounted or otherwise coupled to a surface of the wash basin 132, to a counter or wall proximate the wash basin 132, or to any other structure proximate the wash basin 132. The system can further comprise the light source 108. The field of view of the light source 108 may be positioned so as to facilitate the emission of light onto the skin or covering of the skin of the individual during the decontamination event. In one aspect, the field of view can be positioned so as to be between a water outlet 103 of the water dispenser 102 and the wash basin 132, but this is not intended to be limiting in any way. The system can further comprise a composition dispenser 136, which may be located proximate to the water dispenser 102 and the wash basin 132. The composition dispenser 136 may include an outlet for dispensing a composition with the fluorescent agent and the cleansing agent. The composition dispenser 136 may be positioned such that composition dispensed from the outlet will fall into the wash basin 132 if not intercepted by a portion of the skin or covering of the skin of the individual to be decontaminated. The composition dispenser 136 may be mounted to a structure or may be freestanding. The composition may be premixed and stored in a chamber of the composition dispenser 136. Alternatively, the fluorescent agent may be stored in a first chamber of the composition dispenser 136 and the cleansing agent may be stored in a second chamber of the composition dispenser 136 and a mixing mechanism may be employed to mix the cleansing agent with the fluorescent agent prior to or upon dispensing of the composition. The composition dispenser 136 may comprise a pump that is manually activated by the individual or may be activated using a touch or touchless sensor and an actuator.

With reference to FIGS. 2A-I, set forth is a water dispenser 202 in accordance with another example of the present disclosure. It should be appreciated that the water dispenser 202 can have all of the same features and capabilities as those described above as pertaining to the water dispenser 102 of FIGS. 1A-G. The water dispenser 202 can be adapted to communicate water from a water source to the skin or a covering of the skin of an individual. Water may be dispensed through a water outlet 203 that travels through a water conduit 205 in the water dispenser 202 (e.g., the water conduit 205 can be routed through a neck of the water dispenser 202). The water dispenser 202 can comprise a housing 204 that is the outer enclosure of the water dispenser 202 and houses the base and the neck of the water dispenser 202 as well as any other components such as sensors or handles.

Figure 2A:
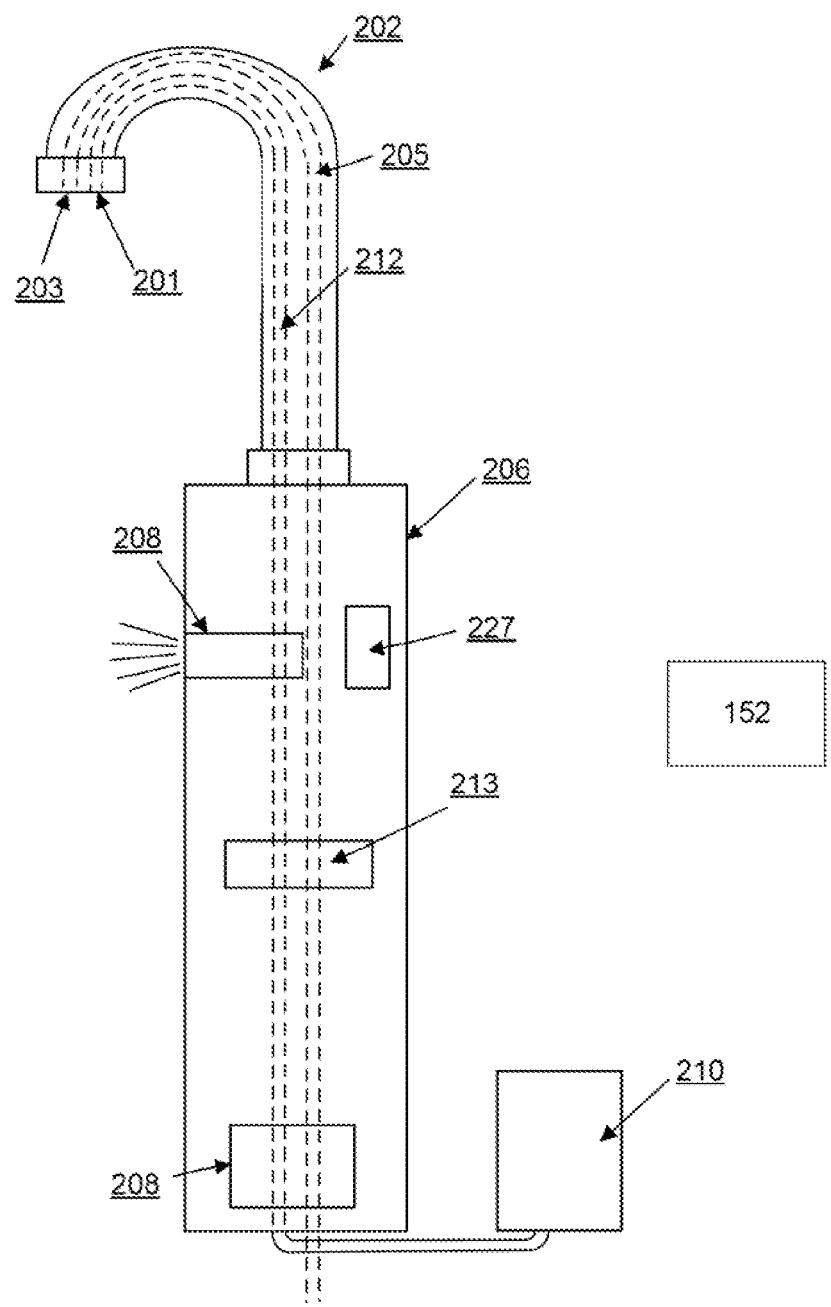
FIGS. 2A-I are block diagrams of water dispensers and systems with a light source for facilitating assessing the effectiveness of a decontamination event to decontaminate a portion of at least one of skin or a covering of the skin of an individual in accordance with aspects of the technology.
Figure 2B:
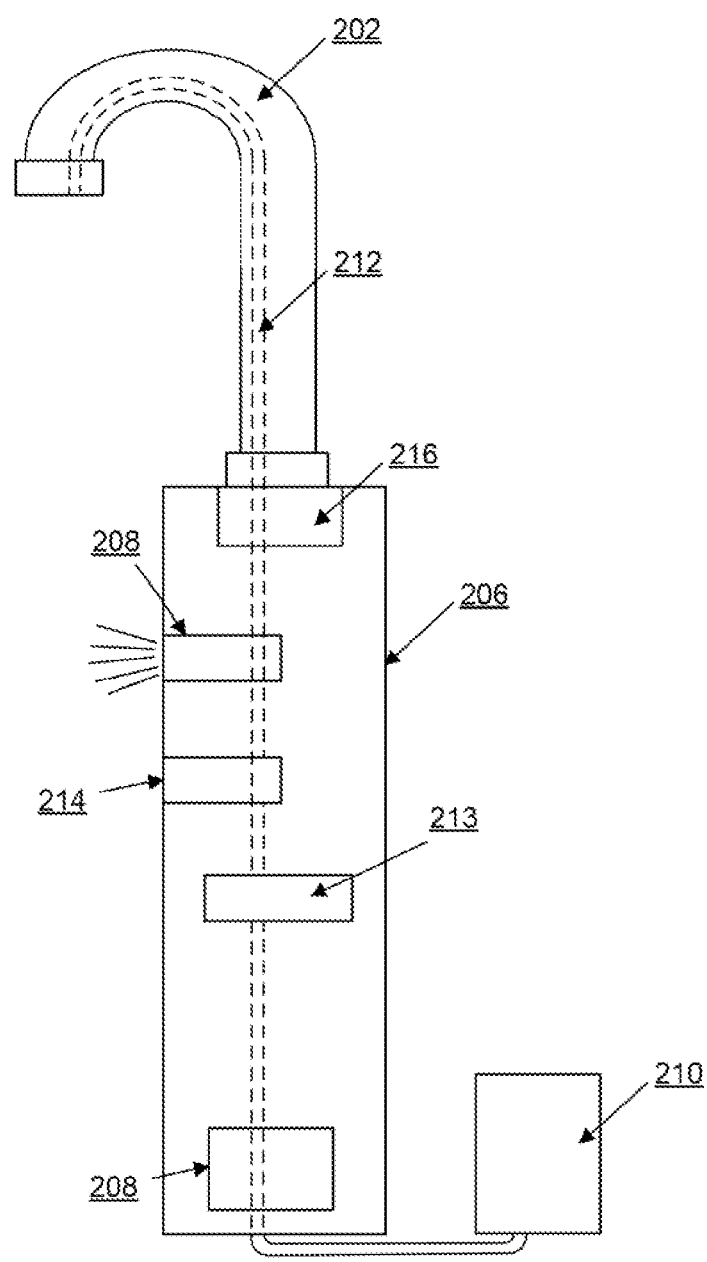
Figure 2C:
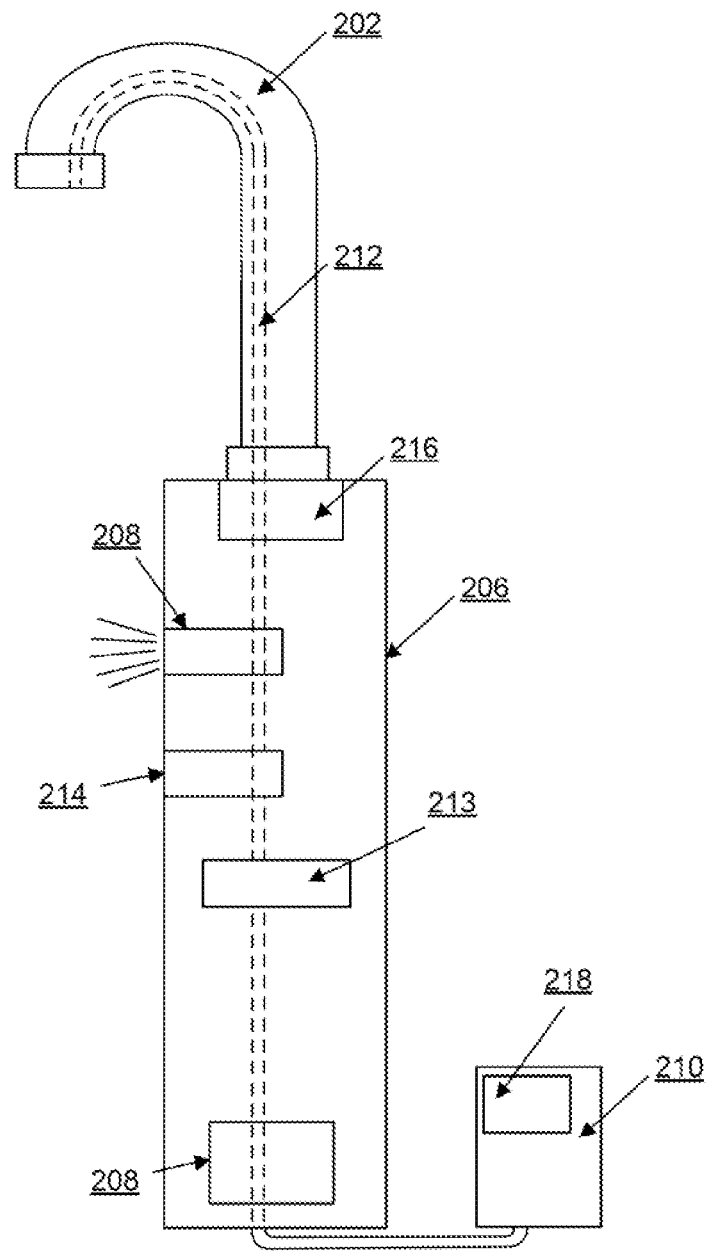
Figure 2D:
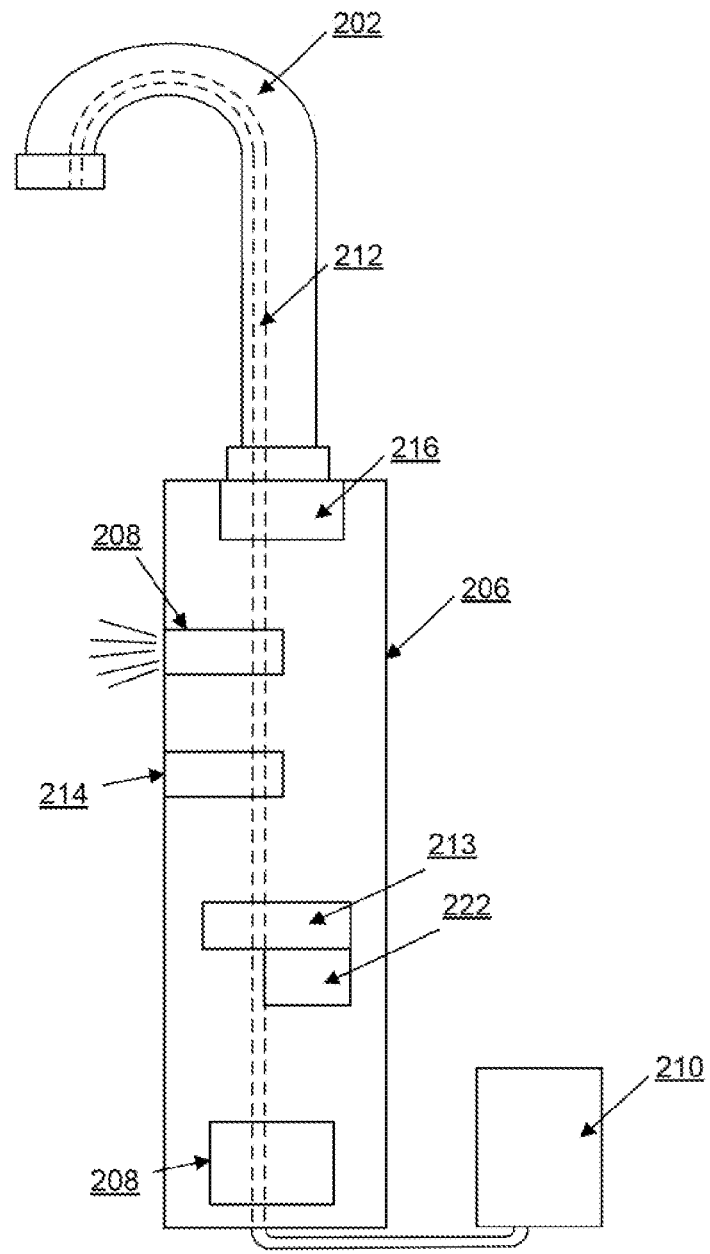
Figure 2E:
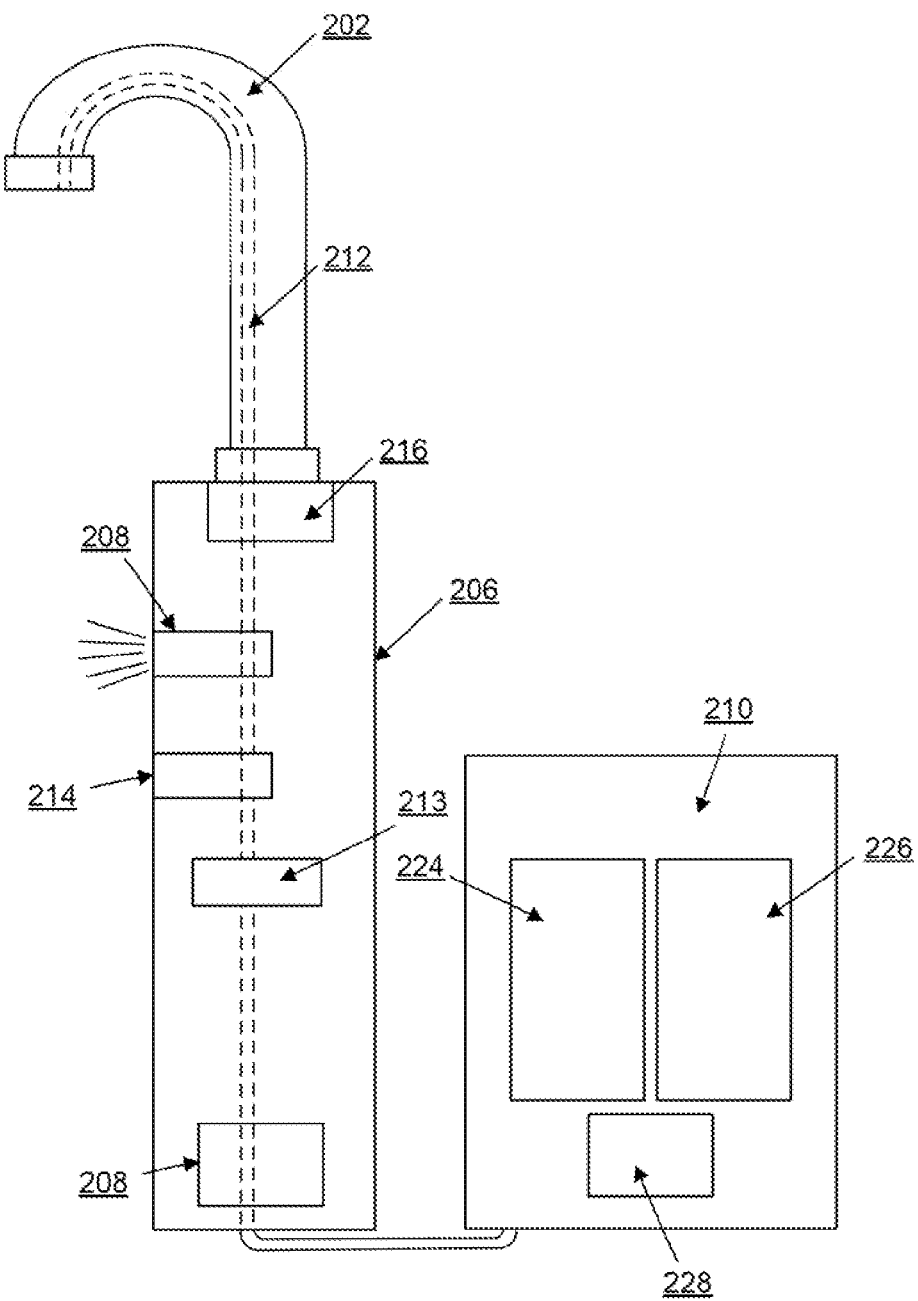
Figure 2F:
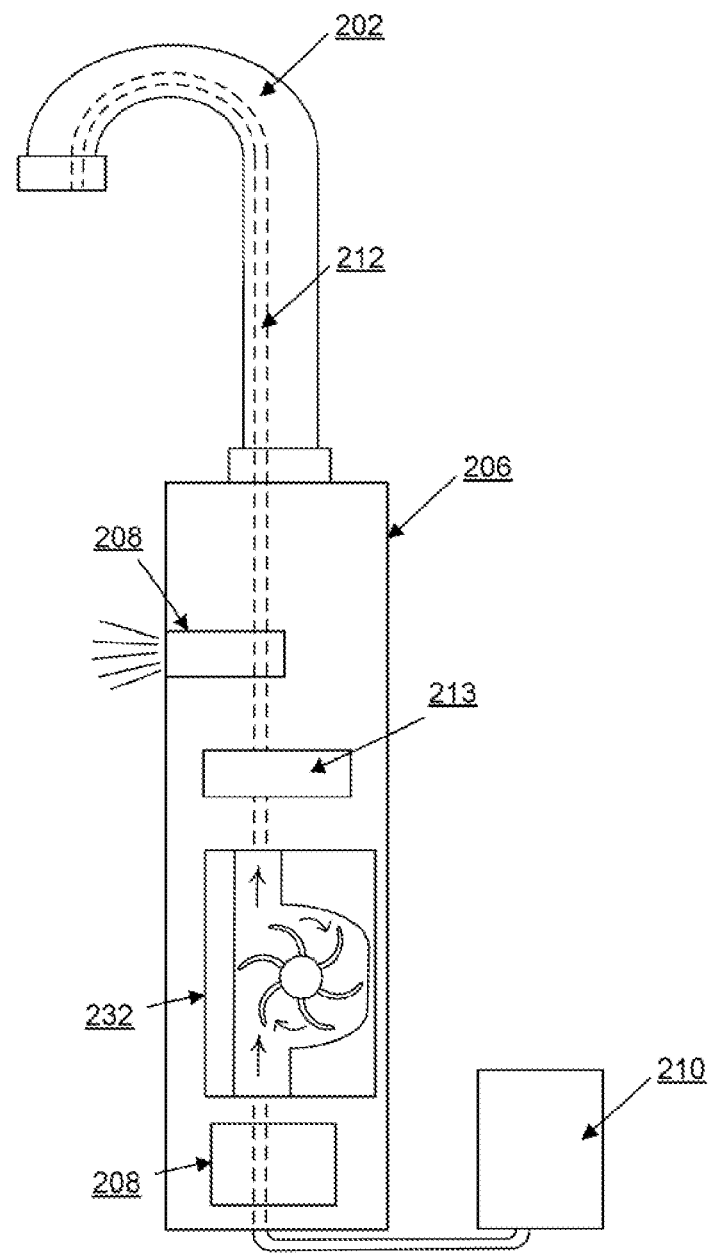
Figure 2G:
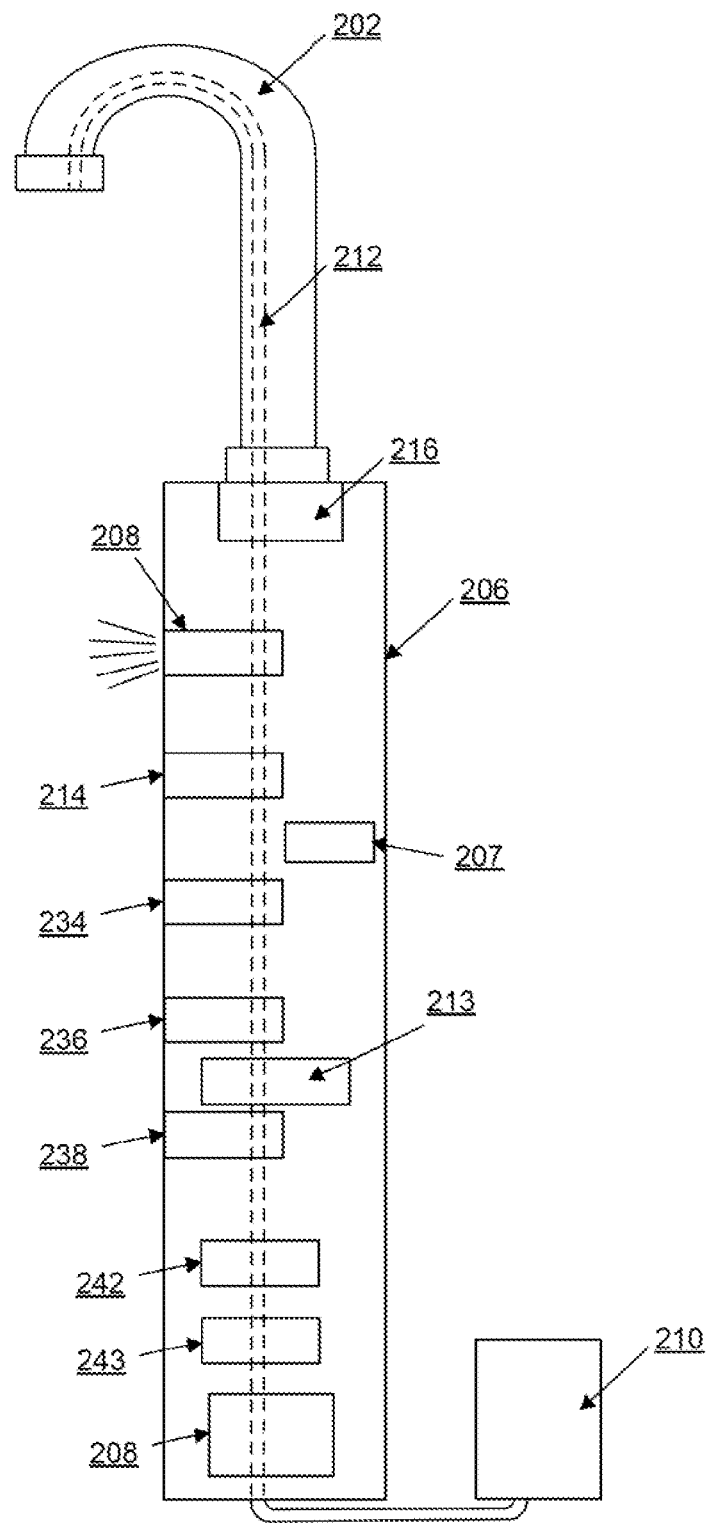

Unlike the water dispenser 102 discussed above, the water dispenser 202 can further comprise and support (by way of the housing 204) an agent dispensing system 213 that is capable of dispensing a composition directly from the water dispenser 202, in addition to the water dispenser 202 being configured to dispense water. In other words, the water dispenser 202 comprises a built-in or integrated agent dispensing system. The agent dispensing 213 system can comprise any components needed to facilitate the dispensing of the composition from the water dispenser 202, such as one or more chambers for housing or containing the composition or the separate cleansing and fluorescent agents that make up the composition, a composition outlet 201, various conduits that connect the one or more chambers to the composition outlet 201, any touchless or touch sensors and associated actuators, any manual actuators, and a pressure system for initiating flow and dispensing of the composition upon activation of an actuator. The composition may comprise at least a cleansing agent, and in some aspects, both a cleansing agent and a fluorescent agent as described above in reference to FIGS. 1A-G. The agent dispensing system 213 can comprise, and the cleansing agent and/or the composition may be delivered via or through, a composition conduit 212 that passes or that is routed through a portion of the housing 206 of the water dispenser 202 and that is in communication with a composition outlet 201 of the water dispenser 202. The composition conduit 212 may be a flexible tube or a rigid tube. The composition conduit 212 may be composed of different materials for different sections of the composition conduit 212. FIG. 2A depicts the composition conduit 212 as being routed through the neck of the water dispenser 202. In such a configuration, the composition conduit 212 may run parallel to the water conduit 205 that passes through the water dispenser 202 with the water outlet 203 for the water next to or adjacent the composition outlet 201 for the cleansing agent or composition as dispensed via the agent dispensing system 213. Thus, in one aspect, the composition and the water may be dispensed from the same general location on the water dispenser 202. In other aspects, the water outlet 203 for the water and the composition outlet 201 for the cleansing agent and/or the composition can be located apart from one another at different locations on the water dispenser 202. In essence, the composition conduit 212 may be in communication with the composition outlet 201 located anywhere on the housing 204 of the water dispenser 202. For example, the composition conduit 212 may be in communication with a composition outlet located in the base of the housing 106.

The agent dispensing system 213 can further comprise an actuator configured to activate the agent dispensing system 213 to dispense the cleansing agent and/or the composition. In one aspect, the actuator can comprise an electronically controlled actuator, such as a solenoid, associated with a pressure system (e.g., a pump) that is activated by a sensor, such as a touchless sensor. In another aspect, the actuator can comprise a manually activated actuator, such as a manual pump.

The agent dispensing system 213 can further comprise a composition chamber 210. The composition conduit 212 can be connected to the composition chamber 210 that contains the composition so as to connect the composition chamber 210 with the composition outlet 201 through which the composition exits the water dispenser 202. The composition chamber 210 may be located inside or outside of the housing 206. If outside of the housing 206, it is contemplated that the composition chamber 210, in one aspect, may be next to, adjacent to, or coupled to the water dispenser 202. In another aspect, the composition chamber 210 may be located at a location that is physically remote from the water dispenser 202, such as mounted or placed on the same surface the water dispenser 202 is mounted to, located in a cabinet beneath the water dispenser 202 and an associated wash basin, or at another location. For example, the composition chamber 210 may be located on a wash basin or at a location on a counter top proximate the wash basin. In one aspect, the composition chamber 210 can be configured to comprise a rigid container for housing the composition. In another aspect, the composition chamber 210 can comprise a flexible or non-rigid chamber housed within a support housing or shell. In any event, the composition chamber 210 can further comprise a first opening and a coupling interface associated with the first opening that is operable to releasably couple or connect with a mating coupling interface of the conduit 212, such that the conduit 212 is able to be in fluid communication with an inner portion of the composition chamber and the composition. The composition chamber 210 can further comprise an access member (e.g., a removable cap, or other type of structure) that facilitates access to the inner portion of the composition chamber through the first opening or another or second opening, wherein the access member facilitates the refilling of the composition chamber 210 as needed. Alternatively, the composition may be contained in a replaceable or interchangeable bag or container operable to be supported within a housing or shell of the composition chamber 210.

The agent dispensing system 213 can further comprise a pressure system 218 operable to draw or force the composition from the composition chamber 210, to deliver it to the composition outlet 201 in the water dispenser 202 via the composition conduit 212, and to ultimately dispense the composition from the water dispenser 202 through the composition outlet 201. The pressure system 218 can be configured so as to dispense a selective discrete amount of the composition at a time, which amount can be made to be adjustable. The pressure system 218 can be associated with the composition chamber 210, or it can be a stand-alone unit in communication with the composition chamber 210, or it can be supported by the housing 206. The pressure system 218 can be configured to impart a pressure (positive or negative) to the composition in the composition chamber 210 such that when the agent dispensing system 213 is activated to dispense the composition, the composition will be caused to flow through the composition conduit 212 to the composition outlet 201 in the water dispenser 202 as a result of the induced pressure within the conduit 212 from the pressure system 218. The pressure can be generated using different techniques. In one example, the composition can be contained in a replaceable bag serving as the composition chamber. With the replaceable bag filled with the composition, pressurized air can be directed into the bag that is greater than atmospheric pressure thus causing the bag to expand and the composition to flow out of the bag and into the composition conduit 212 where it can advance any composition already in the composition conduit 212 to a further downstream position, wherein composition within the composition conduit 212 proximate the opening of the composition outlet 201 is caused to exit the composition outlet 201, thus dispensing the composition from the water dispenser 202. The replaceable bag may have a coupling device (e.g., a connector) that mates with a connector on the composition conduit 212 such that the air pressure is maintained in the replaceable bag when the replaceable bag is installed. In another example, the pressure system 218 can comprise a pump operable with the composition chamber 210 to pump the composition from the composition chamber 210. The pump 222 can be supported in the housing 206 of the water dispenser 202, or in a housing in support of the composition chamber 210. The pump 222 may be activated via an actuator, such as a solenoid, which can be activated via a sensor, such as a touch or touchless sensor supported in the water dispenser 202. The pump 222 may be powered via a power source 208. Alternatively, the pump 222 can comprise a manually activated pump supported by the housing 206.

It is noted that the agent dispensing system 213 can be configured in a variety of ways and with a variety of components, and that those shown in the drawings and discussed herein are not intended to be limiting in any way. In essence, the present technology intends to cover any type of agent dispensing system integrally contained and supported within a water dispenser, wherein the agent dispensing system operates to dispense a cleansing agent and/or a composition out of the same fixture as that used to facilitate the dispensing of water.

Similar to the discussion above, the fluorescent agent and the cleansing agent of the composition in the composition chamber 210 may be premixed. Alternatively, the fluorescent agent may be contained in a first sub chamber 224 of the composition chamber 210 and the cleansing agent may be contained in a second sub chamber 226 of the composition chamber 210. Prior to or upon dispensing, the fluorescent agent and the cleansing agent may be mixed by a mixing mechanism 228 to combine the fluorescent agent and the cleansing agent into the composition.

The water dispenser 202 may include a light source 206 supported in the housing 204. The light source 206 can emit light in accordance with a predetermined field of view. The light source 206 may be capable of emitting the light at a sufficient intensity and wavelength so as to cause the fluorescent agent disposed about the skin or a covering of the skin of the individual to fluoresce at a wavelength in the visible spectrum, the field of view defines, at least in part, an inspection space in which the portion of the skin or the covering of the skin of the individual can be positioned to detect the at least one of a presence or an absence of fluorescing fluorescent agent during the decontamination event. The light source 206 may have all of the same features and capabilities as those described for the light source 108 of FIGS. 1A-G.

The light source 206 may be activated via a touch or touchless sensor 214, or by manual activation via a on/off switch (e.g., a button on an input panel). The touchless sensor 214 may be an optical sensor such as an infrared sensor. The touchless sensor 214 may have all of the same features and capabilities as those described for the first sensor 110 and the second sensor 116 of FIGS. 1A-G. Dispensing water from the water dispenser 202 may be activated by an actuator 216. The actuator 216 may have all of the same features and capabilities as those described for the actuator 104 of FIGS. 1A-1G. The touchless sensor 214 may also be used to activate the agent dispensing system 213 to dispense the composition. For example, different movements of the individual detected by the touchless sensor 214 may trigger different operations of either the agent dispensing system 213 or the actuator 216. Alternatively, the housing 206 may support a second touchless sensor where the touchless sensor 214 is used to activate the water and the second touchless sensor is used to activate the agent dispensing system 213 to dispense the composition.

The actuator 216, the light source 206, the touchless sensor 214, the components of the agent dispensing system 213, as well as other components of the water dispenser 202 may be powered via the power source 208. The power source 208 may have all of the same features and capabilities as those described for the power source 114 of FIGS. 1A-1G.

The power source 208 can be a replaceable battery, a rechargeable battery, inductively transferred power, and an alternating current power source. The power source 208 can include a power generator 232. The power generator 232 can have all of the same features and capabilities as those described for the power generator 122 of FIGS. 1A-1G.

The housing 206 can support an image capturing system 234. The image capturing system 234 may be capable of recording images during a decontamination event. The image capturing system 118 can also be used to retrieve an identification of the individual prior to or during the decontamination event. The image capturing system 234 can have all of the same features and capabilities as those described for the image capturing system 118 of FIGS. 1A-1G. Moreover, the image capturing system 234 can operate as a sensor and can further be configured to sense and record various movements of the individual undergoing a decontamination event and match these with stored predetermined movements that are acceptable and recognized for initiating or activating the agent dispensing system 213 and/or the water dispensing system of the dispensing apparatus in addition to any other electronically controlled elements (e.g., light source(s) as discussed herein.

The housing 206 can support an alert system 242, a timer 207, a notification device 238, a fingerprint scanner 236, and a data connection 243, that can have all of the same features and capabilities as those described for the alert system 126, the timer 112, the notification device 124, the fingerprint scanner 128, and the data connection 111 respectively of FIGS. 1A-1G. Moreover, the timer 207 can be operable with the agent dispensing system 213 and the water dispensing system to coordinate the dispensing of the composition and water in accordance with one or more timer programs, as discussed herein. An identification system 227 in conjunction with the image capturing system 234, the data connection 243, and/or the device 152 may be employed to identify the individual to perform the decontamination event. Data captured regarding the decontamination event can be stored with metadata associating the data with the identity of the individual.

Figure 2H:
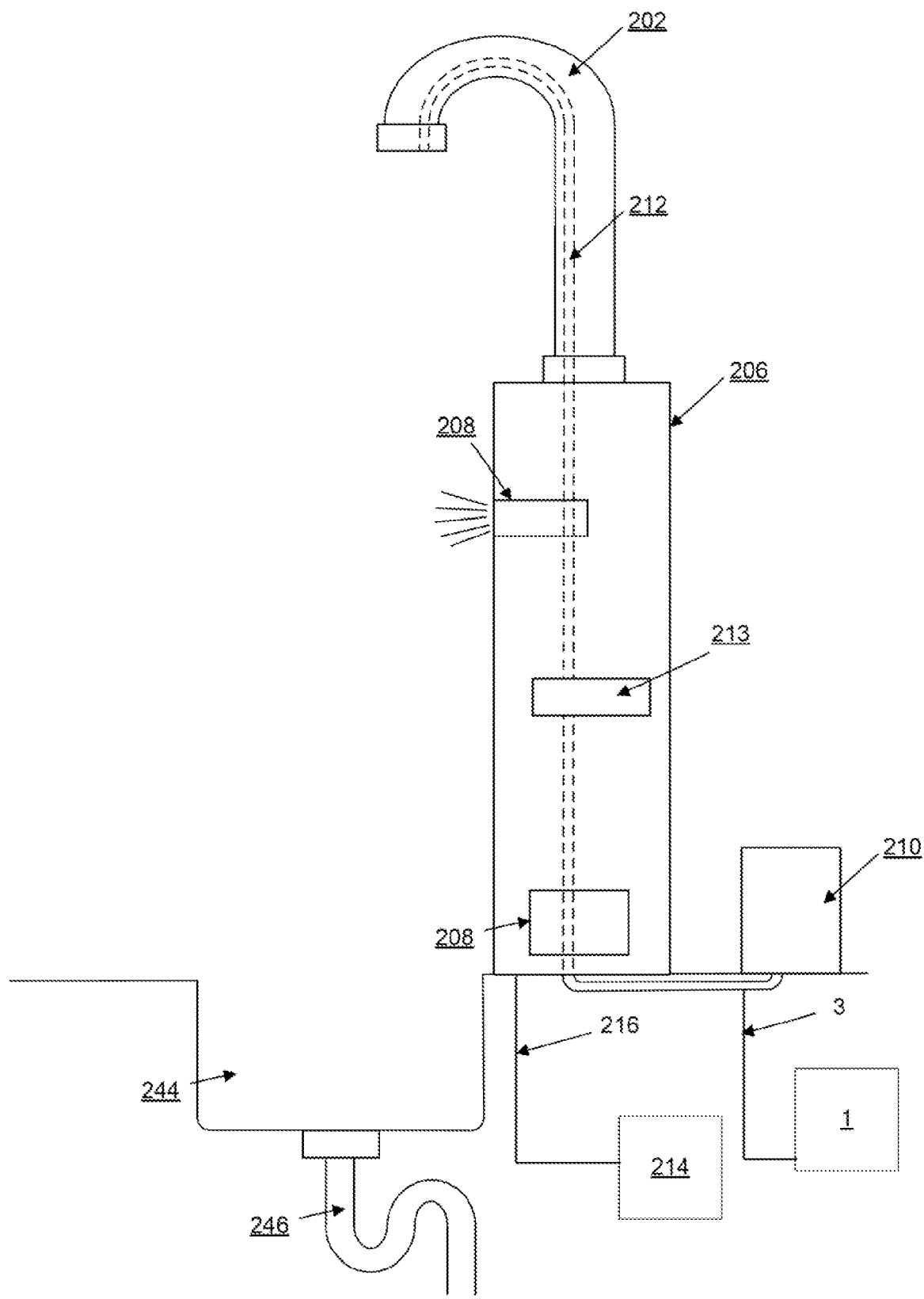
Figure 2I:
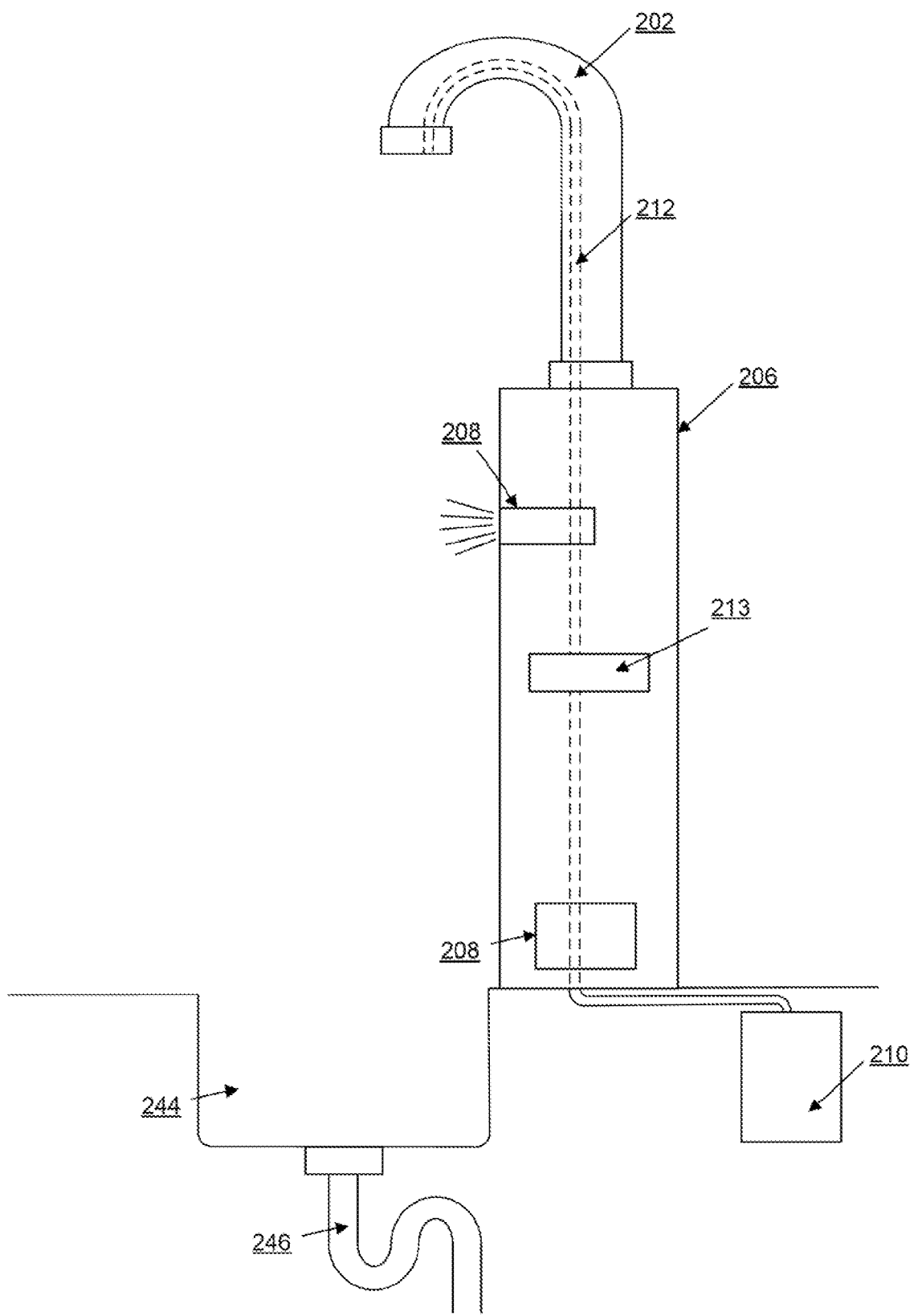

FIGS. 2H-I depict a system for facilitating effective decontamination of a portion of at least one of skin or a covering of the skin of an individual as part of a decontamination event, including assessing the effectiveness of the decontamination event. The system can include a wash basin 244. The wash basin 244 may be configured and utilized to capture water that is dispensed by the water dispenser 202 and any composition used during the decontamination event, and then to drain the water and the composition through the drain 234 to a managed utilities system. The system can further comprise the water dispenser 202, which may be mounted or otherwise coupled to a surface of the wash basin 244, to a counter or wall proximate the wash basin 244, or to any other structure proximate the wash basin 244 The system can further comprise the light source 208. The field of view of the light source 208 may be positioned so as to facilitate the emission of light onto the skin or covering of the skin of the individual during the decontamination event. In one aspect, the field of view can be positioned so as to be between a outlet water outlet 203 of the water dispenser 202 and the wash basin 244, but this is not intended to be limiting in any way. FIG. 2H depicts the composition chamber 210 as being mounted or placed on top of a horizontal surface which may be a counter top or a portion of the wash basin 244. FIG. 2I depicts the composition chamber 210 being placed or mounted below the horizontal surface. These positions or locations of the composition chamber are not intended to be limiting in any way.

The example water dispensers and water dispensing systems depicted and described in FIGS. 2A-I may also include a timer 207 and may be capable of executing one or more timer programs for dispensing the water and activating the light source(s) to emit light as described above. The timer 207 and timer programs can have all of the same features and capabilities, and can be configured and function in the same or a similar manner, as those described above. Additionally, the timer program may also be configured to control the dispensing of the composition via the agent dispensing system 213, and to coordinate the dispensing of the composition with the dispensing of the water, as well as the emission of light from the light source(s) for the purposes discussed herein.

With reference to FIGS. 3A-H, set forth is a dispensing apparatus 304 in accordance with an example of the present disclosure. The dispensing apparatus 304 can be configured to operate or to be operable with a water dispenser 302, such as an existing water dispenser 302, to dispense water from the dispensing apparatus 304. The water dispenser 302 can be of any type, configuration or design, and the dispensing apparatus 304 can be configured to facilitate the coupling or connection of the dispensing apparatus 304 to the water dispenser 302, which coupling or connection can be configured to facilitate removable or releasable coupling or connecting of the dispensing apparatus 304 to the water dispenser 302. The water dispenser 302 can be pre-installed, such as in a home, commercial setting or in any type of structure or facility utilizing a water dispenser for decontaminating a portion of the skin or a covering of the skin of one or more individuals. Thus the dispensing apparatus 304 can be installed onto any existing water dispenser, and can be referred to as a retro fit apparatus or system. Alternatively, the dispensing apparatus 304 can be included with a water dispenser, sold as a unit, where the dispensing apparatus 304 can be configured to be removable or releasable from the water dispenser.

The dispensing apparatus 304 can include a housing 305 capable of supporting all the components of the dispensing apparatus 304. The housing 305 may support the components by being molded or formed into shapes for coupling or mounting the components. The components may be coupled to the housing 305 using fasteners or a friction fit or other techniques. It is contemplated that the housing 305 can comprise any size, shape and configuration depending upon the size, shape and configuration of the water dispenser with which it is being utilized.

The dispensing apparatus 304 can further comprise a water dispensing system operable with the water dispenser 302 to facilitate the dispensing of water through the dispensing apparatus 304 once installed on the water dispenser 302. As part of the water dispensing system, a structural and fluid water dispenser interface 306 supported by or in the housing 305 can be configured to facilitate the coupling or connection of the dispensing apparatus 304 to the water dispenser 302, and also the subsequent dispensing of water from the water dispenser 302 through the dispensing apparatus 304. The water dispenser interface 306 can facilitate the physical and fluid coupling of the dispensing apparatus 304 to the water dispenser 302 using any type of connecting or coupling interface device or system. The water dispensing system of the dispensing apparatus 304 can further comprise a first opening formed in the housing 305, and an internal water conduit 312 supported in the housing 305 and in fluid communication with the first opening. The internal water conduit 312 can be configured to be in fluid communication with a water conduit and a water outlet 303 of the water dispenser 302 upon physically and fluidly coupling the dispensing apparatus 304 to the water dispenser 302 via the water dispenser interface 306. Thus, water from the water dispenser 302 can be caused to flow into the dispensing apparatus 304 and into the internal water conduit 312 of the dispensing apparatus 304, and then out of an outlet of the dispensing apparatus 304. Indeed, once the dispensing apparatus 304 is coupled to the water dispenser 302, water from the water dispenser 302 can pass through the internal water conduit 312 and can then be dispensed from the outlet in the dispensing apparatus 304, such as onto the skin or covering of the skin of an individual. The outlet in the dispensing apparatus 304 can comprise a variety of structural configurations, mechanisms and designs that can be found in existing water dispensers.

In one example, the water dispenser interface 306 may comprise an opening in the housing 305 that is threaded. The water dispenser 302 may have a threaded male portion about a water outlet 303 of the water dispenser 302 configured to threadably interface with and engage the threaded opening of the water dispenser interface 306. Thus, the dispensing apparatus 304 can be screwed onto the water dispenser 302 via the threaded coupling of the opening of the water dispenser interface 306 and the threaded male portion of the water dispenser 302 to secure the housing 305 and the dispensing apparatus 304 to the water dispenser 302 about the water outlet 303 of the water dispenser 302. In another example, the water dispenser interface 306 may comprise a clamping mechanism configured to facilitate the clamping and securing of the housing 305 and the dispensing apparatus 304 to the water dispenser 302 about the water outlet 303 of the water dispenser 302. The clamping mechanism can comprise a sleeve or other structural member capable of fitting over the male portion of the water dispenser 302 having the water outlet 303. The sleeve can be inserted over the male portion of the water dispenser 302. In one aspect, the sleeve can be clamped using an actuatable clamp that clamps and/or releases upon actuation. In another aspect, the sleeve can be configured to clamp using a friction fit. In still another example, the water dispensing interface 306 can be configured to mount the housing 305 of the dispensing apparatus 304 to another part of the water dispenser 302 not about the water outlet 303 of the water dispenser 302. In this example, the housing 305 of the dispensing apparatus 304 can comprise a mount 325 configured to interface with a base or other structure of the water dispenser 302, for example, to physically mount the housing 305 to the water dispenser 302. The water dispensing interface 306 can further comprise an elongate external tube 327 extending between the water outlet 303 of the water dispenser 302 and the housing 305 of the dispensing apparatus 304. The external tube can have at one end a coupling 329 configured to interface with and couple to at least a portion of the structure of the water dispenser 302 about the water outlet 303 (e.g., by way of clamping, friction fit, threading, or any other type of connecting interface), such that the external tube is in fluid communication with the water outlet 303 of the water dispenser 302. The external tube 327 can further be in fluid communication with the internal water conduit 312 of the dispensing apparatus 304, such that water from the water dispenser 302 is caused to flow into the dispensing apparatus 304, where it is then dispensed. Those skilled in the art will recognize that the dispensing apparatus 304 can be configured to both physically and fluidly couple to the water dispenser 302 in ways other than shown in the drawings and discussed here, each of which are contemplated and intended to be covered herein. In any event, the water dispensing interface 306 functions to provide both a physical coupling or connection and a fluid (water) coupling or connection of the dispensing apparatus 304 to the water dispenser 302.

The water dispensing system of the dispensing apparatus 304 can further comprise an actuator for activating the water to be dispensed from the outlet of the dispensing apparatus 304. The actuator can be configured to open and close a valve supported by the dispensing apparatus 304, such as in the housing 305. The actuator may be activated or triggered by a touchless sensor 318 supported in the housing 305. Alternatively, the dispensing apparatus 304 can comprise one or more manually activated devices (e.g., touch sensor, handles, electronic buttons, etc.) that are configured to control the valve(s) (or an actuator associated with the valve(s)) of the dispensing apparatus 304 to start and stop the flow of water. The water dispenser 302 may have one or more valves for controlling the dispensing of water where the valve(s) is/are manually or electrically controlled. Once the dispensing apparatus 304 has been installed onto the water dispenser 302, the valve(s) of the water dispenser 302 can be caused to be maintained in the open position so as to direct water into the dispensing apparatus 304 where the dispensing of the water can then be controlled solely by the dispensing apparatus 304.

The dispensing apparatus 304 can further comprise an agent dispensing system 307 supported at least partially within the housing 305. The agent dispensing system 307 can be configured to facilitate the dispensing of a cleansing agent and/or a composition onto a portion of the skin or a covering of the skin of an individual. The composition can include a fluorescent agent and a cleansing agent as described herein. The agent dispensing system 307 can comprise a composition chamber 318 that contains the composition. The agent dispensing system 307 can further comprise a separate chamber (not shown) that contains only a cleansing agent. The composition chamber 318 can be configured and can function in a similar manner as the composition chamber discussed above. The agent dispensing system 307 can further comprise one or more external composition conduits (e.g., external composition conduit 314), wherein "external" as used here is intended to mean that at least part of the one or more external composition conduits are external to or outside of the housing 305 of the dispensing apparatus 304. Using the external composition conduit 314 as an example, the external composition conduit 314 can be fluidly coupled to (i.e., in fluid connection with) an internal composition conduit 331 (i.e., at least partially internal to the housing 305) and a composition outlet 301 supported in and/or defined by the housing 305 of the dispensing apparatus 304 via an interface coupling supported at one end of the conduit 314, and to the composition chamber 318 via an interface coupling supported at the other end of the conduit 314. The agent dispensing system 307 can be configured to cause, upon being activated, the composition to flow from the composition chamber 318, through the external composition conduit 314, through the internal composition conduit 331, and out of the composition outlet 301 of the dispensing apparatus 304. The interface couplings of the conduit 314 can comprise any type of connection or coupling operable to fluidly couple the external composition conduit 314 to both the composition outlet 301 of the agent dispensing system 307 and the composition chamber 318 to facilitate flow of the composition out of the composition chamber 318 and ultimately out of the dispensing apparatus 304.

The external composition conduit 314 can be routed along the outside of at least a portion of the water dispenser 302. In the example shown, the external composition conduit 314 is secured to and runs along a neck of the water dispenser 302, where it then enters into the dispensing apparatus 304 as part of the agent dispensing system 307. The external composition conduit 314 can be fastened or attached to the water dispenser 302 using any type of securing means, such as couplers 309. The couplers 309 can comprise a bracket, a zip tie, a clamp, a hose clamp, a worm drive clamp, or any other type of coupling device operable to secure the external composition conduit 314 to a component of the water dispenser 302. Alternatively, the external composition conduit 314 can be secured to the water dispenser 302 using an adhesive.

The dispensing apparatus 304 can further comprise a covering 333 or shroud. In one example, the conduit 314 can be shrouded in a covering 333 or shroud that covers the external composition conduit 314, or a portion of the external composition conduit 314, and the portion of the water dispenser 302 in support of the external composition conduit 314 (e.g., the neck of the water dispenser 302). The covering 333 can protect the conduit 314 from damage or being removed from the water dispenser 302 and can allow the conduit 314 to be hidden from view. The covering 333 can comprise a hard or rigid covering (e.g., a plastic clamshell covering), or it can comprise a flexible or semi-rigid covering (e.g., one made of cloth, rubber, or other materials). The covering 333 can be secured to at least a portion of the water dispenser 302 using any conventional securing means, such as those used to secure the external composition conduit 314 to the water dispenser 302.

The dispensing apparatus 304 can further comprise one or more light sources (e.g., light source 308) that are supported by the housing 305, that can be powered and electrically coupled to a power source, such as power source 316, and that can emit light in accordance with a predetermined field of view, wherein the light source is configured to emit the light at a sufficient intensity and wavelength so as to cause the fluorescent agent disposed about the skin or a covering of the skin of the individual to fluoresce at a wavelength in the visible spectrum, and wherein the field of view defines, at least in part, an inspection space in which the portion of the skin or the covering of the skin of the individual can be positioned to detect the presence or absence of fluorescing fluorescent agent during the decontamination event.

Furthermore, the dispensing apparatus 304 can comprise one or more sensors, such as touchless sensor 318, configured to activate any one or more of the water dispensing system for dispensing water, the agent dispensing system 307 for dispensing the composition, and/or the one or more light sources such as light source 308. Dispensing the water and the composition can be activated via the one or more sensors. More than one touchless sensor can be employed to dispense the composition, the water and to activate the light source(s), such as light source 308. For example, the dispensing apparatus 304 can include three touchless sensors where each sensor is supported and configured to emit light in a different orientation or direction and with a different field of view. The fields of view may or may not overlap one another. The three sensors can respectively control or can be caused to be activated to control different operations of the dispensing apparatus 304, namely the dispensing of the water, the dispensing of composition, and the emission of the light. Alternatively, a single touchless sensor can be employed to activate different operations of the dispensing apparatus 304. This can be accomplished by configuring the touchless sensor to detect different movements or gestures of the individual.

The light source(s), the touchless sensor(s), the agent dispensing system 307, the actuator for dispensing the water, and other components of the dispensing apparatus 304 can all be powered by the power source 316. The power source 316 may further include a power generator 317 that may comprise an impeller in the internal water conduit 312 that when turned or rotated will generate electricity to charge a battery associated with the power source 316. The power generator 317 may have all of the same features and capabilities as those described for the power generator 122 of FIGS. 1A-G.

It is noted that the light source(s) such as light source 308, the touchless sensor(s) such as touchless sensor 318, the agent dispensing system 307, the power source 316, and the composition chamber 318 can have all of the same features and capabilities, and can be configured and function in the same or a similar manner as those described above for the light sources, the touchless sensors, the agent dispensing systems, the power sources, and the composition chambers of FIGS. 1A-G and FIG. 2A-I.

The agent dispensing system 307 can further comprise a pressure system 322 configured to cause the composition to flow out of the composition chamber 318 and to be dispensed through the composition outlet 301. In one example, the pressure system 322 can comprise a pump 324 configured to pump the composition from the composition chamber 318. The pump 324 can be supported in the composition chamber 318, as depicted, or in the housing 305. The pressure system 322 and the pump 324 can have all of the same features and capabilities, and can be configured and function in the same or a similar manner, as those described above for the pressure system 218 and the pump 222 of FIGS. 2A-21. The composition can be premixed in the composition chamber 318. Alternatively, the fluorescent agent may be contained in a first sub chamber 326 of the composition chamber 318 and the cleansing agent may be contained in a second sub chamber 328 of the composition chamber 318. Prior to or upon dispensing the fluorescent agent and the cleansing agent may be mixed by a mixing mechanism 332 to combine the fluorescent agent and the cleansing agent into the composition, also as discussed above.

The dispensing apparatus 304 can further comprise a power generator 334, an image capturing system 336, a fingerprint scanner 338, a data connection 339, a notification device 342, and an alert system, which can have all of the same features and capabilities, and can be configured and function in the same or a similar manner, as those described for the power generators, the image capturing systems, the fingerprint scanners, the data connections, the notification devices, and the alert systems of FIGS. 1A-1G and FIGS. 2A-I. With respect to the image capturing system 336, this can further be configured to operate as a sensor to sense and record various movements of the individual undergoing a decontamination event and match these with stored predetermined movements that are acceptable and recognized for initiating or activating the agent dispensing system and the water dispensing system of the dispensing apparatus. An identification system 337 in conjunction with the image capturing system 336, the data connection 339, and/or the device 152 may be employed to identify the individual to perform the decontamination event. Data captured regarding the decontamination event can be stored with metadata associating the data with the identity of the individual.

Figure 3A:
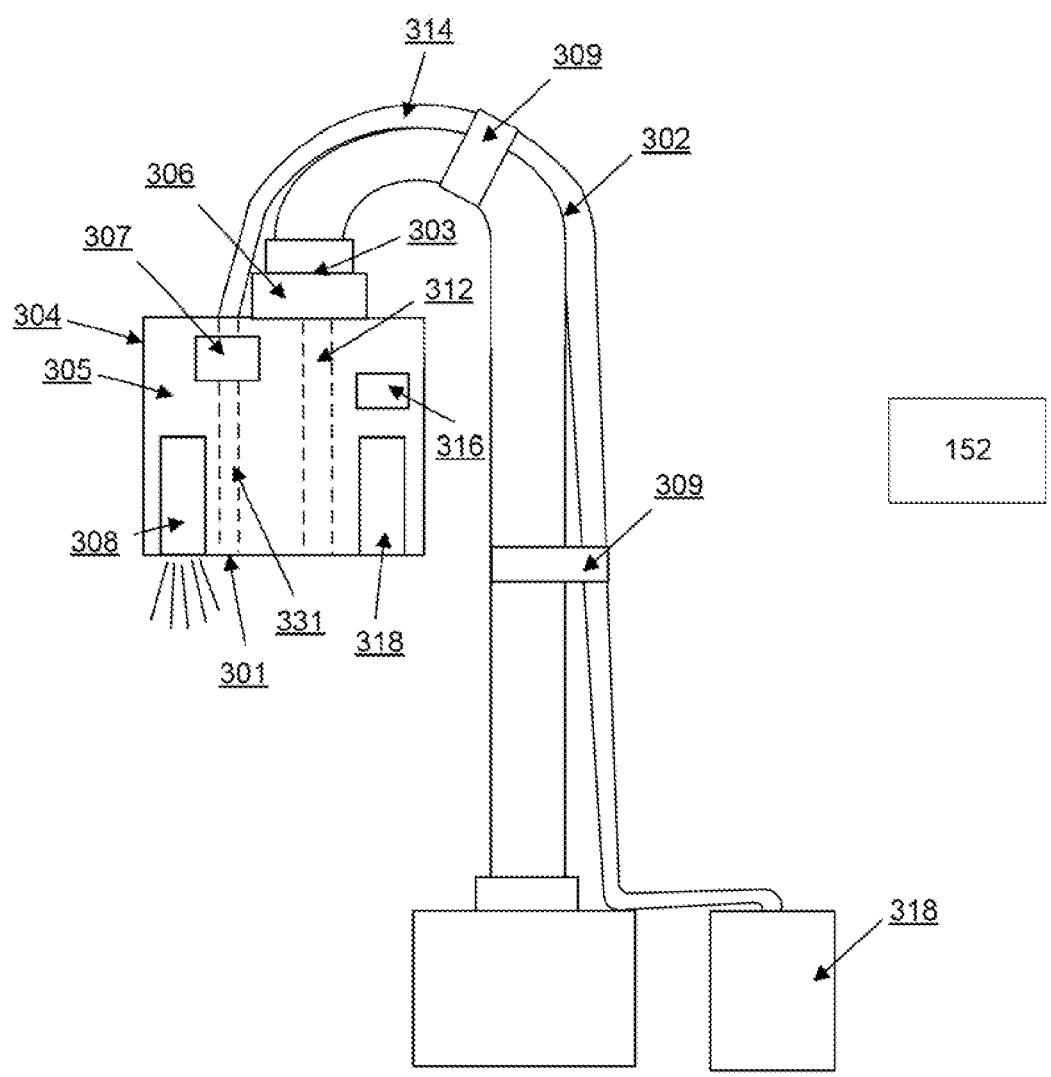
FIGS. 3A-H are block diagrams of dispensing apparatuses and systems with a housing for facilitating assessing the effectiveness of a decontamination event to decontaminate a portion of skin or a covering of the skin of an individual in accordance with aspects of the technology.
Figure 3B:
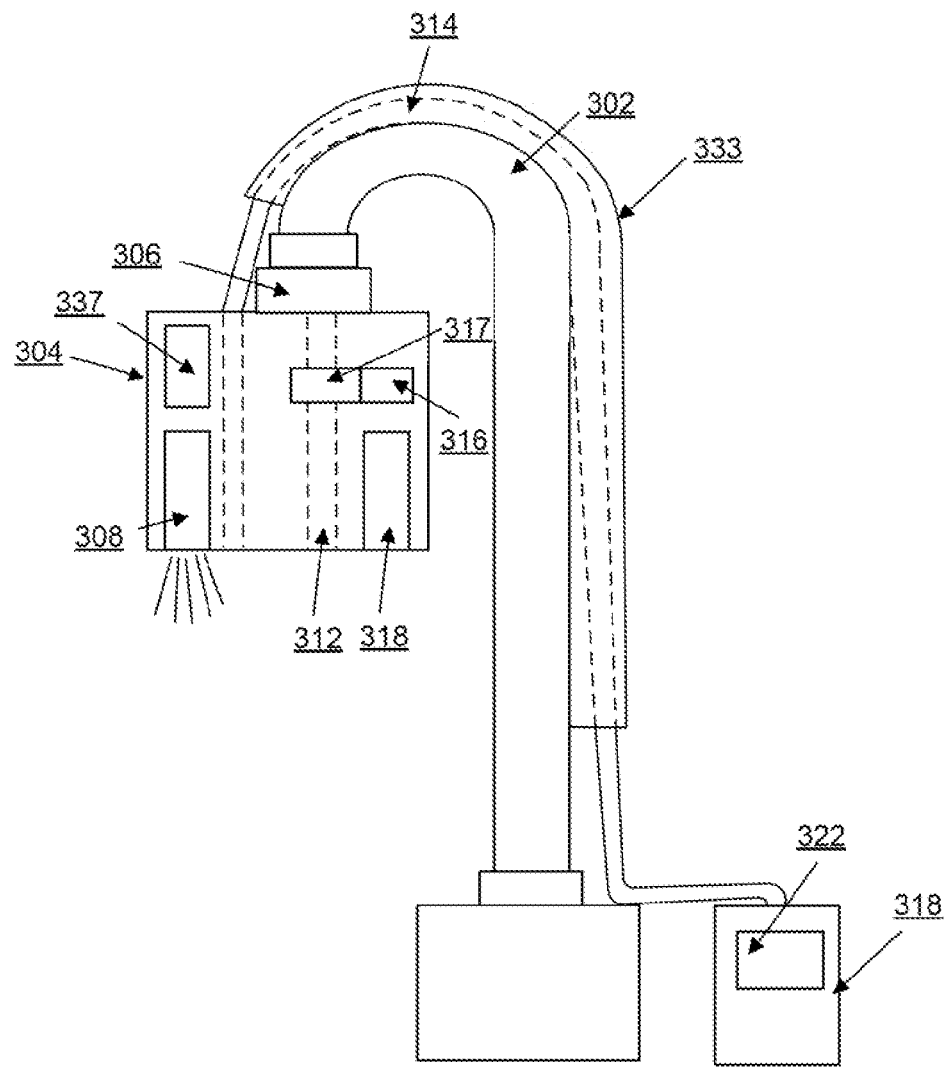
Figure 3C:
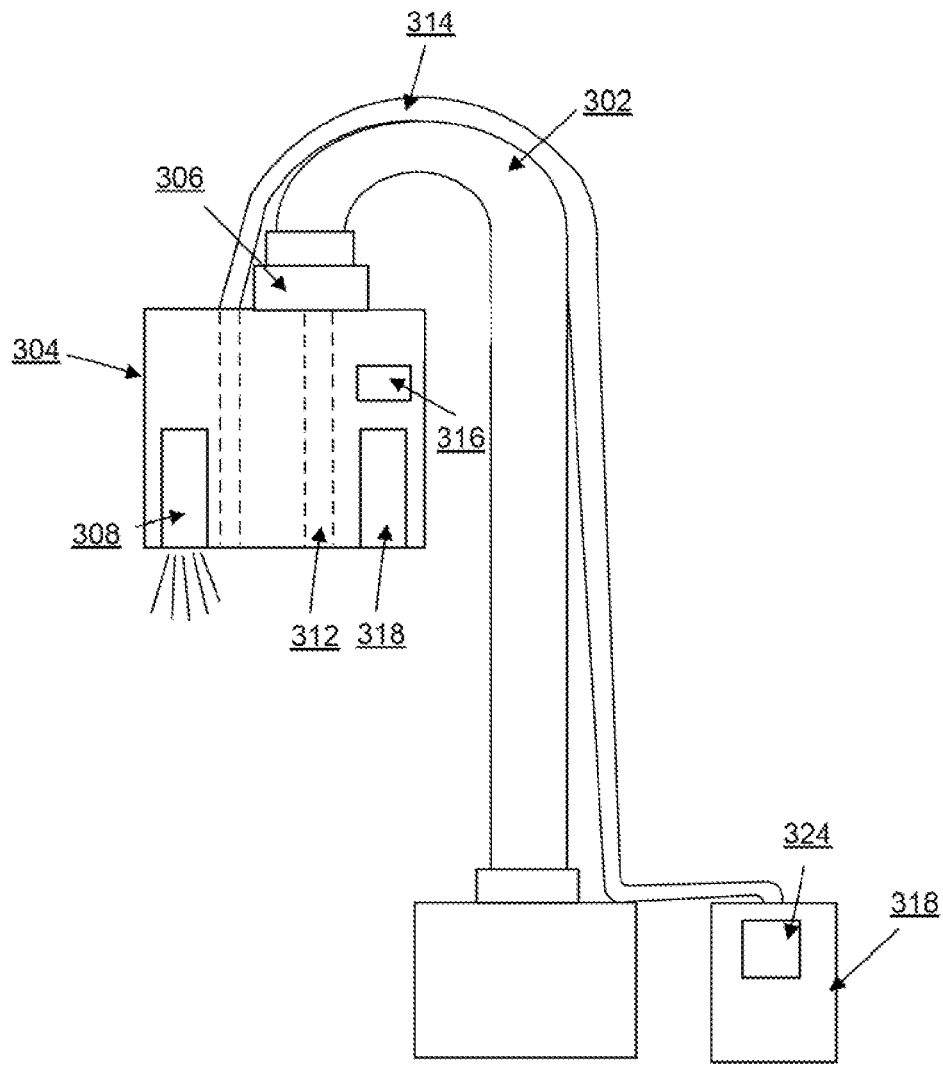
Figure 3D:
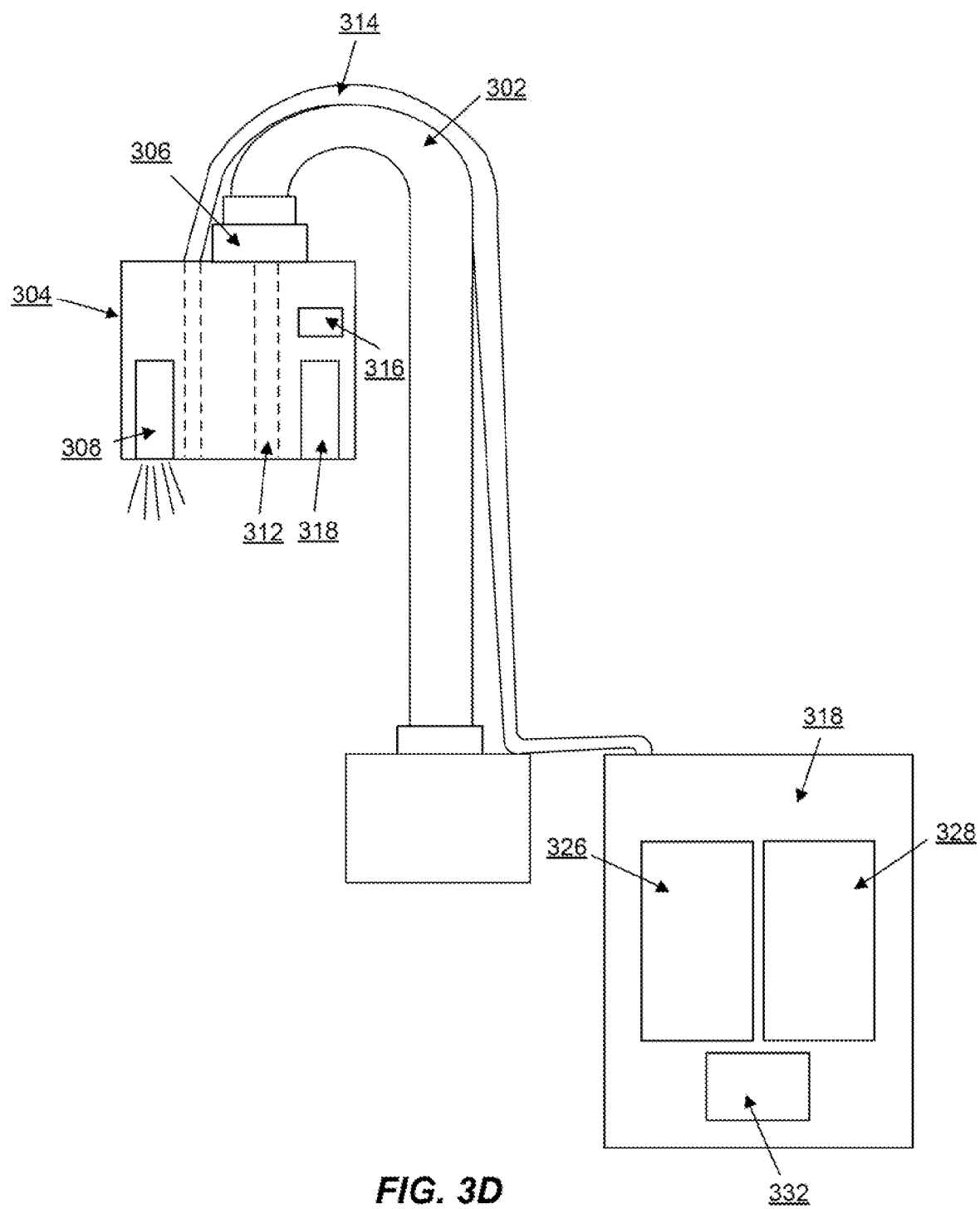
Figure 3E:
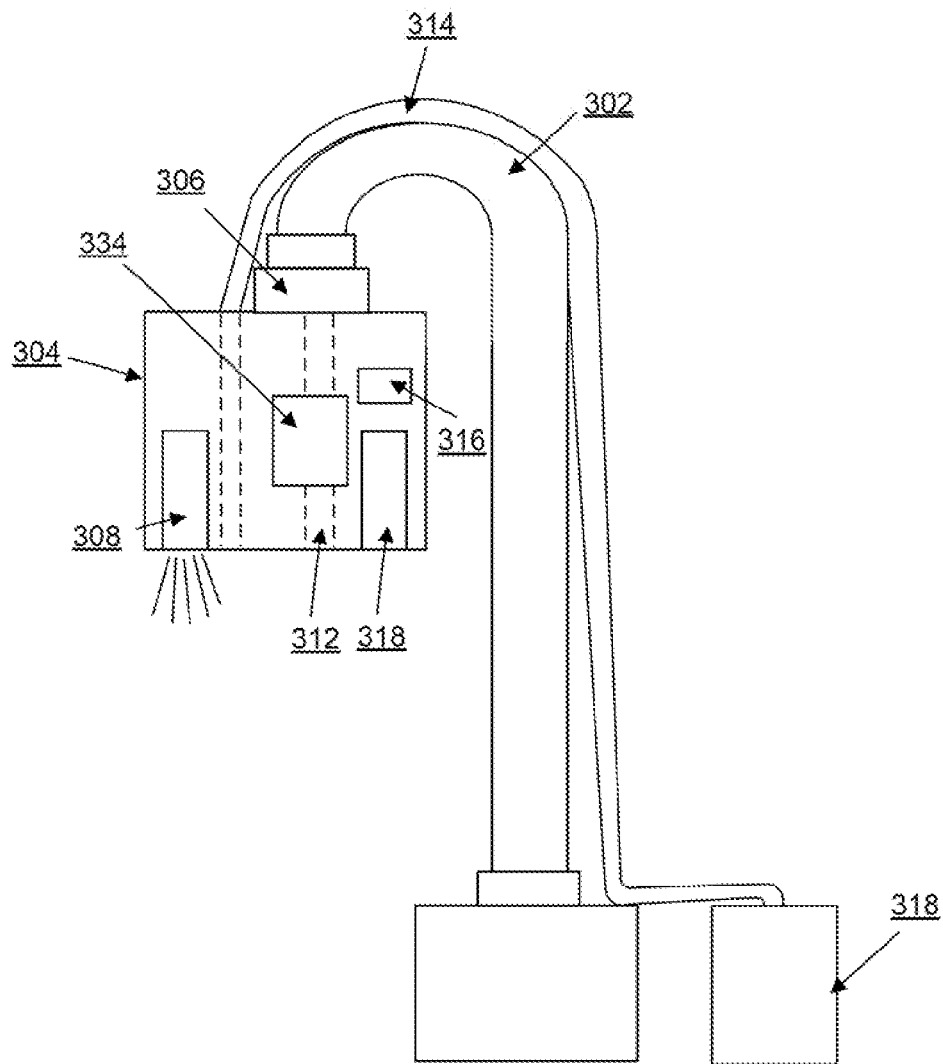
Figure 3F:
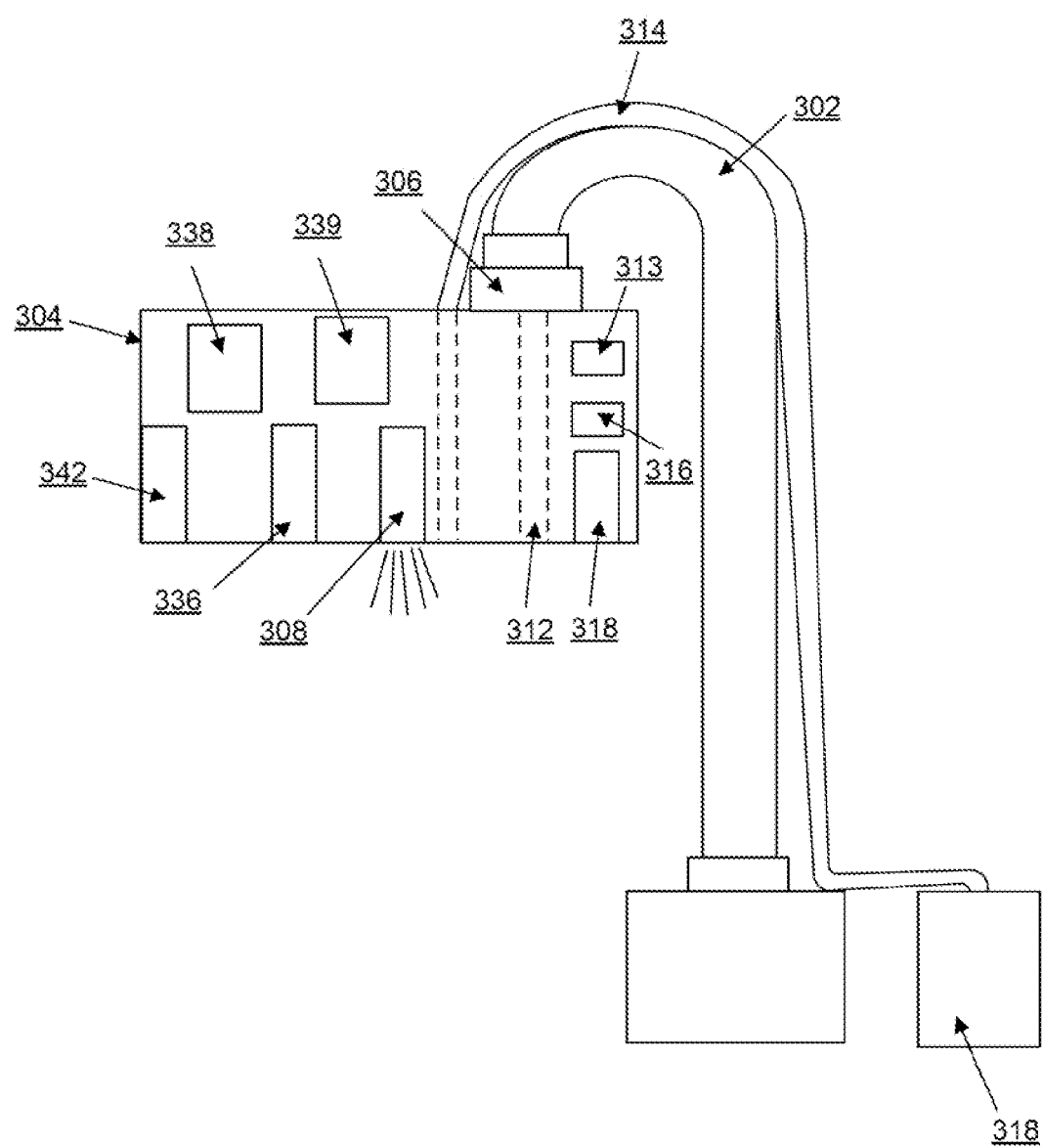
Figure 3G:
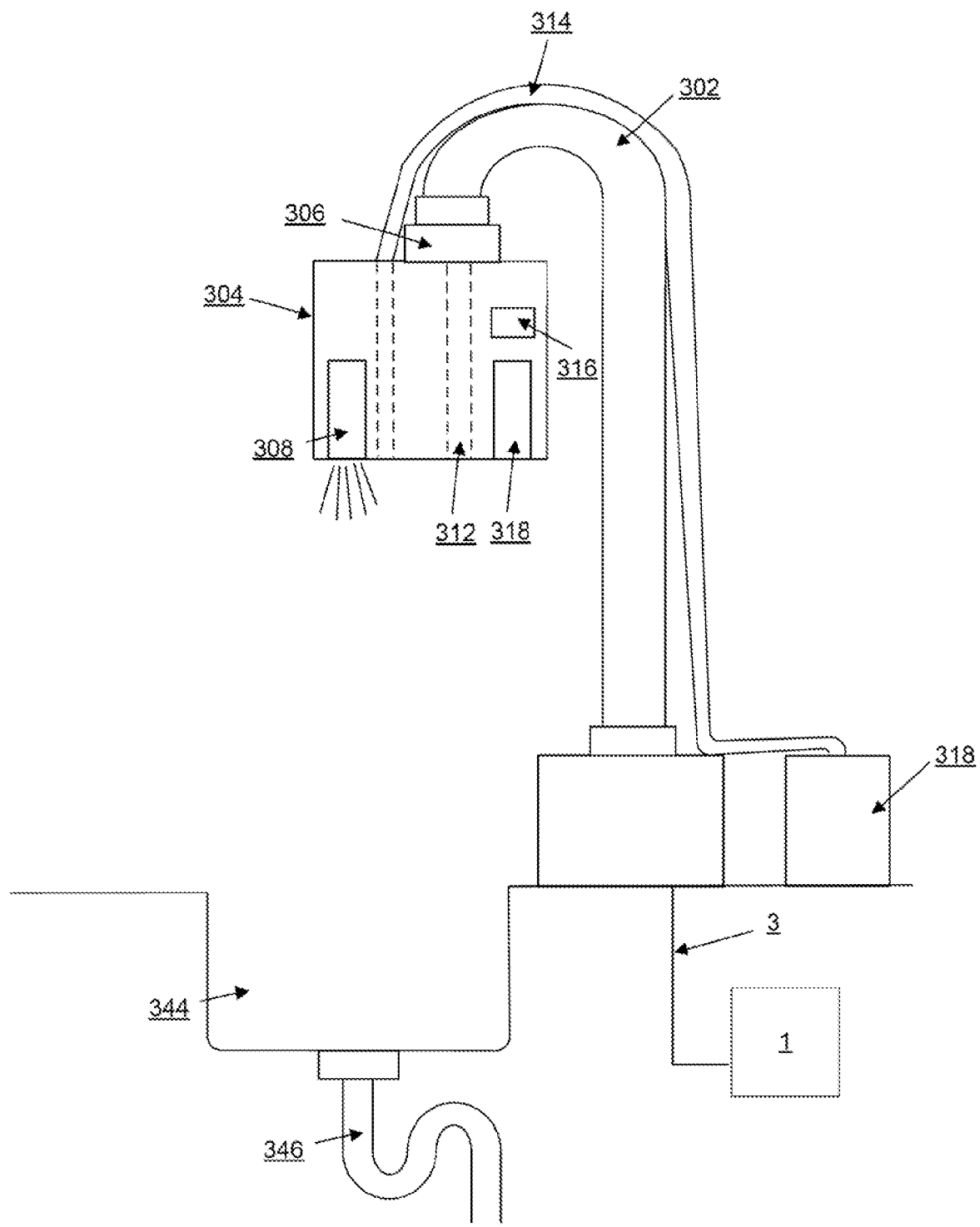
Figure 3H:
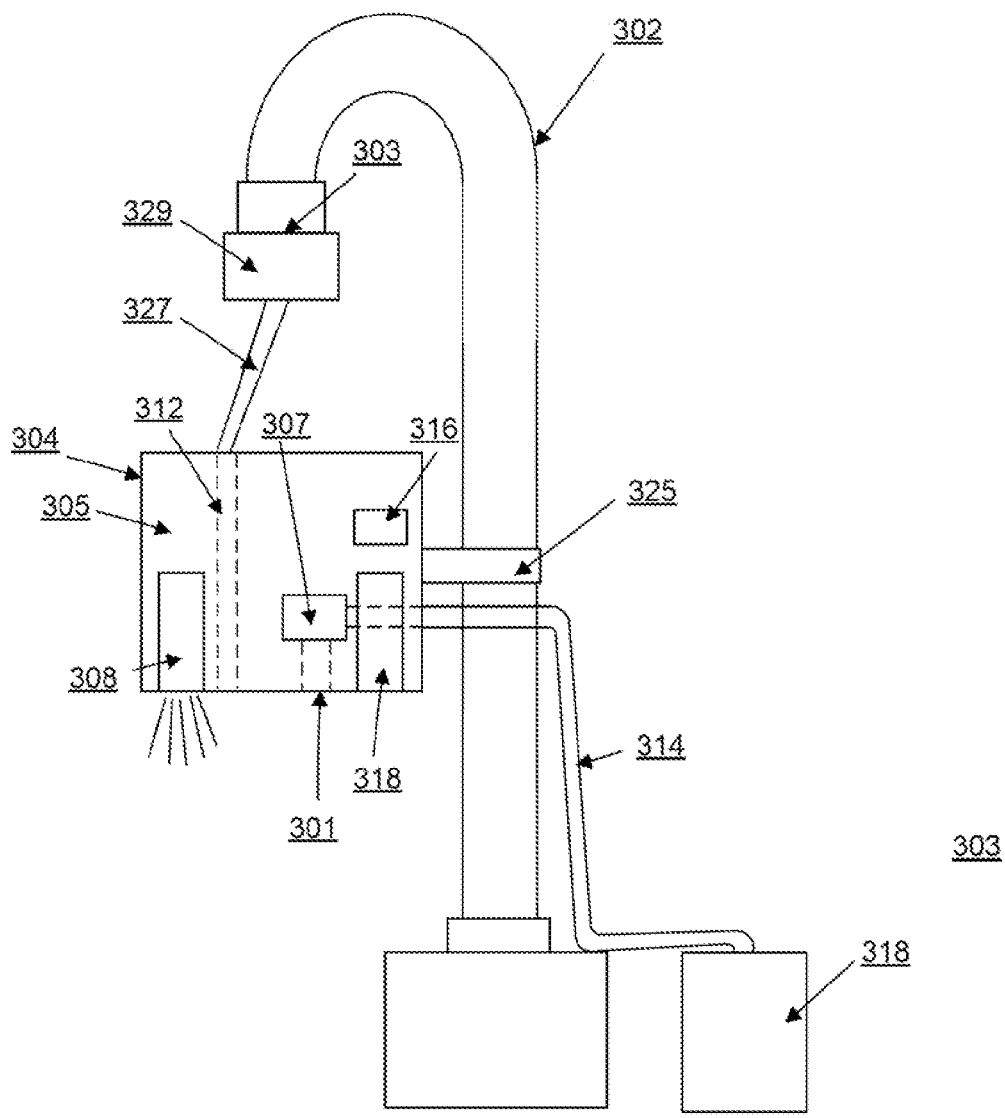

FIG. 3F depicts a system for facilitating effective decontamination of a portion of at least one of skin or a covering of the skin of an individual as part of a decontamination event, including assessing the effectiveness of the decontamination event. The system can include a wash basin 344 configured and utilized to capture water that is dispensed by the water dispenser 202 and any composition used during the decontamination event, and then to drain the water and the composition through the drain 234 to a managed utilities system. The water dispenser 302 may be mounted or otherwise coupled to a surface of the wash basin 344, to a counter or wall proximate the wash basin 344, or to any other structure proximate the wash basin 344. The field of view of the light source(s), such as light source 308, may be positioned so as to facilitate the emission of light onto the skin or covering of the skin of the individual during the decontamination event. In one aspect, the field of view can be positioned so as to be between one or both of the water and the composition outlet 301 of the dispensing apparatus 304 and the wash basin 344, but this is not intended to be limiting in any way. The composition chamber 318 can be mounted or placed on top of a horizontal surface, as depicted, which may be a counter top or a portion of the wash basin 344. Alternatively, the composition chamber 318 can be placed or mounted below the horizontal surface, such as in a cabinet or other enclosure.

The example dispensing apparatus and systems depicted and described in reference to FIGS. 3A-H may also include a timer 313 configured to execute one or more timer programs for coordinating the dispensing of the water and the activating of the light source(s) to emit light as described above. The timer 313 and timer programs can have all of the same features and capabilities, and can be configured and function in the same or a similar manner, as those described above. Additionally, the timer 313 can be operable with the agent dispensing system 307 and the water dispensing system, wherein the timer 313 can be configured to control the dispensing of the composition via the agent dispensing system 307 and the water via the water dispensing system, and to coordinate, in accordance with one or more timer programs, the dispensing of the composition with the dispensing of the water, as well as the emission of light from the light source(s) for the purposes discussed herein.

With reference to FIGS. 9A-G, set forth is a system for facilitating effective decontamination of a portion of at least one of skin or a covering of the skin of an individual as part of a decontamination event in accordance with an example of the present disclosure. The system can comprise a composition dispenser 902 and a light module 906. The light module 906 may be located remote to the composition dispenser 902 and connected to the composition dispenser 902 via a conduit or cable 910. The cable 910 can be configured with or can comprise a plurality of different types of wires or cables. The composition dispenser 902 can include a dispenser housing 916 to house and support the components of the composition dispenser 902. The composition dispenser 902 can dispense a composition that includes a cleansing agent and a fluorescent agent. The composition dispenser 902 can include a power source 904 supported in the dispenser housing 916. The components of the composition dispenser 902, such as the power source 904, can be mounted to the dispenser housing 916 using screws or other fasteners. Alternatively the components of the composition dispenser 902 may be friction fit into a molded section of the dispenser housing 916. The power source 904 may be a replaceable battery, a rechargeable battery, inductively transferred power, or an alternating current power source. The power source 904 can provide electrical power to the components of the composition dispenser 902 as well as components of the light module 906.

The light module 906 can include components such as a light source 908. The components of the light module 906 can be fastened, friction fit, or otherwise supported in a module housing 914 of the light module 906. The light source 908 can be electrically powered by the power source 904 of the composition dispenser 902 via the cable 910. The light source 908 can also be controlled via components of the composition dispenser 902 via the cable 910. For example, the composition dispenser 902 can include a processor 918 and a memory 920. The processor 918 and the memory 920 can control the light source 908 to emit light for a predetermined amount of time or according to a timer program as described above. The light source 908 may be controlled by turning the power from the power source 904 on and off. Alternatively, the power source 904 may provide a constant source of power to the light source 908 and the emission of light from the light source 908 can be controlled via a data cable that is one of the plurality of cables supported within the cable 910. In one example, the light source 908 can be triggered or activated to emit light for a predetermined period of time when an individual engages the composition dispenser 902 to dispense the composition. For example, the composition dispenser 902 can be manually engaged to pump out the composition, or the composition dispenser 902 can be engaged via a touchless sensor such as a sensor 954. Upon dispensing the composition, the processor 918 and memory 920 can be employed to control the light source 908 to emit light.

The predetermined time that the light source 908 emits light can be preset and can be user adjusted. The predetermined amount of time can be adjusted by a user accessing a processor 918 and memory 920. The user can access the processor 918 and memory 920 via a data connection 956. The data connection can be a wireless device that allows the user access the processor 918 and memory 920 via another device such as a computer system, a smart phone, a smart watch, or any other type of computing or mobile device. The wireless device may allow the user to access the processor 918 and memory 920 remotely over a network. The wireless device may also facilitate access by the processor 918 and memory 920 to one or more remote databases over a network. The data connection 956 may also be a wired connection and have standard or proprietary port connections such as a universal serial bus (USB) port. The data connection 956 can be a memory card slot that allows the user to insert a memory card into the composition dispenser 902 and adjust or modify the settings of the composition dispenser 902. A wired port or memory card slot may be protected via a cover or other device to protect the data connection 956 from water intrusion. For example, the cover may be composed of a rubber material that is friction fit into the data connection 956 when the data connection 956 is not in use. The data connection 956 can also be used to modify, add, or delete timer programs for the composition dispenser 902.

In other examples, the processor 918 and memory 920 can be manually interfaced with using one of a plurality of electronic inputs 158 on an input panel 160 of the composition dispenser 902. The electronic inputs 158 can be used to adjust or customize timer programs or a predetermined amount of time that the light source 908 emits light. Each of the electronic inputs 158 can be associated with a respective timer program. The electronic inputs 158 can also be employed to activate or start the execution of a given timer program. The input panel 160 can include a display 162 capable of outputting information regarding the timer programs or other data. For example, display 162 may be a screen that displays numbers or text indicating which timer program has been selected. The display 162 may be one or more lights that indicate which timer program has been selected. The lights may have text, numbers or symbols printed next to the lights. The lights may be different colors where each color indicates a different timer program. The display 162 may also be used to interface with the individual to adjust or modify the timer programs.

The light source 908 can emit light in a predetermined field of view. The field of view can define an inspection space for the decontamination event. For example, the inspection space or the field of view of the light source 908 can be between an outlet 924 of a water dispenser 912 and a wash basin 926. Such a field of view allows an individual to inspect a portion of skin or a covering of the portion of the skin of the individual to be inspected over the wash basin 926 during the decontamination event with the light impinging on the portion of skin or the covering of the portion of the skin. With the field of view between the outlet 924 and the wash basin 926, any water or composition that drips off of the individual may fall into the wash basin 926 during the decontamination event.

The light source 908 can emit light at a sufficient intensity and wavelength so as to cause the fluorescent agent of the composition that is disposed about the skin or the covering of the skin of the individual to fluoresce at a wavelength in the visible spectrum. In one example the light source 908 can be caused to emit light with a wavelength and intensity that causes a fluorescent agent to fluoresce or illuminate in a spectrum visible to the human eye. Depending upon the type of fluorescent agent, the light source 908 can be configured to emit light in one or more of several wavelengths or ranges of wavelengths to cause the fluorescent agent to fluoresce or illuminate. In one example, the light source 908 may be configured to emit an ultra violet (UV) light. The UV light may have a wavelength of about 150-400 nanometers (nms). The UV light may be ultraviolet A (UVA), ultraviolet B (UVB), ultraviolet C (UVC), or a combination thereof. UVA may be light that has a wavelength of about 400-315 nms. UVB may be light that has a wavelength of about 312-280 nms. UVC may be light that has a wavelength of about 280-100 nms. In another example, the light source 108 can be configured to emit light that has a wavelength in the visible spectrum of about 400-700 nms. In still another example, the light source 108 can be configured to emit light that has a wavelength in the infrared spectrum of about 700 nm to 1 millimeter. In one example, the light source 108 can be configured to emit light that provides a germicidal effect when incident upon the skin or a covering of the skin of the individual. The light source 108 may emit light in more than one of the described spectrums of light.

The fluorescent agent may be described as a fluorescent dye that illuminates when illuminated by light from a specific spectrum or light from a range of wavelengths. For example, the fluorescent agent can be compounds containing fluorophores, fluorescein, xanthene dyes, rhodamine dyes, stilbene dyes, functionalized polycyclic aromatic hydrocarbon dyes including lissamine flavine FF, pyranine, and/or amino G acid, triarylmethane dyes, methyl violet dyes, fuchsine dyes, phenol dyes, malachite green dyes, victoria blue dyes, diarylmethane dyes, and fluorescent fruit extracts including extracts from Viburnum trilobum, Ribes, and Ribes alpine. The fluorescent agent can be a combinations of the described compounds.

The fluorescent agent may be mixed or combined with a cleansing agent to form a composition. The composition dispenser 902 may be physically located proximate to the water dispenser 102 and intended to be used by the individual in conjunction with the water dispenser 912 during a decontamination event. The composition may be dispensed out of a dispensing outlet 913. The dispensing outlet 913 may be a nozzle or other type of outlet for releasing the composition for application onto the skin or covering of the skin of an individual. In one aspect, the composition of the fluorescent agent and the cleansing agent may be premixed and added to a chamber 928 of the composition dispenser. In another aspect, the fluorescent agent may be housed or contained in a sub chamber such as a first chamber 930 of the composition dispenser separate from a second chamber 932 containing the cleansing agent, wherein the fluorescent agent and the cleansing agent may be brought together and mixed via a mixing mechanism 934 prior to or during dispensing. The composition can then be applied to the skin or covering of the skin of the individual as part of a decontamination procedure, such as to wash the individual's hands. When the composition, with its mixture of the fluorescent agent and the cleansing agent, is applied to the skin or the covering of the skin of the individual, the fluorescent agent can then be indicative of the spread or presence or location of the cleansing agent as applied to and about the skin or covering of the skin of the individual upon illuminating the fluorescent agent with the light from the light source 908 to cause the fluorescent agent to fluoresce. For example, if the fluorescent agent and the composition are properly mixed into the composition, then if the fluorescent agent is detected upon the skin of the individual the individual can be assured that the cleansing agent is also located on the same portions of the skin, and the individual can continue with the washing procedure, which includes at least some of the steps of wetting the skin or covering of the skin, applying the composition, washing (lathering and/or scrubbing), and rinsing to remove the composition.

The cleansing agent can be liquid soap, powdered soap, antibacterial soap, and antimicrobial soap. The cleansing agent can also be chlorhexidine gluconate (clear/pink solution); iodine based preparations (brown), and aqueous alcoholic solutions (clear). The cleansing agent can also be a combination of the compounds described herein. In one example, the cleansing agent is a waterless sanitizing compound such as an alcohol based compound.

Figure 9A:
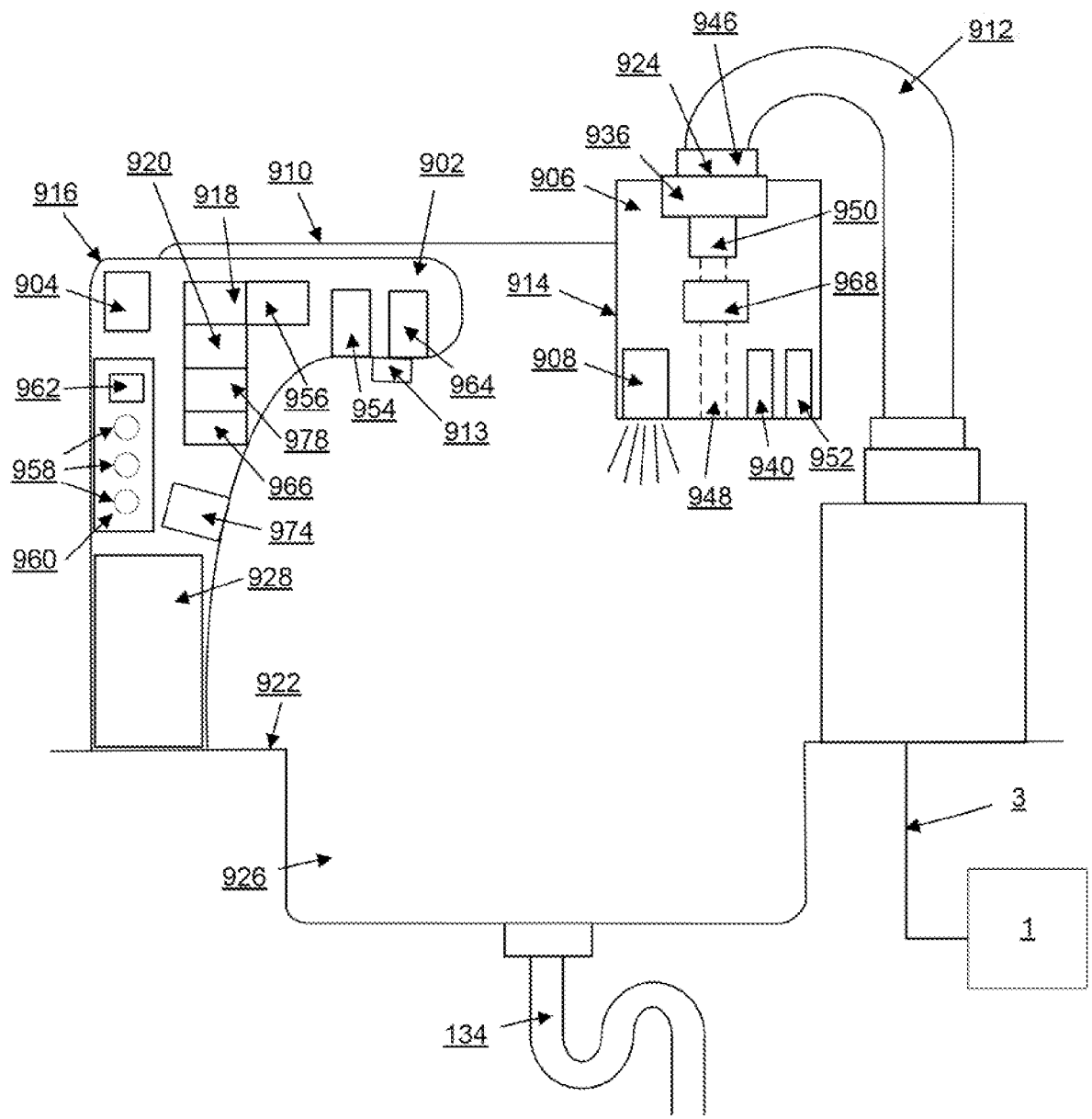
FIGS. 9A-E are block diagrams of dispensing apparatuses and systems with a housing for facilitating the effectiveness of a decontamination event to decontaminate a portion of skin or a covering of the skin of an individual in accordance with aspects of the technology.
Figure 9B:
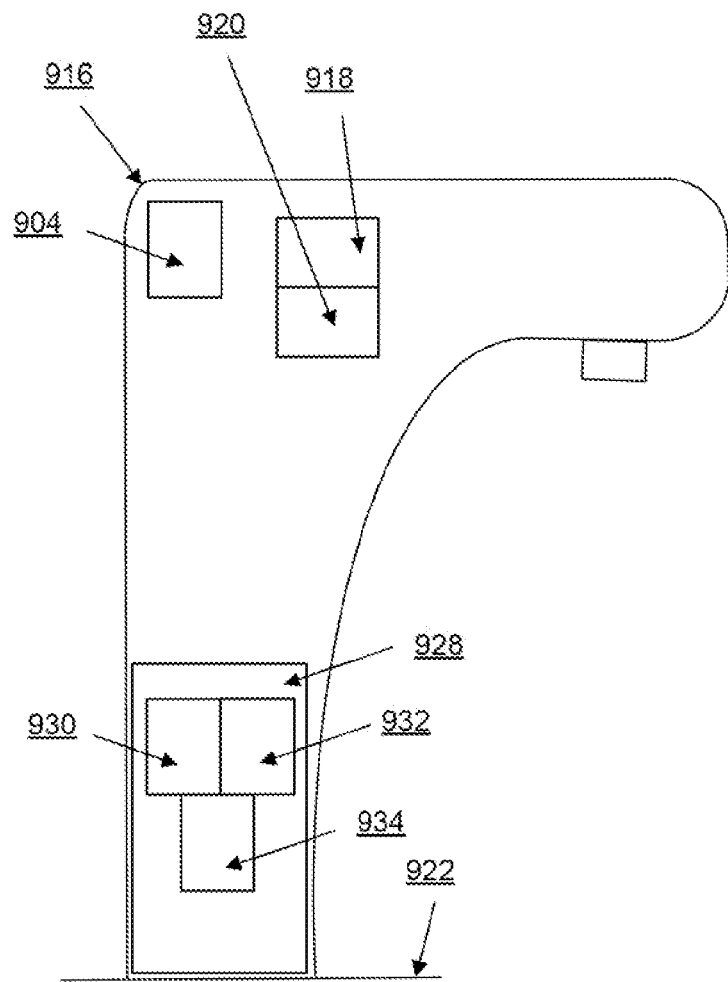

The cable 910 depicted in FIG. 9A is intended to represent the connection of the cable 910 (with its various wires, conduits, cables, etc. supported therein) to the composition dispenser 902 and the light module 906. The cable 910 may be routed or placed between the composition dispenser 902 and the light module 906 following more than one path. For example, a portion of the cable 910 may be supported on top of a counter top 922. Portions of the cable 910 may be mounted, coupled or otherwise fastened to the counter top 922 as well as portions of the light module 906 and/or the water dispenser 912 or other structures such as a wall. Indeed, those skilled in the art will recognize that the cable 910 can comprise any length, and can be routed along any path between the composition dispenser 902 and the light module 906.

Figure 9C:
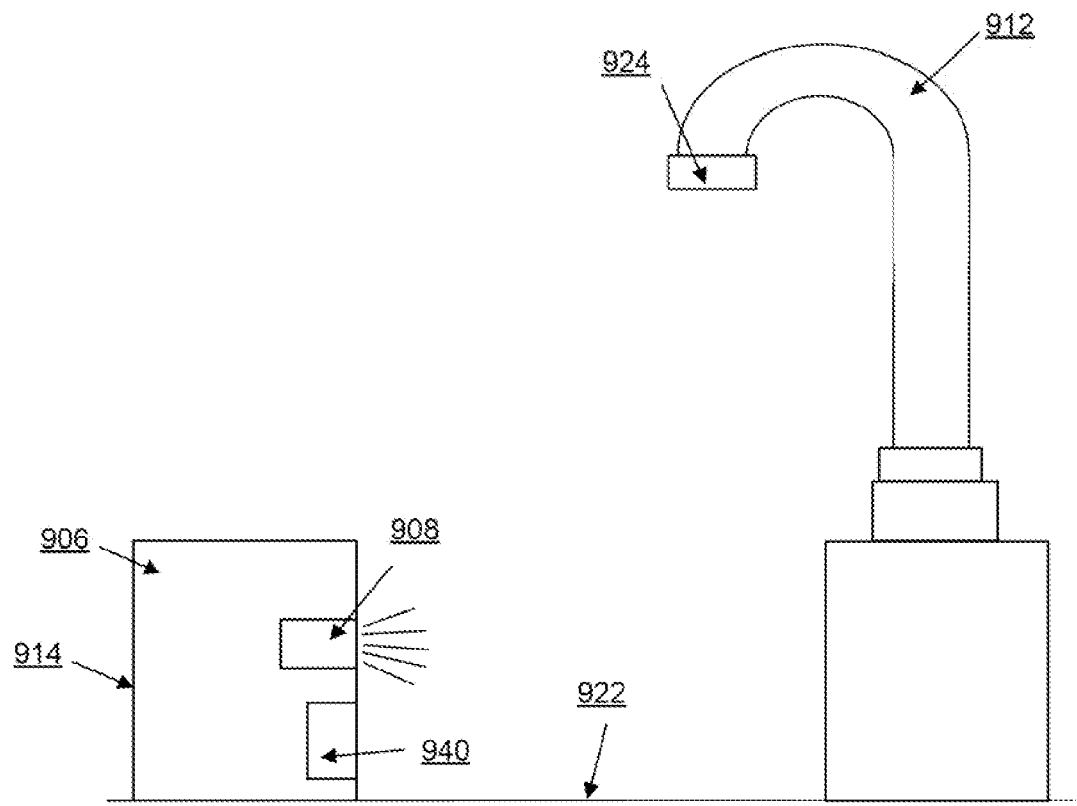
Figure 9D:
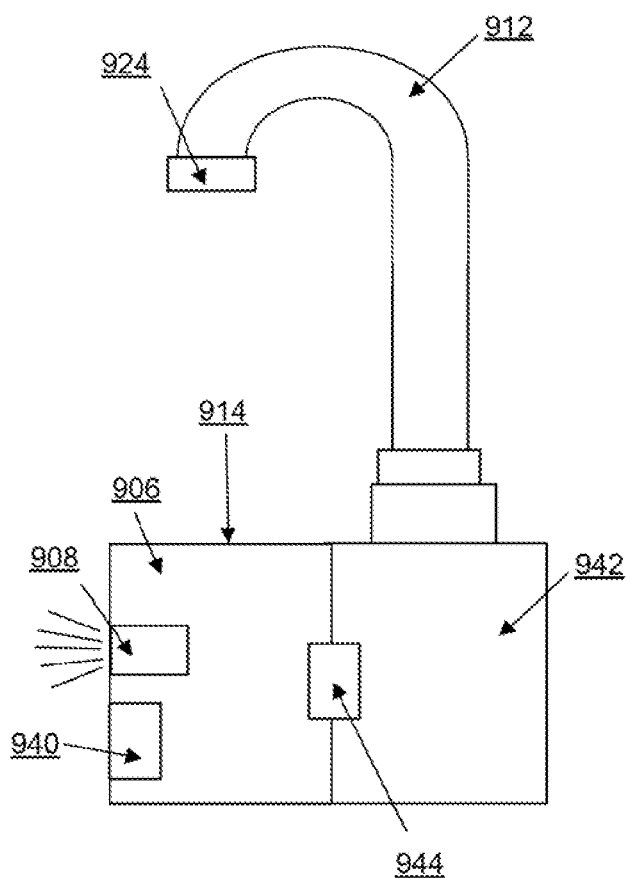

The light module 906 can be a free standing structure or it can be mounted to another structure. For example, the light module 906 may be free standing and placed near the water dispenser 912 (as is depicted in FIG. 9C). In such a configuration, the orientation and positioning in the module housing 914 of the light source 908 and other components, such as the camera 940, may be different than what is depicted in FIG. 9A. A light module 906 that is free standing may also be placed near an edge of the wash basin 926. In another example, the light module 906 may be mounted or coupled to a base 942 or other structure of the water dispenser 912 (as is depicted in FIG. 9D). The light module 906 may be mounted to the water dispenser 912 using a mounting device 944 such as screws, fasteners, zip ties, clamps, etc.

In one example, the light module 906 includes a light module interface 936 supported by the module housing 914 and configured to couple the light module 906 to the water dispenser 912, such as about the outlet 926 of the water dispenser 912. For example, the water dispenser 912 may include a threaded portion 946 that is male and the light module interface 936 may include a threaded portion that is female and designed to engage with the threaded portion 946. Thus, the light module 906 can be screwed onto or otherwise secured to the water dispenser 912. In another example, the light module interface 936 may comprise a clamping mechanism configured to facilitate the clamping and securing of the light module 906 to the water dispenser 912 about the outlet 926. The clamping mechanism can comprise a sleeve or other structural member capable of fitting over a male portion of the water dispenser 912. A sleeve of the light module interface 936 can be inserted over the male portion of the water dispenser 912. In one aspect, the sleeve can be clamped using an actuatable clamp that clamps and/or releases upon actuation. In another aspect, the sleeve can be configured to clamp using a friction fit.

In an embodiment where the light module 906 is attached or coupled to the water dispenser 912 about the outlet 926, as is depicted in FIG. 9A, the light module 906 can include a water conduit 948. The water conduit 948 can be internal to the light module 906 and can be configured to receive water from the outlet 926 and to pass the water out of the light module 906. Those skilled in the art will recognize that the light module 906 can be configured to both physically and fluidly couple to the water dispenser 912 in ways other than shown in the drawings and discussed herein, each of which are contemplated and intended to be covered herein. In any event, the light module interface 936 can function to provide both a physical coupling or connection and a fluid (water) coupling or connection of the light module 906 to the water dispenser 912. The light module 906 can further include a water dispensing system 950 that includes an actuator and a valve. The water dispensing system 950 can be supported in the module housing 914 and connected to the water conduit 948. The actuator can be activated to open the valve and dispense water through the water conduit 948. The water dispenser 912 can be left in the on or open position and the water dispensing system 950 configured to control dispensing of the water. The actuator can be activated by a touchless sensor, such as a sensor 952 supported in the module housing 914, or by a sensor 954 supported in the dispenser housing 916, or either sensor. The sensors 952 and 954 may be infrared sensors. The sensors 952 and 954 may also be employed to dispense the composition from the composition dispenser 902. Different movements or gestures of the individual may trigger timer programs, as described above, to dispense the water and emit the light from the light source 908. Additionally, dispensing of the composition may also be controlled by a timer program. The timer program may be stored in the memory 920 and executed via the processor 918. Indeed the processor 918 and memory 920 may be described as a timer. The sensor 952 and 954 can be connected to the processor 918 and the memory 920. The sensor 952 and the water dispensing system 950, including the actuator, can be connected to the processor 918 and memory 920 via the cable 910.

The composition dispenser 902 can include an image capturing system 974. The image capturing system can include a camera to capture images or video of a decontamination event. The camera 940 can be supported in the module housing 914. Alternatively, the camera can be part of the image capturing system 974 housed in the composition dispenser 902. In other words, the image capturing system 974 can have a camera in the composition dispenser 902 or the light module 906 or both. The camera 940 in the light module 906 can be controlled by the image capturing system 974 and powered by the power source 904. The camera 940 can be connected to the components of the composition dispenser 902 for control and power via the cable 910. The image capturing system 974 may be controlled by and make use of the processor 918 and memory 920.

The image capturing system 974 may have all of the same features and capabilities as those described for the image capturing system 118 of FIGS. 1A-G. The image capturing system 974 may be employed to identify the individual initiating the decontamination event, wherein the identification tag comprises personal identification indicia encoded in at least one of a barcode, a quick response (QR) code, a radio frequency identification (RFID) tag, or text that is recognized via optical character recognition, and wherein the image capturing system is operable with a computer system configured to associate an identity of the individual with a stored individual profile. Data captured by the image capturing system 974 can be stored on the memory 920, on a memory card associated with the data connection 956, or stored in a remote data base that is accessed via the data connection 956.

As discussed above, the image capturing system 974 can function as a sensor that is configured to detect the fluorescence of the fluorescent agent by analyzing at least one of the one or more images captured by the image capturing system. The analysis can take place using the processor 918 and memory 920 or a remote computing system accessed over a network. The analysis can also measure an intensity of the fluorescent agent that is present. The analysis can also measure an amount of time the fluorescent agent is present during the decontamination event. Analysis of the images from the image capturing system 974 can be used to generate a score grading or scoring the decontamination event. The composition dispenser 902 can also include an alert system 978 in communication with the image capturing system 974 configured to notify the individual when the fluorescence of the fluorescent agent is no longer detected about the portion of the skin or a covering of the skin of the individual. The alert system 978 can also be referred to as a notification system and can include a notification device.

The alert system 978 can be operable with a timer to notify the individual of the passage of timer during predetermined periods of time. The timer can be the processor 918 and the memory 92. For example, the alert system 978 with the notification device can provide visual, auditory, or haptic feedback to the individual. The alert system 978 can include lights that progressively illuminate or turn off during a predetermined period of time. The notification device of the alert system 978 can include a display that numerically counts time. The alert system 978 can also be a display that outputs information to a user regarding the power source 904, the composition, or specifically the fluorescent agent. For example, the alert system 978 can output information regarding the battery level or battery life remaining for a battery associated with the power source 904. The alert system 978 can notify a user that the battery needs to be replaced. The alert system 978 can output information regarding the amount of composition, fluorescent agent, or cleansing agent remaining in the composition dispenser 902.

The composition dispenser 902 can further comprise, and the dispenser housing 916 can further support, a fingerprint scanner 964. The fingerprint scanner 964 can receive fingerprint data from an individual when a finger or digit of the individual is pressed against a sensor of the fingerprint scanner 964. Fingerprint data for individuals can be stored in a database, such as database 410 of FIG. 4 or another database, and used to identify the individual during or prior to a decontamination event. The database may be stored locally in the components of the composition dispenser 902 or remotely. The identification made using the fingerprint data captured by the fingerprint scanner 964 can be used to store images captured by the image capturing system 974 and associate these with the identification of the individual.

The composition dispenser 902 can further comprise, and the dispenser housing 916 can further support, an identification system 966 supported in the dispenser housing and associated with the processor 918 and memory 920 to identify the individual initiating the decontamination event via a mobile device associated with the individual. The identification system 966 can be configured to wireless communicate with the mobile device to exchange personal identification information regarding an identity of the individual. The mobile device may be a computer system, such as computer system 404 of FIG. 4. The mobile device may be a smart phone, smart watch, or other personal electronic device that is carried by the individual. The individual may engage a button or input a command via other techniques such as voice commands on either the mobile device or the identification system 966 in order for the identification system to be initiated to identify the individual. The mobile device may execute software associated with the identification system 966 in order to communicate with the identification system 966. The identification system 966 and the mobile device may communicate wireless using cellular networks, WiFi, Bluetooth, near field communications, or other wireless protocols and hardware. Identifying an individual using any of the techniques described herein may cause the image capturing system 974 to record images of the decontamination event and store the images with metadata associated with the individual's identity. Identifying the individual may also cause the processor 918 and memory 920 to execute a timer program customized to the individual where the timer program may define time periods for and control the dispensing of the composition, the water, and the emission of the light from the light source 908. Such a customized timer program may be stored in the memory 920 or may be accessed by the processor 918 and memory 920 in a remote database over a network.

The power source 904 may further be associated with a power generator 968 supported in the module housing 914 that may comprise an impeller in the water conduit 948 that when turned or rotated will generate electricity to charge a battery associated with the power source 904. The power source 904 and the power generator may be electrically connected via the cable 910. The power generator 317 may have all of the same features and capabilities as those described for the power generator 122 of FIGS. 1A-G.

Figure 9E:
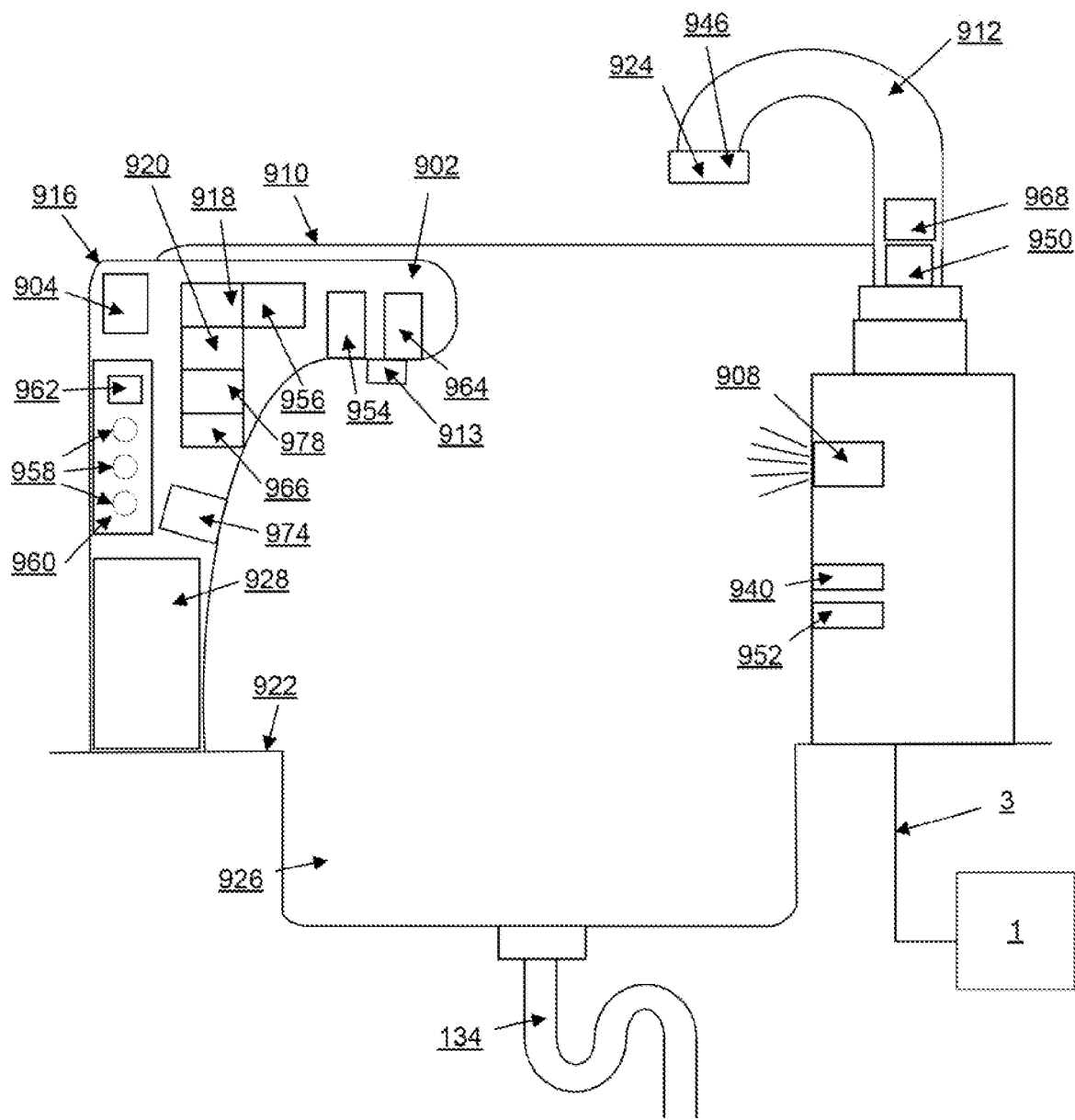

FIG. 9E depicts an embodiment where the light source 908 is purpose built into the water dispenser 912 at the time of manufacture. Such an embodiment can have other components also built into the water dispenser 912 such as the camera 940, sensor 952, the water dispensing system 950, and the power generator 968. The water dispenser 912 can be connected to the composition dispenser 902 via the cable 910 where the cable 910 may have a plurality of wires to supply electrical connections and data connections to the components of the water dispenser 912. Building the described components into the water dispenser 912 allows the composition dispenser 902 to be located remote from the wash basin 926. For example, the composition dispenser 902 may be mounted to a wall while the water dispenser 912 is located proximate to the wash basin 926 such that the light source 908 can emit light into the inspection space as described above.

Figure 4:
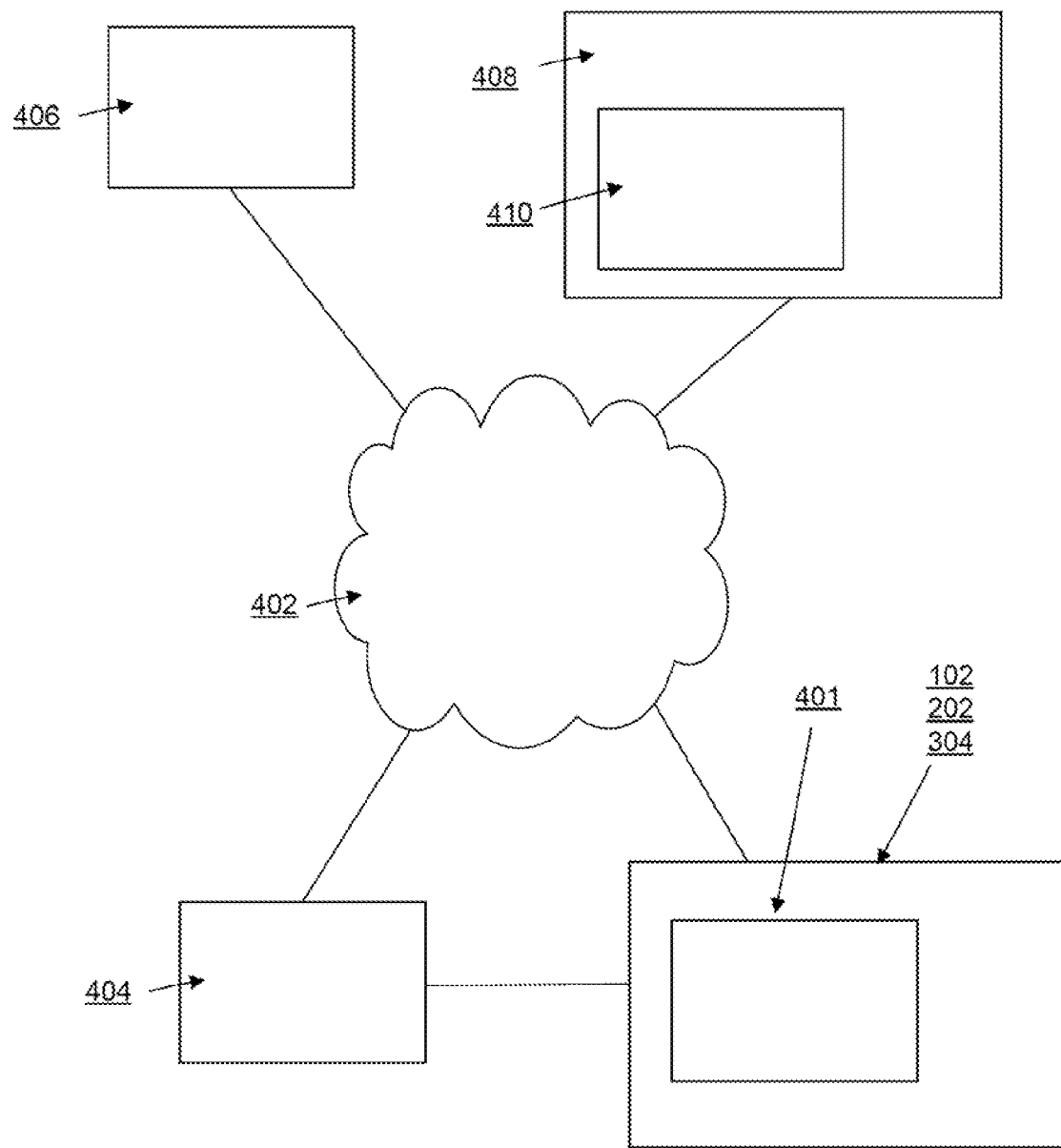
FIG. 4 is a block diagram of a computer network in accordance with one aspect of the technology.

FIG. 4 depicts a networking environment for computing devices in accordance with examples of the present technology. The networking environment can include a data connection device 401 for a device, system, apparatus, or component of the present technology. For example, the data connection device 401 can be the data connection supported on the water dispenser 102 of FIGS. 1A-G, the water dispenser 202 of FIGS. 2A-H, the dispensing apparatus 304 of FIGS. 3A-H, and the composition dispenser with the remote light module of FIGS. 9 A-E. The data connection device 401 is capable of transmitting and receiving data with another device. The data connection device 401 can communicate with another device directly or over a network 402. The data connection device 401 can communicate via a wired connection, wireless technology, or via removable storage.

In one example, the data connection device 401 can communicate with a computer system 404. The computer system 404 may be physically proximate to and directly connected to the data connection device 401. For example, the computer system 404 may be a laptop computer or a smart phone in the same room as the data connection device 401. The computer system 404 may be executing software or an application that is capable of communicating with the data connection device 401 and adjusting the settings of the data connection device 401 and associated of connected devices, systems, and/or components. For example, the application on the computer system 404 can modify a timer program installed on a timer associated with and in communication with the data connection device 401.

The computer system 404 as well as a computer system 406 and a computer system 408 can communicate with the data connection device 401 over a network 402. The network 402 may be the internet, a local area network, an ad hoc network, or another type of network. The data connection device 401 may connect to the network 402 or the computer system 404 via a wired connection or a wireless connection. The wireless connection may be WiFi, Bluetooth, Near-Field Communications, Zigbee, etc used for computer networking. The computer systems 404, 406, and 408 may be physically close or remote to the data connection device 401. Each of the computer systems 404, 406, and 408 can include, a bus, a processor, a memory, a storage device, input/output devices, and other components typically associated with computer systems. The computer system 408 can include a database 410. The computer system 404 and/or the computer system 406 can also comprise a database. The database 410, or other databases, may store user profile data such as a user identity and personal identification indicia associated with an identification tag for the user. The data connection device 401 may receive personal identification indicia from an image capturing system and then send the personal identification indicia to the computer system 408. The computer system 408 may then use the personal identification indicia to look up the user identity in the database 410 associated with a user profile. The user identity may then be sent back to the data connection device 401. The user's identity may then be used by the system or device associated with the data connection device 401 to record images of a decontamination event and associate the images with the user identity. The user identity may be saved as metadata for the images. The data connection device 401 may transmit the images to the computer system 408 for storage in the database 410.

The database 410 may also store other data associated with the present technology. For example, the database 410 may store timer programs for controlling the operations of a decontamination event. A user may create a custom timer program that is associated with a user identity for the user and store this in the database 410. Once a user is identified as using a system or device associated with the data connection device 401, the custom timer program for the user may be downloaded from the database 410 to the data connection device 401 so that the user may employ the custom timer program at the system where the user is located. The database 410 may also store scores that are generated for a decontamination event based on analyzing the images associated with a given decontamination event for a given user. The database 410 can further store predetermined user motions that can be matched with current motions to activate one or more timer programs, one or more light sources, an agent dispensing system, a water dispensing system, a water dispenser, and others as described herein.

Figure 5:
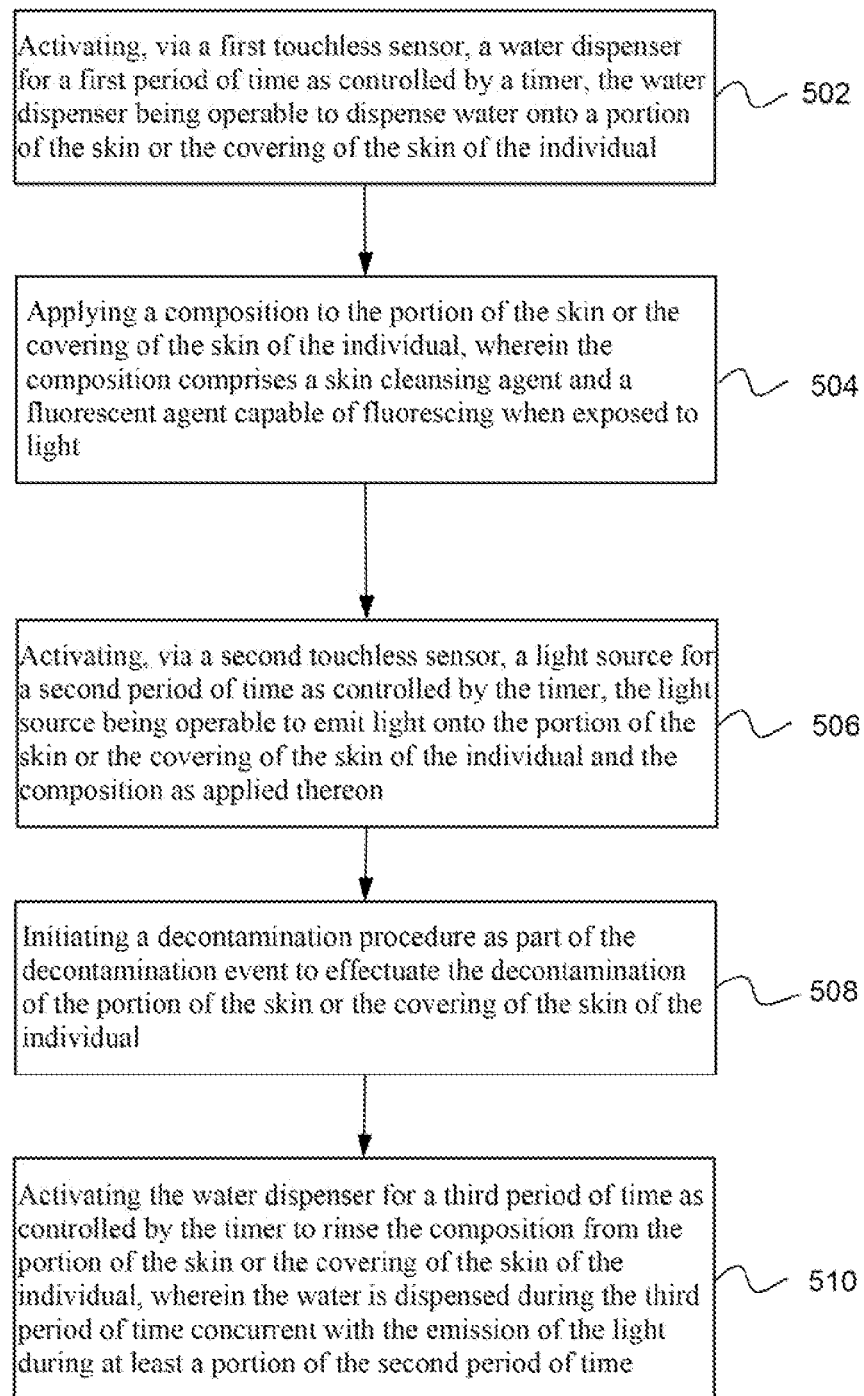
FIGS. 5-8 are flow charts illustrating certain aspects of the technology.

FIG. 5 is a flowchart of an example method 500 for facilitating effective decontamination of a portion of at least one of skin or a covering of the skin of an individual as part of a decontamination event, including assessing the effectiveness of the decontamination event according to an example of the present technology. The method can include, activating 502, via a first touchless sensor, a water dispenser for a first period of time as controlled by a timer, the water dispenser being operable to dispense water onto a portion of the skin or the covering of the skin of the individual. The method can include, applying 504 a composition to the portion of the skin or the covering of the skin of the individual, wherein the composition comprises a skin cleansing agent and a fluorescent agent capable of fluorescing when exposed to light. The method can include, activating 506, via a second touchless sensor, a light source for a second period of time as controlled by the timer, the light source being operable to emit light onto the portion of the skin or the covering of the skin of the individual and the composition as applied thereon. The method can further include, initiating 508 a decontamination procedure as part of the decontamination event to effectuate the decontamination of the portion of the skin or the covering of the skin of the individual. The method can include, activating 510 the water dispenser for a third period of time as controlled by the timer to rinse the composition from the portion of the skin or the covering of the skin of the individual, wherein the water is dispensed during the third period of time concurrent with the emission of the light during at least a portion of the second period of time.

The method can further include, activating the water dispenser for a third period of time comprises detecting, using a fluorescent emission intensity sensor or an image capturing system, an intensity of fluorescence of the fluorescent agent in the composition as applied to the skin or covering of the skin of the individual, and activating the water dispenser for the third period of time upon the fluorescent emission intensity sensor or an image capturing system detecting a predetermined intensity of fluorescence of the fluorescent agent. The method can further include, following the second and third periods of time, detecting any remaining traces of composition on the portion of the skin or the covering of the skin of the individual. The method can further include, in the event traces of the composition remain, activating the light source for a fourth period of time as controlled by the timer. The method can further include, activating the water dispenser for a fifth period of time as controlled by the timer to rinse any remaining composition from the portion of the skin or the covering of the skin of the individual, wherein the water is dispensed during the fifth period of time concurrent with the emission of the light during at least a portion of the fourth period of time. The method can further include, the detecting any remaining traces of composition comprises detecting a predetermined intensity of fluorescence of the fluorescent agent using a fluorescent emission intensity sensor or an image capturing system. The method can further include, selecting the skin cleansing agent from the group of skin cleansing agents consisting of: liquid soap, powdered soap, antibacterial soap, and antimicrobial soap. The method can further include, selecting the fluorescent agent from the group of fluorescent agents consisting of: compounds containing fluorophores, fluorescein, xanthene dyes, rhodamine dyes, stilbene dyes, functionalized polycyclic aromatic hydrocarbon dyes including lissamine flavine FF, pyranine, and/or amino G acid, triarylmethane dyes, methyl violet dyes, fuchsine dyes, phenol dyes, malachite green dyes, victoria blue dyes, diarylmethane dyes, and fluorescent fruit extracts including extracts from Viburnum trilobum, Ribes, and Ribes alpine.

Figure 6:
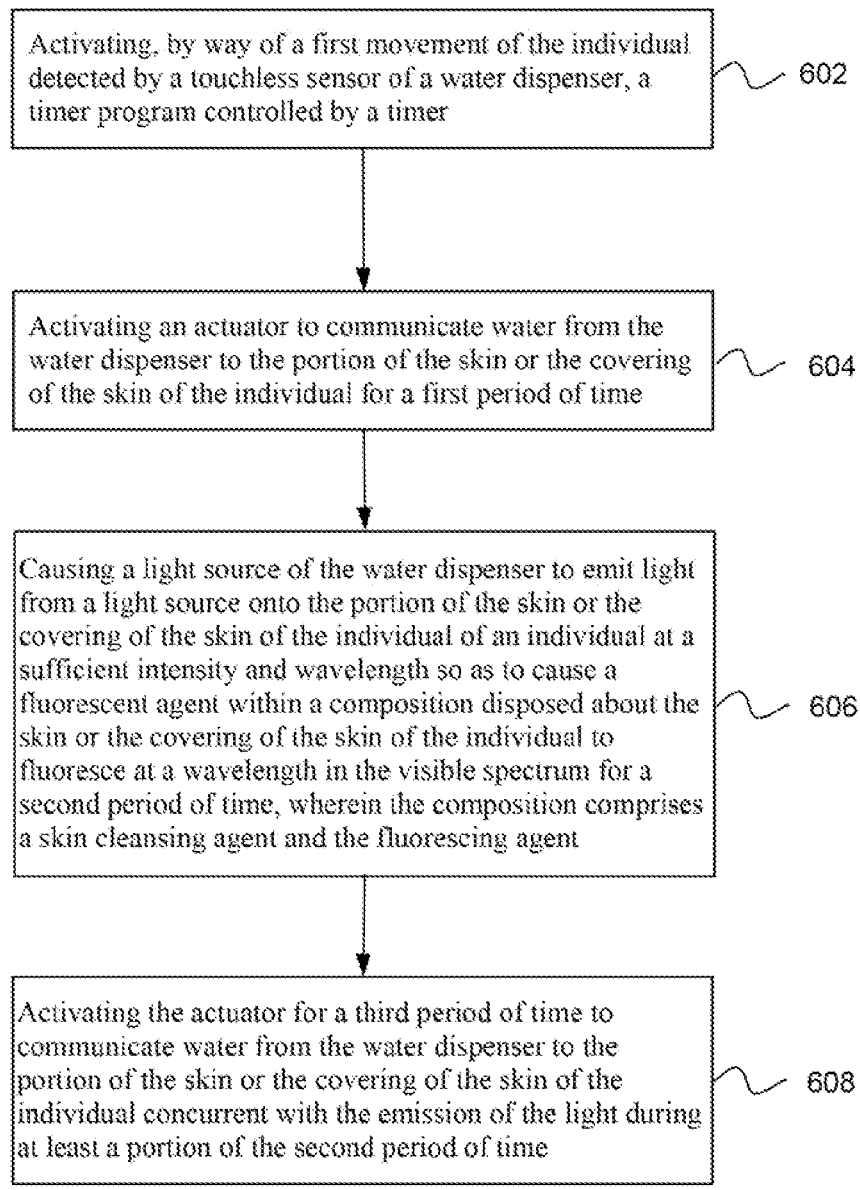

FIG. 6 is a flowchart of an example method 600 for facilitating effective decontamination of a portion of at least one of skin or a covering of the skin of an individual as part of a decontamination event, including assessing the effectiveness of the decontamination event according to an example of the present technology. The method can include, activating 602, by way of a first movement of the individual detected by a touchless sensor of a water dispenser, a timer program controlled by a timer. The activating the first timer program can include, activating 604 an actuator to communicate water from the water dispenser to the portion of the skin or the covering of the skin of the individual for a first period of time. The activating the first timer program can include, causing 606 a light source of the water dispenser to emit light from a light source onto the portion of the skin or the covering of the skin of the individual of an individual at a sufficient intensity and wavelength so as to cause a fluorescent agent within a composition disposed about the skin or the covering of the skin of the individual to fluoresce at a wavelength in the visible spectrum for a second period of time, wherein the composition comprises a skin cleansing agent and the fluorescing agent. The activating the first timer program can include, activating 608 the actuator for a third period of time to communicate water from the water dispenser to the portion of the skin or the covering of the skin of the individual concurrent with the emission of the light during at least a portion of the second period of time.

The method can further include, activating, by way of a second movement of the individual detected by the touchless sensor, the light source for a fourth period of time, and the actuator for a fifth period of time to communicate water from the water dispenser to the portion of the skin or the covering of the skin of the individual concurrent with the emission of the light during at least a portion of the fourth period of time. The method can further include, detecting any remaining traces of composition on the portion of the skin or the covering of the skin of the individual. The method can further include, activating the water dispenser for a third period of time. In association with this, the method can further include detecting, using a fluorescent emission intensity sensor or an image capturing system, an intensity of fluorescence of the fluorescent agent in the composition as applied to the skin or covering of the skin of the individual, and activating the water dispenser for the third period of time upon the fluorescent emission intensity sensor or an image capturing system detecting a predetermined intensity of fluorescence of the fluorescent agent. The method can further include, selecting the skin cleansing agent from the group of skin cleansing agents consisting of: liquid soap, powdered soap, antibacterial soap, and antimicrobial soap. The method can further include, the fluorescent agent from the group of fluorescent agents consisting of: compounds containing fluorophores, fluorescein, xanthene dyes, rhodamine dyes, stilbene dyes, functionalized polycyclic aromatic hydrocarbon dyes including lissamine flavine FF, pyranine, and/or amino G acid, triarylmethane dyes, methyl violet dyes, fuchsine dyes, phenol dyes, malachite green dyes, victoria blue dyes, diarylmethane dyes, and fluorescent fruit extracts including extracts from Viburnum trilobum, Ribes, and Ribes alpine.

Figure 7:
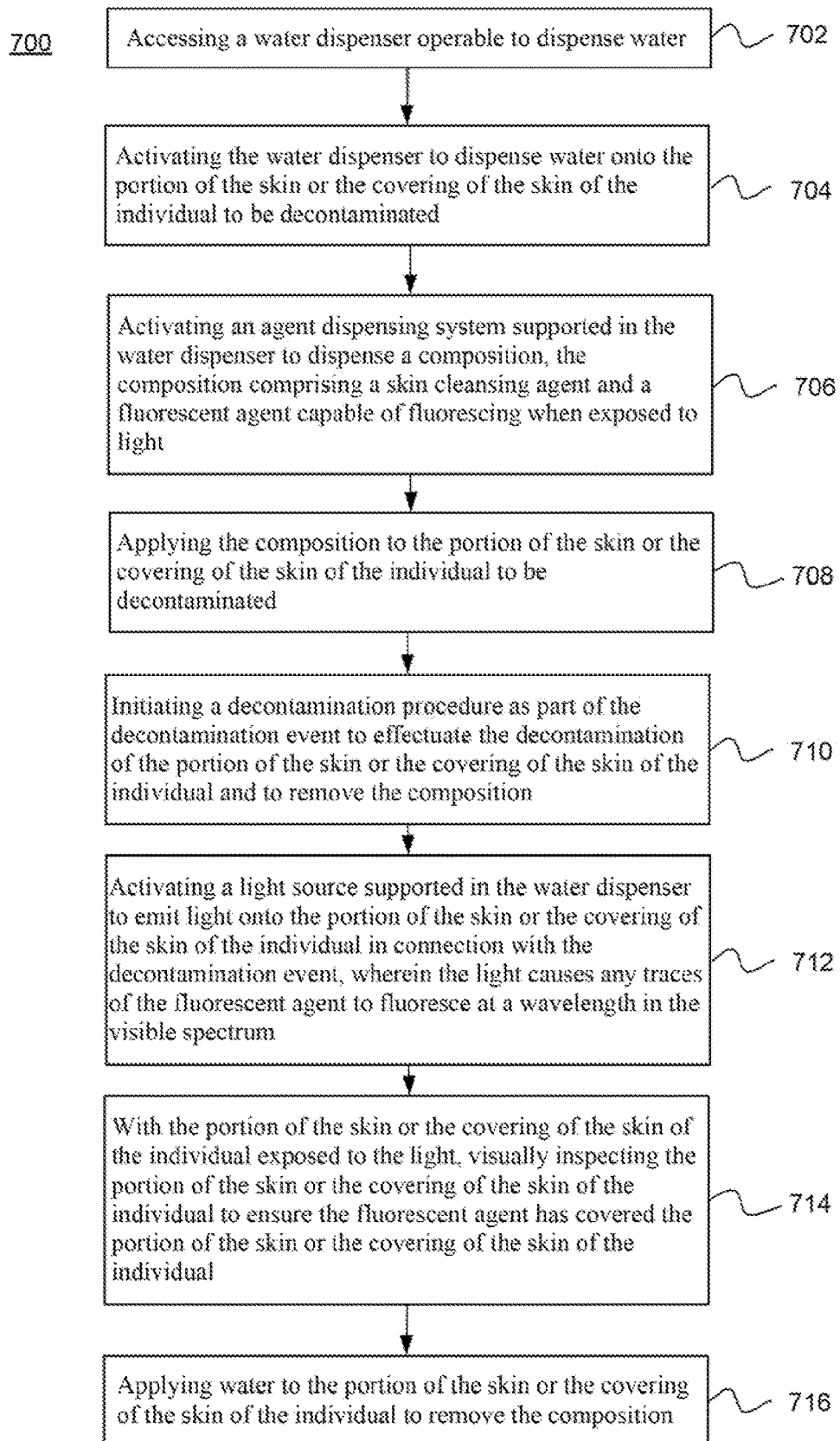

FIG. 7 is a flowchart of an example method 700 for facilitating effective decontamination of a portion of at least one of skin or a covering of the skin of an individual as part of a decontamination event, including assessing the effectiveness of the decontamination event according to an example of the present technology. The method can include, accessing 702 a water dispenser operable to dispense water. The method can include, activating the water dispenser to dispense water onto the portion of the skin or the covering of the skin of the individual to be decontaminated. The method can include, activating 704 an agent dispensing system supported in the water dispenser to dispense a composition, the composition comprising a skin cleansing agent and a fluorescent agent capable of fluorescing when exposed to light. The method can include, applying 706 the composition to the portion of the skin or the covering of the skin of the individual to be decontaminated. The method can include, initiating 708 a decontamination procedure as part of the decontamination event to effectuate the decontamination of the portion of the skin or the covering of the skin of the individual and to remove the composition. The method can include, activating 710 a light source supported in the water dispenser to emit light onto the portion of the skin or the covering of the skin of the individual in connection with the decontamination event, wherein the light causes any traces of the fluorescent agent to fluoresce at a wavelength in the visible spectrum. The method can include, with the portion of the skin or the covering of the skin of the individual exposed to the light, visually inspecting 712 the portion of the skin or the covering of the skin of the individual to ensure the fluorescent agent has covered the portion of the skin or the covering of the skin of the individual. The method can include, applying 714 water to the portion of the skin or the covering of the skin of the individual to remove the composition.

The method can further include, repeating the decontamination procedure and the inspecting of the portion of the skin or the covering of the skin of the individual to continue to remove remaining amounts of the composition. The method can further include, selecting the skin cleansing agent from the group of skin cleansing agents consisting of: liquid soap, powdered soap, antibacterial soap, and antimicrobial soap. The method can further include, selecting the fluorescent agent from the group of fluorescent agents consisting of: compounds containing fluorophores, fluorescein, xanthene dyes, rhodamine dyes, stilbene dyes, functionalized polycyclic aromatic hydrocarbon dyes including lissamine flavine FF, pyranine, and/or amino G acid, triarylmethane dyes, methyl violet dyes, fuchsine dyes, phenol dyes, malachite green dyes, victoria blue dyes, diarylmethane dyes, and fluorescent fruit extracts including extracts from Viburnum trilobum, Ribes, and Ribes alpine.

Figure 8:
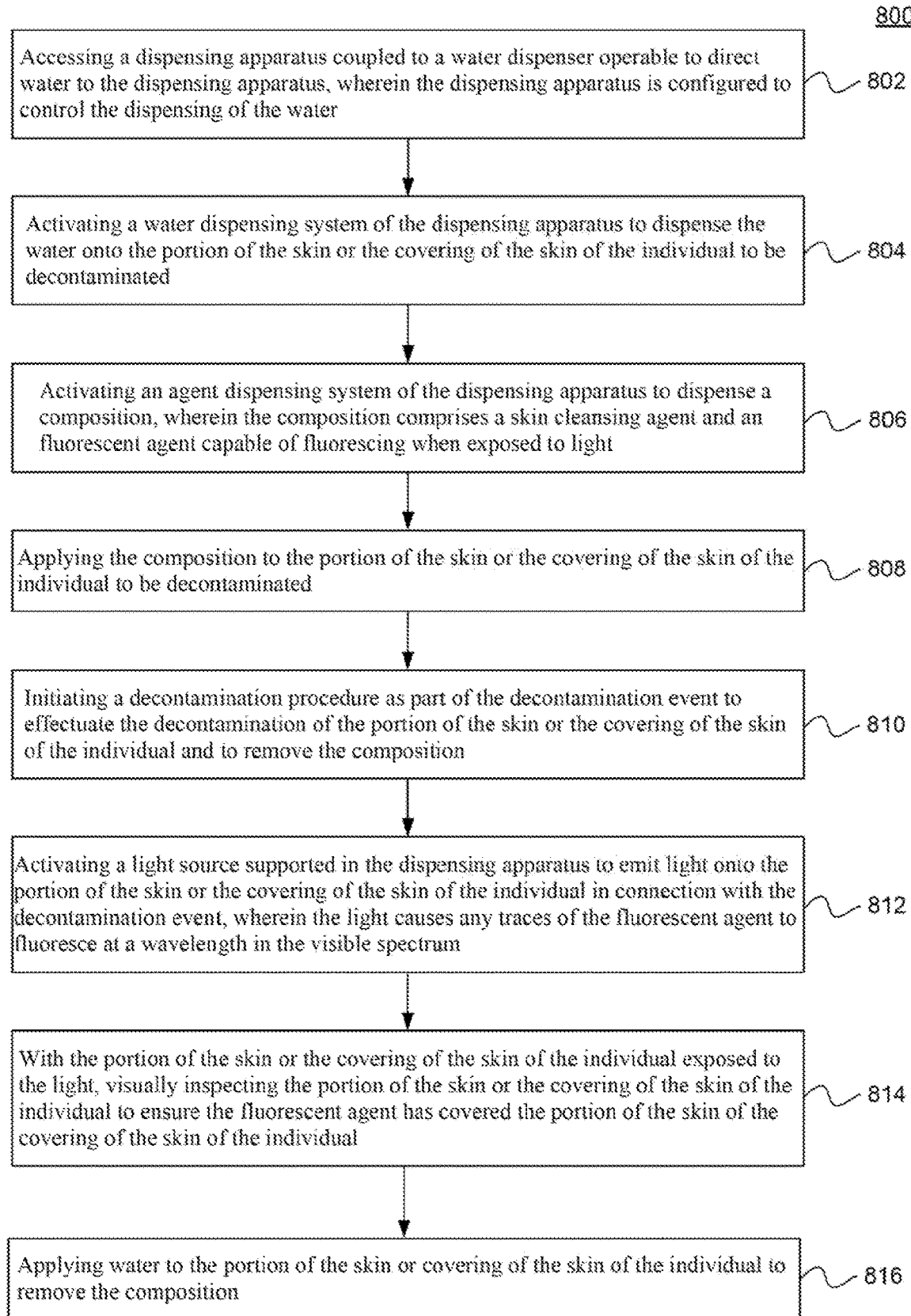

FIG. 8 is a flowchart of an example method 800 for facilitating effective decontamination of a portion of at least one of skin or a covering of the skin of an individual as part of a decontamination event, including assessing the effectiveness of the decontamination event according to an example of the present technology. The method can include, accessing 802 a dispensing apparatus coupled to a water dispenser operable to direct water to the dispensing apparatus, wherein the dispensing apparatus is configured to control the dispensing of the water. The method can further include, activating 804 a water dispensing system of the dispensing apparatus to dispense the water onto the portion of the skin or the covering of the skin of the individual to be decontaminated. The method can further include, activating 806 an agent dispensing system of the dispensing apparatus to dispense a composition, wherein the composition comprises a skin cleansing agent and an fluorescent agent capable of fluorescing when exposed to light. The method can further include, applying 808 the composition to the portion of the skin or the covering of the skin of the individual to be decontaminated. The method can further include, initiating 810 a decontamination procedure as part of the decontamination event to effectuate the decontamination of the portion of the skin or the covering of the skin of the individual and to remove the composition. The method can further include, activating 812 a light source supported in the dispensing apparatus to emit light onto the portion of the skin or the covering of the skin of the individual in connection with the decontamination event, wherein the light causes any traces of the fluorescent agent to fluoresce at a wavelength in the visible spectrum. The method can further include, with the portion of the skin or the covering of the skin of the individual exposed to the light, visually inspecting 814 the portion of the skin or the covering of the skin of the individual to ensure the fluorescent agent has covered the portion of the skin of the covering of the skin of the individual. The method can further include, applying 816 water to the portion of the skin or covering of the skin of the individual to remove the composition.

The method can further include, repeating the decontamination procedure and the inspecting of the portion of the skin or the covering of the skin of the individual to continue to remove remaining amounts of the composition. The method can further include, applying water to the portion of the skin or the covering of the skin of the individual as part of the decontamination event to enhance the decontamination procedure. The method can further include, selecting the skin cleansing agent from the group of skin cleansing agents consisting of: liquid soap, powdered soap, antibacterial soap, and antimicrobial soap. The method can further include, selecting the fluorescent agent from the group of fluorescent agents consisting of: compounds containing fluorophores, fluorescein, xanthene dyes, rhodamine dyes, stilbene dyes, functionalized polycyclic aromatic hydrocarbon dyes including lissamine flavine FF, pyranine, and/or amino G acid, triarylmethane dyes, methyl violet dyes, fuchsine dyes, phenol dyes, malachite green dyes, victoria blue dyes, diarylmethane dyes, and fluorescent fruit extracts including extracts from Viburnum trilobum, Ribes, and Ribes alpine.

FIG. 10 is a flowchart of an example method 1000 for facilitating effective decontamination of a portion of at least one of skin or a covering of the skin of an individual as part of a decontamination event, including assessing the effectiveness of the decontamination event according to an example of the present technology. The method can include, activating a composition dispenser to dispense a composition onto the portion of the skin or the covering of the skin of the individual to be decontaminated, the composition comprising a skin cleansing agent and a fluorescent agent capable of fluorescing when exposed to light. The method can further include, activating a light source, in response to the composition dispenser being activated, the light source being supported in a light module located remote to the composition dispenser to emit light onto the portion of the skin or the covering of the skin of the individual in connection with the decontamination event, wherein the light causes any traces of the fluorescent agent to fluoresce at a wavelength in the visible spectrum, wherein the light is emitted in an inspection space located between an outlet of a water dispenser and a wash basin. The method can further include, applying the composition to the portion of the skin or the covering of the skin of the individual to be decontaminated. The method can further include, with the portion of the skin or the covering of the skin of the individual exposed to the light, visually inspecting the portion of the skin or the covering of the skin of the individual to ensure the fluorescent agent has covered the portion of the skin of the covering of the skin of the individual. The method can further include, carrying out a decontamination procedure. The method can further include, applying water to the portion of the skin or covering of the skin of the individual to remove the composition.

The method can further include, applying water to the portion of the skin or the covering of the skin of the individual before activating the composition dispenser. The method can further include, repeating the decontamination procedure and the inspecting of the portion of the skin or the covering of the skin of the individual to continue to remove remaining amounts of the composition.

The foregoing detailed description describes the technology with reference to specific exemplary aspects. However, it will be appreciated that various modifications and changes can be made without departing from the scope of the present technology as set forth in the appended claims. The detailed description and accompanying drawings are to be regarded as merely illustrative, rather than as restrictive, and all such modifications or changes, if any, are intended to fall within the scope of the present technology as described and set forth herein.

More specifically, while illustrative exemplary aspects of the technology have been described herein, the present technology is not limited to these aspects, but includes any and all aspects having modifications, omissions, combinations (e.g., of aspects across various aspects), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Although the disclosure may not expressly disclose that some embodiments or features described herein may be combined with other embodiments or features described herein, this disclosure should be read to describe any such combinations that would be practicable by one of ordinary skill in the art. The user of "or" in this disclosure should be understood to mean non-exclusive or, i.e., "and/or," unless otherwise indicated herein.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The invention claimed is:

1. A system for facilitating effective decontamination of a portion of at least one of skin or a covering of the skin of an individual as part of a decontamination event, the system comprising:
  a composition dispenser having a dispenser housing, the composition dispenser configured to dispense a composition from a chamber supported in the dispenser housing, the composition comprising a skin cleansing agent and a fluorescent agent capable of fluorescing when exposed to light, the composition dispenser further comprising a power source supported by the dispenser housing;
  a light module having a module housing, and located remote from the composition dispenser, the light module further comprising a light source supported by the module housing and powered by the power source so as to emit light in accordance with a predetermined field of view;
  a cable connecting the composition dispenser and the light module, the cable comprising an electrical connection between the power source and the light source,
  wherein the light source is configured to emit the light at a sufficient intensity and wavelength so as to cause the fluorescent agent disposed about the skin or the covering of the skin of the individual to fluoresce at a wavelength in the visible spectrum, and wherein the field of view defines, at least in part, an inspection space located between a wash basin and an outlet of an independently operated water dispenser having a structural configuration separate from the dispenser housing of the composition dispenser and the module housing of the light module, in which the portion of the skin or the covering of the skin of the individual can be positioned to detect the presence or absence of fluorescing fluorescent agent during the decontamination event.

2. The system of claim 1, further comprising a light module interface supported by the module housing and configured to couple the light module to a structure.

3. The system of claim 2, wherein the structure is at least one of the water dispenser, a counter top, a backsplash, the wash basin, a wall, or a mirror.

4. The system of claim 2, wherein the light module interface comprises a threaded receiver operable to thread onto a threaded portion of the water dispenser.

5. The system of claim 2, wherein the light module interface comprises a sleeve configured to fit over an end of the water dispenser and operable to couple the module housing to the water dispenser via a friction fit.

6. The system of claim 1, wherein the light source is triggered to emit the light for a predetermined period of time when the composition dispenser is operated to dispense the composition.

7. The system of claim 1, wherein the cable comprises a data cable connecting the light module to the composition dispenser, the composition dispenser further comprising a controller with a processor and memory configured to control the light source via the data cable.

8. The system of claim 1, wherein the cable comprises a power cable that is energized with electricity to cause the light source to emit light.

9. The system of claim 1, wherein the composition dispenser comprises a touchless dispensing system having one or more sensors supported by the dispenser housing operable to facilitate touchless dispensing of the composition for application to the skin or a covering of the skin of the individual.

10. The system of claim 1, wherein the composition comprises a pre-mixed solution of the skin cleansing agent and the fluorescent agent.

11. The system of claim 1, wherein the chamber comprises a first sub-chamber containing the skin cleansing agent, a second sub-chamber containing the fluorescent agent, and wherein the composition dispenser comprises a mixing mechanism for mixing the skin cleansing agent and the fluorescent agent on-demand and prior to application of the composition to the skin or a covering of the skin of the individual.

12. The system of claim 1, wherein the skin cleansing agent is selected from the group of skin cleansing agents consisting of: liquid soap, powdered soap, hand sanitizer, antibacterial soap, and antimicrobial soap.

13. The system of claim 1, wherein the fluorescent agent is a fluorescent dye.

14. The system of claim 1, wherein the fluorescent agent is colorless when not fluorescing under light from the light source.

15. The system of claim 1, wherein the fluorescent agent is selected from the group of fluorescent agents consisting of: compounds containing fluorophores, fluorescein, xanthene dyes, rhodamine dyes, stilbene dyes, functionalized polycyclic aromatic hydrocarbon dyes including lissamine flavine FF, pyranine, and/or amino G acid, triarylmethane dyes, methyl violet dyes, fuchsine dyes, phenol dyes, malachite green dyes, victoria blue dyes, diarylmethane dyes, and fluorescent fruit extracts including extracts from Viburnum trilobum, Ribes, and Ribes alpine.

16. The system of claim 1, wherein the power source is selected from the group of power sources consisting of: a replaceable battery, a rechargeable battery, inductively transferred power, and an alternating current power source.

17. The system of claim 1, wherein the light source is configured to emit ultraviolet light at a wavelength in a range of 150-400 nanometers.

18. The system of claim 1, wherein the light is ultraviolet A (UVA), ultraviolet B (UVB), ultraviolet C (UVC), or a combination thereof.

19. The system of claim 1, wherein the light source is configured to emit visible light at a wavelength in a range of 400-700 nanometers.

20. The system of claim 1, wherein the light source is configured to emit infrared light at a wavelength in a range of 700 nanometers to 1 millimeter.

21. The system of claim 1, wherein the light is emitted at an intensity and wavelength so as to provide a germicidal effect when incident upon the skin or a covering of the skin of the individual.

22. The system of claim 1, further comprising:
an image capturing system, supported in the dispenser housing, the image capturing system comprising a camera in communication with a processor for capturing one or more images of the portion of the skin or the covering of the skin of the individual subject to the decontamination event, wherein the image capturing system is powered via the power source.

23. The system of claim 22, wherein the camera is supported in the module housing and connected to the image capturing system via a second cable.

24. The system of claim 22, wherein the image capturing system is configured to sense an identification tag used to identify the individual initiating the decontamination event, wherein the identification tag comprises personal identification indicia encoded in at least one of a barcode, a quick response (QR) code, or text that is recognized via optical character recognition, and wherein the image capturing system is operable with a computer system configured to associate an identity of the individual with a stored individual profile.

25. The system of claim 22, wherein the one or more images are stored on a removable memory storage device associated with the image capturing system.

26. The system of claim 22, wherein the image capturing system is in communication with a computer network, and is configured to transmit data corresponding to at least one of the one or more images and the personal identification indicia over the computer network, wherein a connection to the network is wired or wireless.

27. The system of claim 22, wherein the image capturing system functions as a sensor that is configured to detect the fluorescence of the fluorescent agent by analyzing at least one of the one or more images captured by the image capturing system, and wherein the composition dispenser further comprises a notification system in communication with the image capturing system configured to notify the individual when the fluorescence of the fluorescent agent is no longer detected about the portion of the skin or a covering of the skin of the individual.

28. The system of claim 22, wherein the image capturing system is configured to record at least a portion of the decontamination event.

29. The system of claim 22, wherein the image capturing system is configured to measure an intensity of the fluorescence of the fluorescent agent.

30. The system of claim 22, wherein the image capturing system is configured to measure an amount of time the fluorescence of the fluorescent agent is detected.

31. The system of claim 22, wherein the image capturing system is configured to generate a score based on results of the recording of the portion of the decontamination event.

32. The system of claim 22, wherein the image capturing system is configured to recognize and record movements of the individual associated with the decontamination event, and match these with stored predetermined acceptable movements associated with an operation of the dispensing apparatus, the image capturing system activating an operation of the dispensing apparatus upon determining a match.

33. The system of claim 1, further comprising:
an alert system supported in the dispenser housing and operable with a timer to time at least a portion of the decontamination event in accordance with one or more predetermined durations of time, and to notify the individual of an expiration of one or more durations of time, wherein the alert system comprises a notification device configured to provide visual, auditory, or haptic feedback.

34. The system of claim 33, wherein the notification device comprises a plurality of notification lights configured to progressively change status from an initiation of a decontamination procedure to the end of the decontamination procedure.

35. The system of claim 33, wherein the notification device comprises a display that numerically counts time intervals until the expiration of the duration of time.

36. The system of claim 33, wherein the alert system is configured to activate a notification when the fluorescent agent disposed about the skin or a covering of the skin of the individual fluoresces at a predetermined intensity.

37. The system of claim 33, wherein the alert system is configured to provide information regarding an amount of the composition remaining in the chamber.

38. The system of claim 33, wherein the fluorescent agent is stored in a sub-chamber of the chamber and the alert system is configured to provide information regarding an amount of the fluorescent agent remaining in the composition dispenser.

39. The system of claim 33, wherein the alert system is configured to provide information regarding an amount of battery life remaining for a battery associated with the power source.

40. The system of claim 1, further comprising:
a fingerprint scanner supported in the dispenser housing to identify the individual initiating the decontamination event, the fingerprint scanner operable with a computer system configured to associate the identity of the individual with a stored individual profile.

41. The system of claim 1, further comprising:
an identification system supported in the dispenser housing and associated with a memory and processor to identify the individual initiating the decontamination event via a mobile device associated with the individual, the identification system being configured to wirelessly communicate with a mobile device to exchange personal identification indicia regarding an identity of the individual.

42. The system of claim 41, wherein the mobile device includes a radio frequency identification (RFID) tag that communicates the personal identification indicia and is employed by the identification system to identify the individual.

\* \* \* \* \*